US011638750B2

(12) United States Patent
Guirakhoo et al.

(10) Patent No.: US 11,638,750 B2
(45) Date of Patent: May 2, 2023

(54) METHODS FOR GENERATING A ZIKV IMMUNE RESPONSE UTILIZING A RECOMBINANT MODIFIED VACCINA ANKARA VECTOR ENCODING THE NS1 PROTEIN

(71) Applicant: GEOVAX, INC., Smyrna, GA (US)

(72) Inventors: Farshad Guirakhoo, Atlanta, GA (US); Arban Domi, Atlanta, GA (US); Nathanael Paul McCurley, Decatur, GA (US)

(73) Assignee: Geovax, Inc., Smyrna, GA (US)

( * ) Notice: Subject to any disclaimer, the term of this patent is extended or adjusted under 35 U.S.C. 154(b) by 0 days.

(21) Appl. No.: 17/000,768

(22) Filed: Aug. 24, 2020

(65) Prior Publication Data

US 2021/0100891 A1 Apr. 8, 2021

Related U.S. Application Data

(63) Continuation of application No. 16/074,947, filed as application No. PCT/US2017/016013 on Feb. 1, 2017, now abandoned.

(60) Provisional application No. 62/290,744, filed on Feb. 3, 2016.

(51) Int. Cl.
*A61K 39/12* (2006.01)
*A61P 31/14* (2006.01)
*C12N 7/00* (2006.01)
*A61K 39/00* (2006.01)

(52) U.S. Cl.
CPC .............. *A61K 39/12* (2013.01); *A61P 31/14* (2018.01); *C12N 7/00* (2013.01); *A61K 2039/5254* (2013.01); *A61K 2039/5256* (2013.01); *A61K 2039/575* (2013.01); *C12N 2710/24143* (2013.01); *C12N 2770/24134* (2013.01); *C12N 2770/24171* (2013.01); *Y02A 50/30* (2018.01)

(58) Field of Classification Search
CPC .......... A61K 39/12; C12N 2710/24111; C12N 2710/24141; C12N 2710/24143; C12N 2770/24111; C12N 2770/24134
See application file for complete search history.

(56) References Cited

U.S. PATENT DOCUMENTS

| | | | |
|---|---|---|---|
| 6,440,422 B1 | 8/2002 | Sutter et al. | |
| 6,696,281 B1 | 2/2004 | Chambers et al. | |
| 7,550,147 B2 * | 6/2009 | Howley .................. | A61P 31/18 424/199.1 |
| 9,133,480 B2 * | 9/2015 | Moss ................... | C07K 14/005 |
| 11,052,148 B2 | 7/2021 | Guirakhoo et al. | |
| 11,098,086 B2 | 8/2021 | Robinson | |
| 11,278,607 B2 | 3/2022 | Robinson et al. | |
| 11,311,612 B2 | 4/2022 | Guirakhoo et al. | |
| 11,413,341 B2 | 8/2022 | Robinson et al. | |
| 2003/0215794 A1 | 11/2003 | Kawaoka et al. | |
| 2006/0088909 A1 | 4/2006 | Compans et al. | |
| 2006/0099225 A1 | 5/2006 | Bavari et al. | |
| 2006/0153874 A1 | 7/2006 | Howley et al. | |
| 2006/0159706 A1 | 7/2006 | Panicali et al. | |
| 2006/0188961 A1 | 8/2006 | Howley et al. | |
| 2006/0216702 A1 | 9/2006 | Compans et al. | |
| 2008/0019483 A1 | 8/2008 | Moss et al. | |
| 2010/0047277 A1 | 2/2010 | Compans et al. | |
| 2010/0143402 A1 | 6/2010 | Moss et al. | |
| 2010/0196419 A1 | 8/2010 | Compans et al. | |
| 2010/0330190 A1 | 12/2010 | Compans et al. | |
| 2011/0104199 A1 | 5/2011 | Moss et al. | |
| 2011/0262483 A1 | 10/2011 | Haynes et al. | |
| 2012/0052082 A1 | 3/2012 | Compans et al. | |
| 2012/0135501 A1 | 5/2012 | Howley et al. | |
| 2012/0219576 A1 | 8/2012 | Branco et al. | |
| 2012/0263750 A1 | 10/2012 | Moss et al. | |
| 2012/0289760 A1 | 11/2012 | Hill et al. | |
| 2013/0078276 A1 | 3/2013 | Robinson et al. | |
| 2013/0101618 A1 | 4/2013 | Sullivan et al. | |
| 2014/0255441 A1 | 9/2014 | Compans et al. | |
| 2014/0322265 A1 | 10/2014 | Chaplin et al. | |
| 2016/0318985 A1 | 11/2016 | Wang et al. | |
| 2019/0117758 A1 | 4/2019 | Robinson et al. | |

(Continued)

FOREIGN PATENT DOCUMENTS

| | | |
|---|---|---|
| EP | 0083286 | 7/1983 |
| EP | 0110385 | 6/1984 |

(Continued)

OTHER PUBLICATIONS

GenBank Accession No. KU312312, Jan. 2016, Zika virus isolate Z1106033 polyprotein gene, complete cds, submitted Dec. 16, 2015.*

(Continued)

*Primary Examiner* — Jeffrey S Parkin

(74) *Attorney, Agent, or Firm* — Knowles Intellectual Property Strategies, LLC

(57) ABSTRACT

The compositions and methods are described for generating an immune response to a flavivirus such as *Zika virus*. The compositions and methods described herein relate to a modified vaccinia Ankara (MVA) vector encoding one or more viral antigens for generating a protective immune response to a member of genus *Flavivirus* (such as a member of species *Zika virus*), in the subject to which the vector is administered. The compositions and methods of the present invention are useful both prophylactically and therapeutically and may be used to prevent and/or treat an infection caused by *Flavivirus*.

22 Claims, 10 Drawing Sheets

Specification includes a Sequence Listing.

(56) References Cited

U.S. PATENT DOCUMENTS

| | | | |
|---|---|---|---|
| 2019/0290745 A1 | 9/2019 | Robinson et al. |
| 2020/0171141 A1 | 6/2020 | Guirakhoo et al. |
| 2020/0282036 A1 | 9/2020 | Guirakhoo et al. |
| 2020/0289633 A1 | 9/2020 | Robinson et al. |
| 2022/0112248 A1 | 4/2022 | Robinson |
| 2022/0118082 A1 | 4/2022 | Guirakhoo et al. |
| 2022/0152190 A1 | 5/2022 | Robinson et al. |
| 2022/0160853 A1 | 5/2022 | Guirakhoo et al. |

FOREIGN PATENT DOCUMENTS

| | | |
|---|---|---|
| WO | WO 2004/048582 A1 | 6/2004 |
| WO | WO 2006/026667 A2 | 3/2006 |
| WO | WO 2015/066715 A1 | 5/2015 |
| WO | WO 2015/0175340 A1 | 11/2015 |
| WO | WO 2016/034678 A2 | 3/2016 |

OTHER PUBLICATIONS

U.S. Appl. No. 17/368,761, Guirakhoo et al., filed Jul. 6, 2021.
U.S. Appl. No. 17/409,574, Robinson, filed Aug. 23, 2021.
U.S. Appl. No. 17/542,100, Guirakhoo et al., filed Dec. 3, 2021.
U.S. Appl. No. 17/584,231, Robinson et al., filed Jan. 25, 2022.
Dejnirattisai, W., et al. "Dengue virus sero-cross-reactivity drives antibody-dependent enhancement of infection with zika virus," Nat Immunol 17, 1102-1108 (2016).
Kawiecki, A. B. & Christofferson, R. C. . "Zika Virus Induced Antibody Response Enhances Dengue Virus Serotype 2 Replication In Vitro," J Infect Dis 214, 1357-1360 (2016).
Smith, S. A., et al. "Dengue Virus prM-Specific Human Monoclonal Antibodies with Virus Replication-Enhancing Properties Recognize a Single Immunodominant Antigenic Site," J Virol 90, 780-789 (2015).
Stettler, K., et al. "Specificity, cross-reactivity, and function of antibodies elicited by Zika virus infec-tion," Science 353, 823-826 (2016).
Fuchs, J., et al. "Investigating the efficacy of monovalent and tetravalent dengue vaccine formulations against DENV-4 challenge in AG129 mice," Vaccine 32, 16 (2014).
Galula, J. U., Shen, W.-F., Chuang, S.-T., Chang, G.-J. J. & Chao, D.-Y. "Virus-Like Particle Secretion and Genotype-Dependent Immunogenicity of Dengue Virus Serotype 2 DNA Vaccine," Journal of Vi-rology 88, 18 (2014).
Lee, P. D., et al. "The Fc Region of an Antibody Impacts the Neutralization of West Nile Viruses in Dif-ferent Maturation States," J Virol 87, 13729-13740 (2013).
Edeling, M. A., Diamond, M. S. & Fremont, D. H. "Structural basis of Flavivirus NS1 assembly and antibody recognition," Proceedings of the National Academy of Sciences 111, 4285-4290 (2014).
Heinz, F. X. & Stiasny, K. Flaviviruses and flavivirus vaccines. Vaccine 30, 4301-4306 (2012).
International Search Report from PCT Patent Application No. PCT/US2017/016013, dated Mar. 21, 2017.
Wyatt, LS et al.; Elucidating and Minimizing the Loss by Recombinant Vaccinia Virus of Human Immunodeficiency Virus Gene Expression Resulting from Spontaneous Mutations and Positive Selec-tion. Journal of Virology. Jul. 2009, vol. 83, No. 14; pp. 7176-7184.
Musso, D et al.; Potential for Zika virus transmission through blood transfusion demonstrated 19-21 during an outbreak in French Polynesia, Nov. 2013 to Feb. 2014; Eurosurveillance; Apr. 10, 2014, vol. 19, No. 14; p. 1.
Aaskov JG. et al. Failure of a dengue 1 sub-unit vaccine to protect mice against a lethal dengue virus infection. Am J Trop Med Hyg. Nov. 1988;39(5):511-8.
Beltramello M. et al. The human immune response to Dengue virus is dominated by highly cross-reactive antibodies endowed with neutralizing and enhancing activity. Cell Host Microbe. 2010;8(3):271-283.
Brault, et al. "A Zika Vaccine Targeting NS1 Protein Protects Immunocompetent Adult Mice in a Lethal Challenge Model," Scientific Report, www.nature.com/scientificreports, 7: 14769, DOI:10.1038/s41598-017-15039-8, 2017.
Carroll MW. et al. Host range and cytopathogenicity of the highly attenuated MVA strain of vaccinia virus: propagation and generation of recombinant viruses in a nonhuman mammalian cell line. Virology. Nov. 24, 1997;238(2):198-211.
CDC. Zika virus—10 Public Health Achievements in 2016 and Future Priorities. vol. 2016 (US Department of Health and Human Services, CDC, Atlanta, GA, 2016).
C.f.M.P.f.H.U. Assessment report, IMVANEX, Common name: Modified Vaccinia Ankara virus, Procedure No. EMEA/H/C/002596. (ed. (CHMP), C.f.M.P.f.H.U.) (European Medicines Agency, London, UK, 2013).
Cornu T.I et al., "Ring Finger Z protein of lymphocytic choriomeningitis virus (LCMV inhibits transcription and RNA replication of an LCMV S-segment minigenome", Journal of Virologv, 2001, 75(19), 9415-9426.
Cosma A. et al. Therapeutic vaccination with MVA-H1V-1 nef elicits Nef-specific T-helper cell responses in chronically HIV-1 infected individuals. Vaccine. Dec. 8, 2003;22(1):21-9. doi: 10.1016/s0264-410x(03)00538-3.
Dejnirattisai W. et al. Cross-reacting antibodies enhance dengue virus infection in humans. Science. May 7, 2010;328(5979):745-8.
Diamond MS, Pierson TC, Fremont DH. The structural immunology of antibody protection against West Nile virus. Immunol Rev. Oct. 2008;225:212-25.
Dowd, K. A., et al. Broadly Neutralizing Activity of Zika Virus Immune Sera Identifies a Single Viral 1870 Serotype. Cell Rep 16, 1485-1491 (2016).
Emerging Infectious Disease Journal 22(2016).
Enfissi et al. "Zika virus genome from the Americas," The Lancet. vol 387. p. 227. Jan. 16, 2016.
Fauci et al. "Zika Virus in the Americas—Yet Another Arbovirus Threat,"—N Engl J Med. 374(7):601-604. Feb. 18, 2016.
Faye, O., et al. Molecular Evolution of Zika Virus during Its Emergence in the 20th Century. PLoS Negl Trop Dis 8, 10 (2014).
GenBank Accession AFV312002, glycoprotein [Marburg Marburgvirus], Protein—NCBI; 3 pages; 2013.
International Search Report from PCT/US2016/013021, dated Mar. 9, 2016.
Kaufman BM, Summers PL, Dubois DR, Cohen WH, Gentry MK, Timchak RL, Burke DS, Eckels KH. Monoclonal antibodies for dengue virus prM glycoprotein protect mice against lethal dengue infection. Am J Trop Med Hyg. Nov. 1989;41(5):576-80.
Lanciotti, R. S., Lambert, A. J., Holodniy, M., Saavedra, S. & del Carmen Castillo, L. Phylogeny of Zika Virus in Western Hemisphere, 2015.
Lashley, F.R and Jerry Durham., Emerging Infectious Diseases: Trends and Issues, Emerg Infect Dis., 2003, 9(12), 1660; 2002, New York Springer Pub.
Lee et al. The Fc region of an antibody impacts the neutralization of West Nile viruses in different maturation states. J Virol. Dec. 2013;87(24):13729-40.
Mackett M. et al. Vaccinia virus: a selectable eukaryotic cloning and expression vector. Proc Natl Acad Sci U S A. Dec. 1982;79(23):7415-9.
Manuel E. R. et al.: "Intergenic region 3 of modified vaccinia ankara is a functional site for insert gene expression and allows for potent antigen A. -specific immune responses", Virology, Elsevier, Amsterdam, NL, vol. 403, No. 2, Aug. 1, 2010 (Aug. 1, 2010), pp. 155-162.
Mayr, A. et al. "Origin, characteristics and use of the attenuated vaccinia strain MVA". Infection 3.1 (1975): 6-14.
Mayr, A., et al. "The smallpox vaccination strain MVA: marker, genetic structure, experience gained with the parenteral vaccination and behavior in organisms with a debilitated defence mechanism (author's transl)." Zentralblatt fur Bakteriologie, Parasitenkunde, Infektionskrankheiten und Hygiene. Erste Abteilung Originale. Reihe B: Hygiene, Betriebshygiene, praventive Medizin 167.5-6 (1978): 375-390.

(56) References Cited

OTHER PUBLICATIONS

Melo et al. "Zika virus intrauterine infection causes fetal brain abnormality and microcephaly: tip of the iceberg?," Ultrasound Obstet Gynecol. 47:6-7. 2016.
Meyer, H. et al. "Mapping of deletions in the genome of the highly attenuated vaccinia virus MVA and their influence on virulence." Journal of general virology 72.5 (1991): 1031-103 8.
Moss Bernard et al. "Reflections on the early development of poxvirus vectors", Vaccine, vol. 31, No. 39, pp. 4220-4222.
Oehler et al. "Zika virus infection complicated by Guillain-Barre syndrome—case report, French Polynesia, Dec. 2013," Euro Surveill. 19(9):pii=20720. Mar. 6, 2014.
Orubu et al., "Expression and cellular immunogenicity of a transgenic antigen driven by endogenous poxviral early promoters at their authentic loci in MVA", PLOS One, 2012, 7(6), e40167; doi:10.1371/journal.pone.0040167.
Perera, R., Khaliq, M. & Kuhn, R. J. Closing the door on Flaviviruses: Entry as a target for antiviral drug design. Antiviral Research 80, 11-22 (2008).
Petersen, E.M., et al. Interim Guidance for Preconception Counseling and Prevention of Sexual Transmission of Zika Virus for Persons with Possible Zika Virus Exposure—United States, Sep. 2016. MMWR Morb Mortal Wkly Rep 65(39):1077-1081, 4 (2016).
Polyprotein [Zika virus] GenBank: AHZ13508.1.
Radoshitzky S.R. et al., "Ebolavirus 11-Peptide Immunoadhesins Inhibit Marburgvirus and Ebolavirus Cell Entry", J. Virol., 2011, 85(17), 8502-8513.
Rodenhuis-Zybert IA et al. Immature dengue virus: a veiled pathogen?. PLoS Pathog. 2010;6(1):e1000718. doi:10.1371/journal.ppat.1000718.
Sanchez A et al., "The virion glycoproteins of Ebola viruses are encoded in two reading frames and are expressed through transcriptional editing", PNAS USA, 1996, 93(8), 3602-3607.
Salvato, Maria et al. "A Single Dose of Modified Vaccinia Ankara Expressing Lassa Virus-like Par- tides Protects Mice from Lethal Intra-cerebral Virus Challenge," Pathogens 2019, 8, 133.
Smith, G. L. et al. 1984 Biotech Genet Engin Rev 2:383-407.
Stauft, C. B., Gorbatsevych, O., Cello, J., Wimmer, E. & Futcher, B. Comparison of African, Asian, and American Zika Viruses in Swiss Webster mice: Virulence, neutralizing antibodies, and serotypes. bioRxiv (2016).
Stickl H et al. MVA-Stufenimpfung gegen Pocken. Klinische Erprobung des attenuierten Pocken-Lebendimpfstoffes, Stamm MVA [MVA vaccination against smallpox: clinical tests with an attenuated live vaccinia virus strain (MVA) (author's transl)]. Dtsch Med Wochenschr. Nov. 22, 1974;99(47):2386-92.
Sutter G. et al. Nonreplicating vaccinia vector efficiently expresses recombinant genes. Proc Natl Acad Sci USA. Nov. 15, 1992;89(22):10847-51.
Sutter, G. et al. "A recombinant vector derived from the host range-restricted and highly attenuated MVA strain of vaccinia virus stimulates protective immunity in mice to influenza virus." Vaccine 12.11 (1994): 1032-1040.
Swenson, D. L., 2004, Generation of Marburg virus-like particles by co-expression of glycoprotein and matrix protein, FEMS Immunol. Med. Microbial. 40:27-31.
Urata, S.; Yasuda, J., "Cis- and cell-type-dependent trans-requirements for Lassa virus-like particle production", J. Gen. Virol., 2015, 96 Pt 7, 1626-1635.
Vaughan, K., Greenbaum, J., Blythe, M., Peters, B. & Sette, A. Meta-analysis of All Immune Epitope Data in the Flavivirus Genus: Inventory of Current Immune Epitope Data Status in the Context of Virus Immunity and Immunopathology. Viral Immunol 23, 26 (2010).
Vázquez S. et al. Immune response to synthetic peptides of dengue prM protein. Vaccine. Mar. 15, 2002;20(13-14):1823-30.
Wang et al., "Modified HS promoter improves stability of insert genes while maintaining immunogenicity during extended passage of genetically engineered MVA vaccines", Vaccine, Feb. 10, 2010; 28(6):1547.doi:10.1016/j.vaccine.2009.11.056.
Who and Experts Prioritize Vaccines, Diagnostics and Innovative Vector Control Tools for Zika R&D. Saudi Med J. 2016;37(4):471-472.
Ye, L., et al., 2006, Ebola virus-like particles produced in insect cells exhibit dendritic cell stimulating activity and induce neutralizing antibodies, Viral. 351:260-270.
Zanluca et al. "First report of autochthonous transmission of Zika virus in Brazil". Mem Inst Oswaldo Cruz, Rio de Janeiro. 110(4):569-572. Jun. 2015.
Zika virus isolate Z110603 3 polyprotein gene, complete cds GenBank: KU312312.1.
Beatty, P.R. et al., Dengue virus NS1 triggers endothelial permeability and vascular leak that is prevented by NS1 vaccination, Sci Transl Med., 2015;7(304):304ra141.
Chung, K.M. et al., Antibody recognition of cell surface-associated NS 1 triggers Fc-gamma receptor-mediated phagocytosis and clearance of West Nile Virus-infected cells, J Virol., 2007;81(17):9551-5.
Schlesinger, J.J. et al., The Fc portion of antibody to yellow fever virus NS1 is a determinant of protection against YF encephalitis in mice. Virology, 1993;192(1):132-41.
Wan, SW et al., Protection against dengue virus infection in mice by administration of antibodies against modified nonstructural protein 1, PLoS One, 2014;9(3):e92495.
U.S. Appl. No. 17/726,254, Guirakhoo et al., filed Apr. 21, 2022.
U.S. Appl. No. 17/876,682, Robinson et al., filed Jul. 29, 2022.
U.S. Appl. No. 17/888,131, Hauser et al., filed Aug. 15, 2022.

* cited by examiner

Positions are given in kilobase pairs in the MVA genome. For clarity and brevity, diagram is not to scale.

FIG. 8

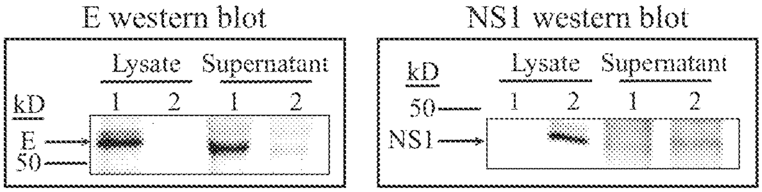

Expression of the Full-length ZIKV E and NS1 Proteins. 1. MVA-prME or MVA-NS1. 2. MVA Western blots. DF1 chicken fibroblast cells were co-transfected with MVA and plasmids expressing prME or NS1 genes of ZKV strain Suriname 2015. Blots performed with anti-ZIKV-E protein mouse monoclonal antibody (IgG1) from Aalto, Catalog # AZ1176 and anti-ZIKV-NS1 protein mouse monoclonal antibody (IgG1) from XXX, Catalog # AZ1225

MVA-Zika prME virus plaques

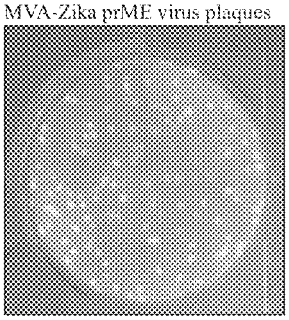

MVA-Zika prME plaques stained with Zika-specific E antibodies

EM of MVA-Zika prME infected cells: Multi-lamellar Structures Containing Zika VLPs

METHODS FOR GENERATING A ZIKV IMMUNE RESPONSE UTILIZING A RECOMBINANT MODIFIED VACCINA ANKARA VECTOR ENCODING THE NS1 PROTEIN

CROSS REFERENCE TO RELATED APPLICATIONS

This application is a continuation of U.S. patent application Ser. No. 16/074,974, filed Aug. 2, 2018, which is a national stage application under 35 U.S.C. § 371 of International Application No. PCT/US2017/016013, filed Feb. 1, 2017, which claims the benefit of U.S. 62/290,744 filed Feb. 3, 2016, the contents of which are incorporated by reference herein in their entirety.

INCORPORATION BY REFERENCE

The contents of the text file named "Sequence_Listing.txt" which was created on Nov. 30, 2020, and is 105 KB in size, are hereby incorporated by reference in their entirety.

FIELD OF THE INVENTION

The present invention is directed to compositions, including vaccine compositions, for generating an immune response to a *Flavivirus* such as a *Zika virus*, as well as methods of manufacture and use thereof. More specifically, the compositions and methods described herein relate to a modified vaccinia Ankara (MVA) vector encoding one or more viral antigens for generating a protective immune response to a member of the Flaviviridae family in a subject to which the vector is administered. The compositions and methods of the present invention are useful both prophylactically and therapeutically.

BACKGROUND OF THE INVENTION

*Zika virus* disease ("Zika") is an emerging infectious disease. It was first isolated in 1947 in Uganda, but until 2007 was known only to cause small outbreaks of minor public health significance (Enfissi, A., et al., The Lancet 387, 2 (2016)). Large epidemics occurred in 2007 in Yap Island in Micronesia and in 2013 in French Micronesia, raising the profile of Zika as an emerging disease (Oehler, E., et al. Eurosurveillance 19, 3 (2014) Zanluca, C., et al. Mem Inst Oswaldo Cruz 110, 4 (2015)). Beginning in 2015, with the appearance of the infection in Brazil, it became clear that Zika is a serious threat potentially capable of causing a pandemic (Zanluca, C., et al. Mem Inst Oswaldo Cruz 110, 4 (2015); Fauci, A. S. & Morens, D. M. New England Journal of Medicine (2016)). Today, Zika continue to spread—with multiple cases imported into the US by travelers from endemic regions. This rapid increase in transmission has prompted the world's public health authorities to mobilize quickly to control the epidemic. However, there is currently no treatment or vaccine available to fight the epidemic (CDC. *Zika virus*. Vol. 2016 (US Department of Health and Human Services, CDC, Atlanta, Ga., 2016)).

The etiologic agent of Zika is *Zika virus* (ZIKV), a member of the Flaviviridae family which also includes dengue fever, yellow fever, Japanese encephalitis, tick-borne encephalitis and West Nile viruses (Zanluca, C., et al. Mem Inst Oswaldo Cruz 110, 4 (2015)). ZIKV is transmitted primarily through bites from infected *Aedes* mosquitoes, but human-to-human sexual transmission may also occur (CDC. *Zika virus*. Vol. 2016 (US Department of Health and Human Services, CDC, Atlanta, Ga., 2016) Musso, D., et al. Emerg Infect Dis 21, 3 (2015)). Phylogenetic analyses of ZIKV demonstrate that this *Flavivirus* consists of one serotype and 2 major lineages: African and Asian, which are >96% identical in amino acid sequences across the genome. The Asian lineage has been responsible for all ZIKV outbreaks in the Pacific and the Americas. A vaccine composed of sequences from either lineage should theoretically protect against all Zika viruses. Monkeys are believed to be the animal reservoir, and humans are occasional/accidental hosts (Faye, O., et al. PLoS neglected tropical diseases 8, 10 (2014)).

ZIKV infection is asymptomatic in approximately 80% of cases (Petersen, E. M., et al. MMWR Morb Mortal Wkly Rep 65, 4 (2016)). Symptoms are generally mild, usually last no more than a week, and may include fever, malaise, headache, dizziness, anorexia, rash, arthralgia, and conjunctivitis (Petersen, E. M., et al. MMWR Morb Mortal Wkly Rep 65, 4 (2016)). ZIKV infections complicated by Guillain-Barre syndrome have been reported since 2004 (Oehler, E., et al. Eurosurveillance 19, 3 (2014) Petersen, E. M., et al. MMWR Morb Mortal Wkly Rep 65, 4 (2016)). More recently, an alarming association between ZIKV infection and fetal brain abnormalities including microcephaly has emerged (Melo, A. S. O., et al. Ultrasound Obstet Gynecol 47, 2 (2016)). With no approved preventive or therapeutic products currently available to fight the ZIKV epidemic, public health officials have no specific medical products at their disposal and their recommendations are limited to avoiding of exposure to ZIKV, delaying in becoming pregnant and following basic supportive care (fluids, rest, and ibuprofen) after infection (CDC. *Zika virus*. Vol. 2016 (US Department of Health and Human Services, CDC, Atlanta, Ga., 2016)). A vaccine is urgently needed to prevent a Zika pandemic.

Ab-dependent enhancement (ADE) of viral infection has been documented in vitro and in vivo as a significant risk with ZIKV E protein-directed vaccines when applied in dengue endemic areas (Dejnirattisai, W., et al. Dengue virus sere-cross-reactivity drives antibody-dependent enhancement of infection with zika virus. *Nat Immunol* 17, 1102-1108 (2016). Kawiecki, A. B. & Christofferson, R. C. Zika Virus-Induced Antibody Response Enhances Dengue Virus Serotype 2 Replication In Vitro. *J Infect Dis* 214, 1357-1360 (2016). Smith, S. A., et al. Dengue Virus prM-Specific Human Monoclonal Antibodies with Virus Replication-Enhancing Properties Recognize a Single Immunodominant Antigenic Site. J Virol 90, 780-789 (2015); Stettler, K., et al. Specificity, cross-reactivity and function of antibodies elicited by *Zika virus* infection (*Science* 353, 823-826 (2016)). Large-scale studies have not yet been performed to rule out the threat of ADE (e.g. use of ZIKV vaccines in dengue endemic countries), and E protein-targeted zika vaccines could potentially present a risk to those vaccinated. Moreover, PrM, a chaperon protein for E, induces limited neutralizing activities (Aaskov et al., 1988; Beltramello et al., 2010; Kaufman et al., 1989; Vazquez et al., 2002). It has been suggested that these antibodies contribute to the pathogenesis of DENV virus infection (Dejnirattisai et al., 2010; Rodenhuis-Zybert et al., 2010). Given that ZIKV and DENV are co-endemic throughout their distributions, an alternative to prME proteins as a vaccine target is attractive.

Currently, there is no vaccine for humans against the *Zika virus*. What is therefore needed are vaccine compositions and methods of use to prevent and treat disease caused by *Zika virus* infection.

SUMMARY OF THE INVENTION

The compositions and methods of the invention described herein are useful for generating an immune response to at least one Flaviviridae virus in a subject in need thereof. Advantageously, the compositions and methods may be used prophylactically to immunize a subject against *Zika virus* infection, or used therapeutically to prevent, treat or ameliorate the onset and severity of disease.

In a first aspect, the present invention is a recombinant modified vaccinia Ankara (MVA) vector comprising at least one nucleic acid sequence encoding a *Flavivirus* protein, wherein the at least one nucleic acid sequence is inserted into the MVA vector under the control of at least one promoter compatible with poxvirus expression systems.

In one embodiment, the recombinant MVA vector comprises at least two nucleic acid sequences encoding *Flavivirus* proteins, wherein the at least two nucleic sequences are inserted into the MVA vector under the control of at least two promoters capable compatible with poxvirus expression systems.

In one embodiment, the recombinant MVAvector comprises a first nucleic acid sequence encoding a *Flavivirus* structural protein and a second nucleic sequence encoding a *Flavivirus* nonstructural (NS) protein, wherein both the first and second nucleic acid sequences are inserted into the MVA vector under the control of promoters compatible with poxvirus expression systems.

In one embodiment, the *Flavivirus* structural protein is selected from remembrance-E (PrM-E), soluble E without a transmembrane domain, E protein domain I, E protein domain II, or E protein domain III, PrM and fragments thereof.

In one embodiment, the *Flavivirus* non-structural protein is selected from NS1, NS2A, NS2B, NS3, NS4A, NS4B, NSS and fragments thereof.

In one embodiment, the *Flavivirus* non-structural protein is a NS1 non-structural protein sequence.

In one embodiment, the first and second nucleic acid sequences are inserted into one or more deletion sites of the MVA vector.

In one embodiment, the first and second nucleic acid sequences are inserted into the recombinant MVA vector in a natural deletion site, a modified natural deletion site, or between essential or non-essential MVA genes.

In another embodiment, the first and second nucleic acid sequences are inserted into the same natural deletion site, a modified natural deletion site, or between the same essential or non-essential MVA genes In another embodiment, the first nucleic acid sequence is inserted into a deletion site selected from I, II, III, IV, V or VI and the nonstructural protein sequence is inserted into a deletion site selected from I, II, III, IV, V or VI.

In another embodiment, the first and second nucleic acid sequences or fragments thereof are inserted into different natural deletion sites, modified deletion sites, or between different essential or non-essential MVA genes.

In another embodiment, the first nucleic sequence is inserted in a first deletion site and the second nucleic acid sequence is inserted into a second deletion site.

In a particular embodiment, the first nucleic acid sequence is inserted between two essential and highly conserved MVA genes and the second nucleic acid sequence is inserted into a restructured and modified deletion III.

In a particular embodiment, the non-structural protein is NS1.

In one embodiment, the deletion III is modified to remove non-essential sequences and the second nucleic acid sequence is inserted between essential genes.

In a particular embodiment, the first nucleic acid sequence is inserted between two essential and highly conserved MVA genes to limit the formation of viable deletion mutants.

In a particular embodiment, the first nucleic acid sequence is inserted between MVA genes, I8R and G1L.

In one embodiment, the promoter is selected from the group consisting of Pm2H5, Psyn II, and mHS promoters or combinations thereof.

In one embodiment, the first nucleic acid sequence is optimized. In a particular embodiment, the first nucleic acid sequence is optimized by i) changing selected codons to other synonymous codons that are optimal for structural protein expression by MVA, ii) interrupting homopolymer stretches using silent mutations, iii) interrupting transcription terminator motifs using silent mutations, and iv) combinations thereof.

In one embodiment, the recombinant MVA vector expresses structural protein and non-structural proteins that assemble into VLPs.

In one embodiment, the structural protein sequence and the non-structural protein sequence are from a *Flavivirus* species.

In a second aspect, the present invention is a pharmaceutical composition comprising the recombinant MVA vector of the present invention and a pharmaceutically acceptable carrier.

In one embodiment, the recombinant MVA vector is formulated for intraperitoneal, intramuscular, intradermal, epidermal, mucosal or intravenous administration.

In a third aspect, the present invention is a pharmaceutical composition comprising a first recombinant MVA vector and a second recombinant MVA vector, each comprising a first nucleic acid sequence encoding a *Flavivirus* structural protein and a second nucleic acid sequence encoding a *Flavivirus* non-structural protein, wherein (i) the first nucleic acid sequence of the first recombinant MVA vector is different than the first nucleic acid sequence of the second recombinant MVA vector and/or (ii) the second nucleic acid sequence of the first recombinant MVA vector is different than the second nucleic acid sequence of the second recombinant MVA vector.

In a particular embodiment, the first nucleic sequence encodes premembrane-E, and the first nucleic acid sequence of the first recombinant MVA vector is from a different species than the first nucleic acid sequence of the second recombinant MVA vector.

In another particular embodiment, the second nucleic acid sequence of the first recombinant MVA vector is from a different species than the second nucleic acid sequence of the second recombinant MVA vector.

In a particular embodiment, at least one of the species of *Flavivirus* is *Zika virus*

In a particular embodiment, the non-structural protein sequence is NS1.

In a fourth aspect, the present invention is a pharmaceutical composition comprising three or more recombinant MVA vectors each comprising a first nucleic acid sequence encoding a *Flavivirus* structural protein and a second nucleic acid sequence encoding a *Flavivirus* non-structural protein sequence, wherein (i) the first nucleic acid sequence of the three or more recombinant MVA vectors are different and/or (ii) the second nucleic acid sequence of the three recombinant MVA vectors are difference.

In a particular embodiment, the first nucleic acid sequence encodes premembrane-E, and the first nucleic acid sequence of the first recombinant MVA vector is from a different species than the first nucleic acid sequence of the second recombinant MVA vector and is from a different species than the first nucleic acid sequence of the third recombinant MVA vector.

In a particular embodiment, the first nucleic acid sequence of each recombinant vector are from the same species.

In a particular embodiment, the first nucleic acid sequence of the three or more recombinant MVA vectors are from different species.

In a particular embodiment, at least one of the species of *Flavivirus* is *Zika virus*.

In a fifth aspect, the present invention is a method of inducing an immune response in a subject in need thereof, said method comprising administering the composition of the present invention to the subject in an amount sufficient to induce an immune response.

In one embodiment, the immune response is a humeral immune response, a cellular immune response or a combination thereof.

In a particular embodiment, the immune response comprises production of binding antibodies against the flavivirus.

In a particular embodiment, the immune response comprises production of neutralizing antibodies against the flavivirus.

In a particular embodiment, the immune response comprises production of non-neutralizing antibodies against the flavivirus.

In a particular embodiment, the immune response comprises production of a cell-mediated immune response against the flavivirus.

In a particular embodiment, the immune response comprises production of neutralizing and non-neutralizing antibodies against the flavivirus.

In a particular embodiment, the immune response comprises production of neutralizing antibodies and cell-mediated immunity against the flavivirus.

In a particular embodiment, the immune response comprises production of non-neutralizing antibodies and cell-mediated immunity against the flavivirus.

In a particular embodiment, the immune response comprises production of neutralizing antibodies, non-neutralizing antibodies, and cell-mediated immunity against the Flaviviridae virus.

In a particular embodiment, the immune response comprises production of neutralizing antibodies, non-neutralizing antibodies, and cell-mediated immunity against the *Zika virus*.

In a sixth aspect, the present invention is a method of preventing a Flaviviridae virus infection in a subject in need thereof, said method comprising administering the recombinant MVA vector of the present invention to the subject in a prophylactically effective amount.

In one embodiment, the viral infection is a *Zika virus* infection.

In a seventh aspect, the present invention is a method of inducing an immune response in a subject in need thereof, said method comprising administering the recombinant MVA vector of the present invention to the subject in a prophylactically effective amount.

In one embodiment, the immune response is considered a surrogate marker for protection.

In one embodiment, the method induces an immune response against a *Zika virus*.

In an eighth aspect, the present invention is a method of treating Flaviviridae virus infection in a subject in need thereof, said method comprising administering the recombinant MVA vector in a therapeutically effective amount to the subject.

In one embodiment, the Flaviviridae virus infection is caused by a *Zika virus*.

In one embodiment, the subject is exposed to Flaviviridae fever virus, but not yet symptomatic of Flaviviridae virus infection. In a particular embodiment, treatment results in prevention of a symptomatic infection.

In another embodiment, the subject is recently exposed but exhibits minimal symptoms of infections.

In another embodiment, the method results in amelioration of at least one symptom of infection.

In one embodiment, the symptom of infection is selected from mild headaches, maculopapular rash, fever, malaise, conjunctivitis, joint pains or a combination thereof.

In another embodiment, the method results in reduction or elimination of the subject's ability to transmit the infection to an uninfected subject.

In one embodiment, the method prevents or ameliorates a *Zika virus* infection.

In a ninth aspect, the present invention is a method manufacturing a recombinant MVAvector comprising inserting at least one nucleic acid sequence encoding premembrane-E and at least one nucleic acid sequence encoding a non-structural protein sequence into the recombinant MVA vector, wherein each nucleic acid sequence is operably linked to a promoter compatible with poxvirus expression systems.

In one embodiment, the non-structural sequence is NS1 and the premembrane-E sequence is PrM-E.

In a particular embodiment, the NS1 sequence and the PrM-E sequence are from a *Zika virus*.

In one embodiment, the recombinant MVA viral vector expresses *Zika virus* premembrane-E and NS1 proteins that assemble into VLPs.

The numbering illustrates the positions (in kilobase pairs) of the various elements in the genome of the MVA vaccine vector. For clarity and brevity, the diagram is not to scale; pairs of diagonal lines indicate a section of the MVA genome that is not illustrated because its contents are not relevant to the invention. Arrows labeled "PrM-E" and "NS1" illustrate the positions of the genes encoding premembrane-E and NS1, respectively, for use with *Zika virus* sequences. Rectangles labeled "I8R" and "G1L" indicate the positions of the two MVA genetic elements flanking the gene encoding PrME. Rectangles labeled "ASOR" and "B1R" indicate the positions of the two MVA genetic elements flanking the gene encoding NS1.

Figure 1:
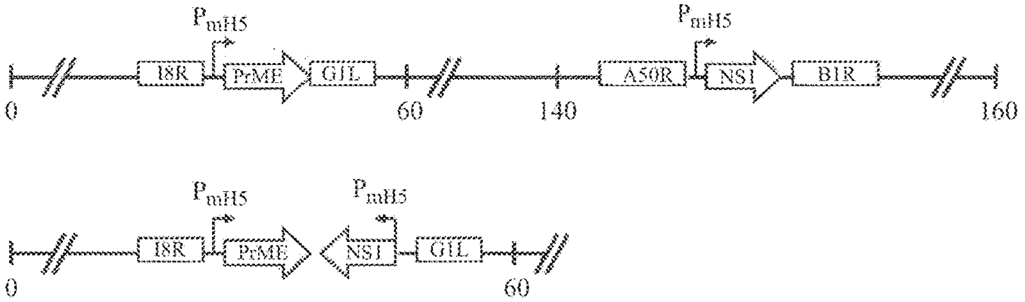
FIG. 1 is a simple line drawing illustrating the design of the MVA vectors.
Figure 2:
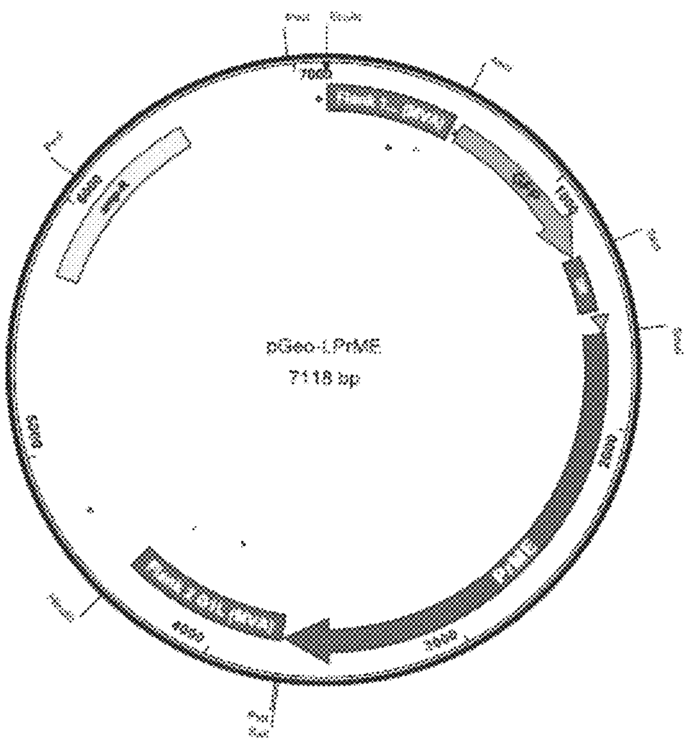

FIG. 2 is a schematic for the shuttle vector for flavivirus PrM-E.

The ampicillin resistance marker, allowing the vector to replicate in bacteria, is illustrated with a block labeled "amp-R." The two flanking sequences, allowing the vector to recombine with the MVA genome, are illustrated with a block and a block labeled "Flank 1" and "Flank 2" respectively. The green fluorescent protein (GFP) selection marker, allowing the selection of recombinant MVAs, is illustrated with an arrow labeled "GFP." The block labeled "DR" illustrates the location of a sequence homologous to part of Flank 1 of the MVA sequence. DR enables removal of the GFP sequence from the MVA vector after insertion of PrM-E into the MVA genome. The modified HS (mHS) promoter, which enables transcription of the inserted heterologous gene, is illustrated with a triangle between the DR and PrM-E elements. The flavivirus PrM-E gene is illustrated with an arrow labeled "PrM-E".

Figure 3:
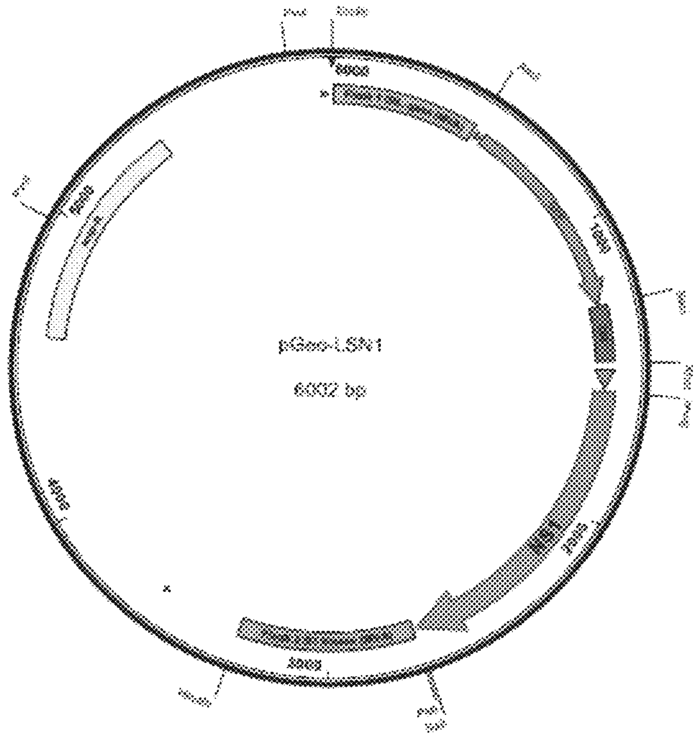

FIG. 3 is a schematic for the shuttle vector for flavivirus NS1.

The ampicillin resistance marker, allowing the vector to replicate in bacteria, is illustrated with a block labeled "amp-R." The two flanking sequences, allowing the vector to recombine with the MVA genome, are illustrated with blocks labeled "Flank 1" and "Flank 2." The green fluorescent protein (GFP) selection marker, allowing the selection of recombinant MVAs, is illustrated with an arrow labeled "GFP." The block labeled "DR" illustrates the location of a sequence homologous to part of Flank 1 of the MVA sequence. DR enables removal of the GFP sequence from the MVA vector after insertion of NS1 into the MVA genome. The modified HS (mHS) promoter, which enables transcription of the inserted heterologous gene, is illustrated with a triangle between the DR and NS1 elements. The flavivirus NS1 gene is illustrated with an arrow labeled "NS1."

Figure 4:
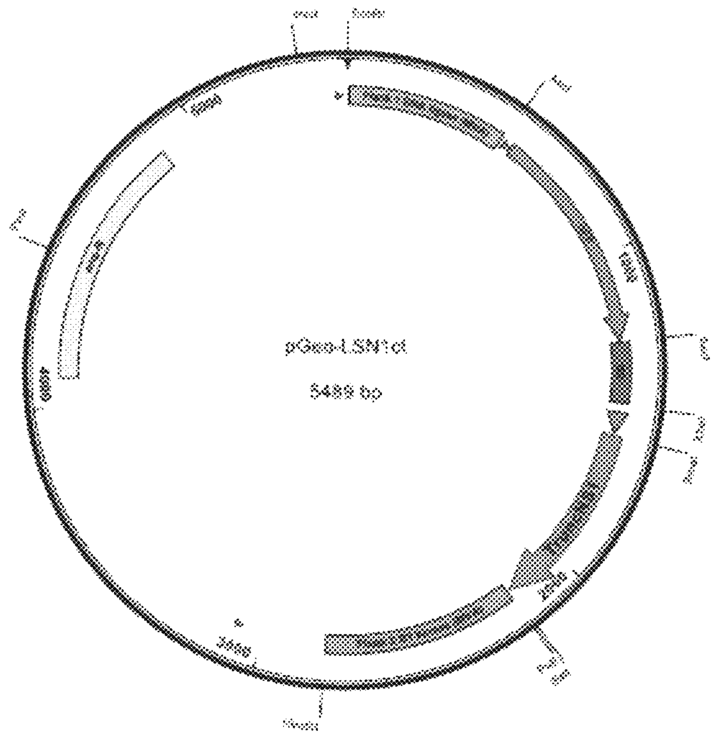

FIG. 4 is a schematic for the shuttle vector for flavivirus truncated NS1.

The ampicillin resistance marker, allowing the vector to replicate in bacteria, is illustrated with a block labeled "amp-R." The two flanking sequences, allowing the vector to recombine with the MVA genome, are illustrated with blocks labeled "Flank 1" and "Flank 2." The green fluorescent protein (GFP) selection marker, allowing the selection of recombinant MVAs, is illustrated with an arrow labeled "GFP." The block labeled "DR" illustrates the location of a sequence homologous to part of Flank 1 of the MVA sequence. DR enables removal of the GFP sequence from the MVA vector after insertion of NS1 into the MVA genome. The modified HS (mHS) promoter, which enables transcription of the inserted heterologous gene, is illustrated with a triangle between the DR and NS1 elements. The flavivirus TruncNS1 gene is illustrated with an arrow labeled "TruncNS1."

Figure 5:
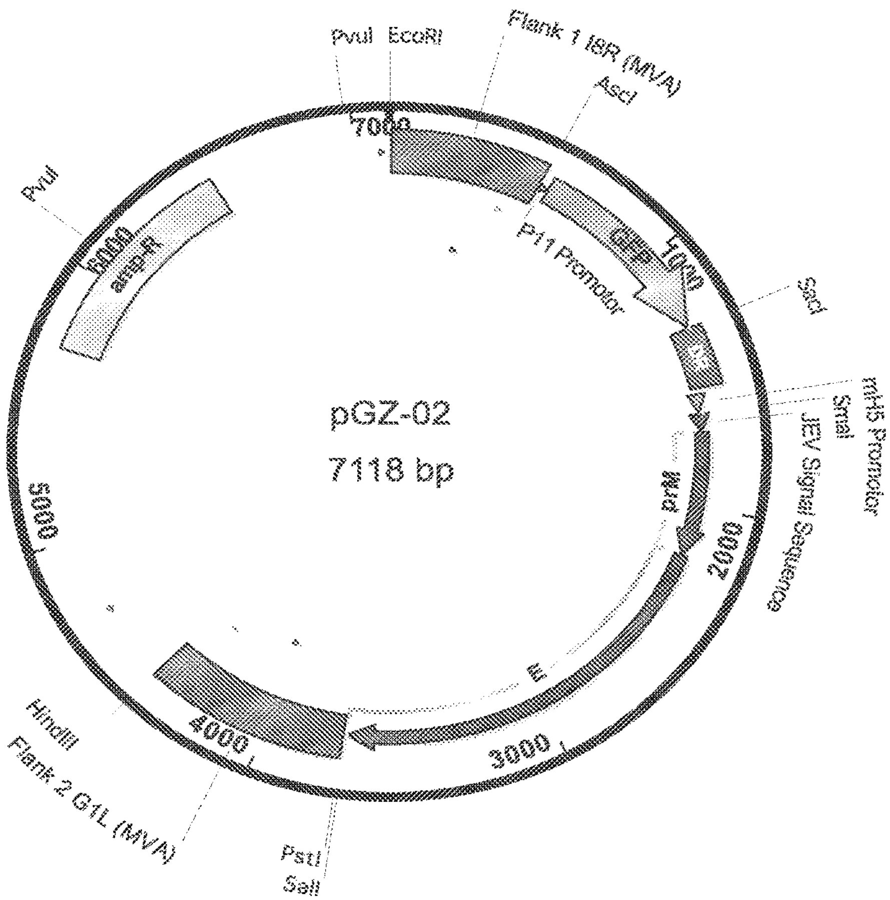

FIG. 5 is a schematic for the flavivirus PCR substrate plasmid pGZ-02.

The ampicillin resistance marker, allowing the vector to replicate in bacteria, is illustrated with a block labeled "amp-R." The two flanking sequences, allowing the vector to recombine with the MVA genome, are illustrated with blocks labeled "Flank 1" and "Flank 2." The green fluorescent protein (GFP) selection marker, allowing the selection of recombinant MVAs, is illustrated with an arrow labeled "GFP." The block labeled "DR" illustrates the location of a sequence homologous to part of Flank 1 of the MVA sequence. DR enables removal of the GFP sequence from the MVA vector after insertion of NS1 into the MVA genome. The modified HS (mHS) promoter, which enables transcription of the inserted heterologous gene, is illustrated with a triangle between the DR and NS1 elements. The flavivirus prM-E gene is illustrated with an arrow labeled "prM" and "E".

Figure 6:
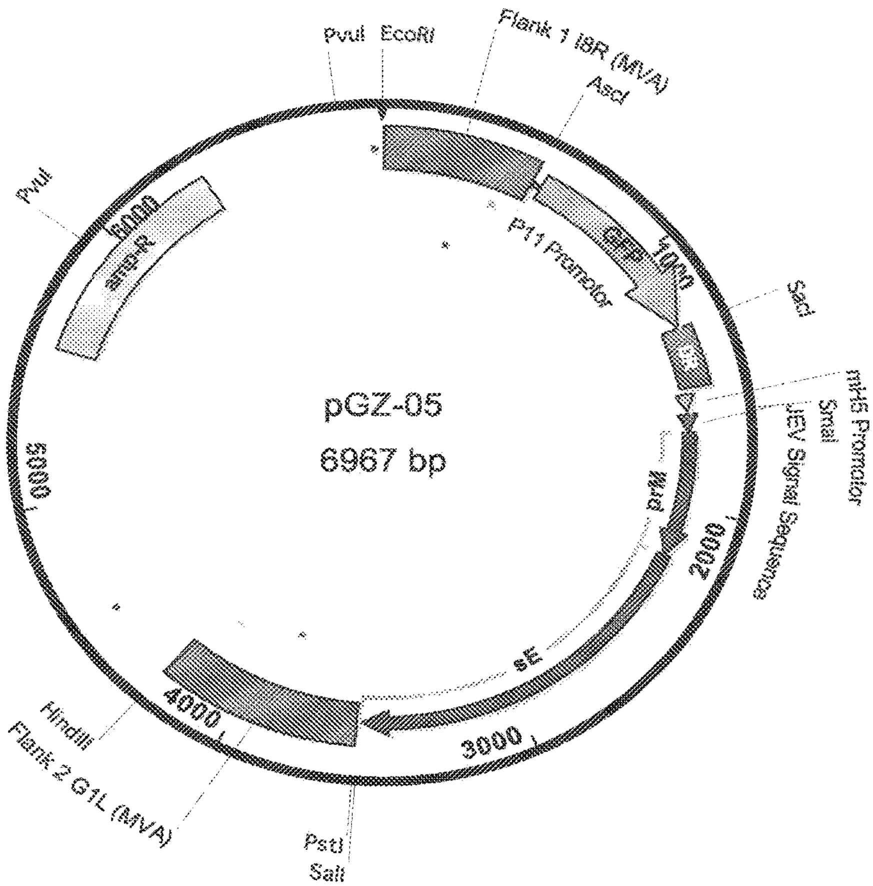

FIG. 6 is a schematic for the flavivirus vector pGZ-0S.

The ampicillin resistance marker, allowing the vector to replicate in bacteria, is illustrated with a block labeled "amp-R." The two flanking sequences, allowing the vector to recombine with the MVA genome, are illustrated with blocks labeled "Flank 1" and "Flank 2." The green fluorescent protein (GFP) selection marker, allowing the selection of recombinant MVAs, is illustrated with an arrow labeled "GFP." The block labeled "DR" illustrates the location of a sequence homologous to part of Flank 1 of the MVA sequence. DR enables removal of the GFP sequence from the MVA vector after insertion of NS1 into the MVA genome. The modified HS (mHS) promoter, which enables transcription of the inserted heterologous gene, is illustrated with a triangle between the DR and NS1 elements. The flavivirus prM and soluble E (sE) genes are illustrated with arrows labeled "prM" and "sE".

Figure 7:
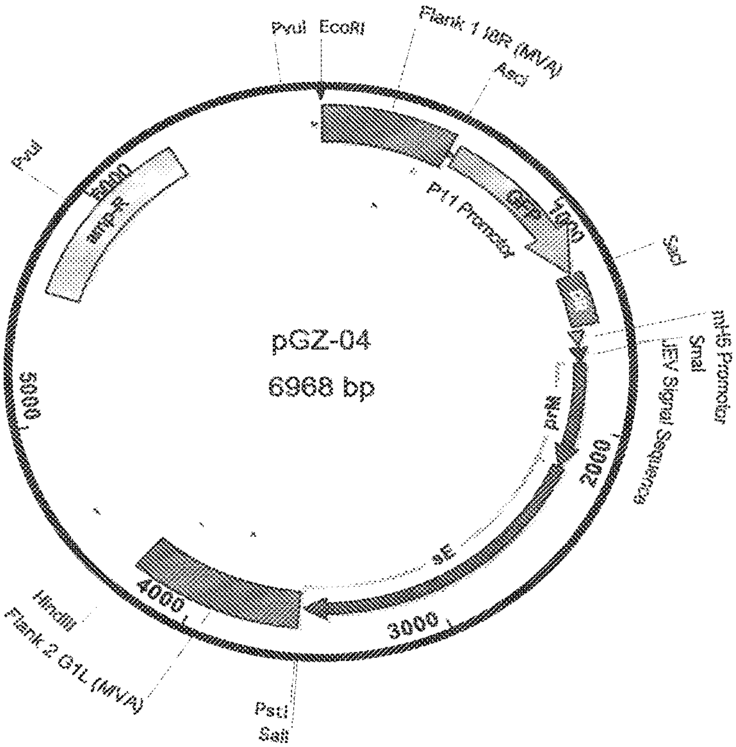

FIG. 7 is a schematic for the flavivirus vector pGZ-04.

The ampicillin resistance marker, allowing the vector to replicate in bacteria, is illustrated with a block labeled "amp-R." The two flanking sequences, allowing the vector to recombine with the MVA genome, are illustrated with blocks labeled "Flank 1" and "Flank 2." The green fluorescent protein (GFP) selection marker, allowing the selection of recombinant MVAs, is illustrated with an arrow labeled "GFP." The block labeled "DR" illustrates the location of a sequence homologous to part of Flank 1 of the MVA sequence. DR enables removal of the GFP sequence from the MVA vector after insertion of NS1 into the MVA genome. The modified HS (mHS) promoter, which enables transcription of the inserted heterologous gene, is illustrated with a triangle between the DR and NS1 elements. The flavivirus prM and soluble E (sE) genes are illustrated with arrows labeled "prM" and "sE".

FIG. 8 provides a figure showing a Western blot showing expression of the Full-length ZIKV E and NS1 Proteins.

Figure 9:
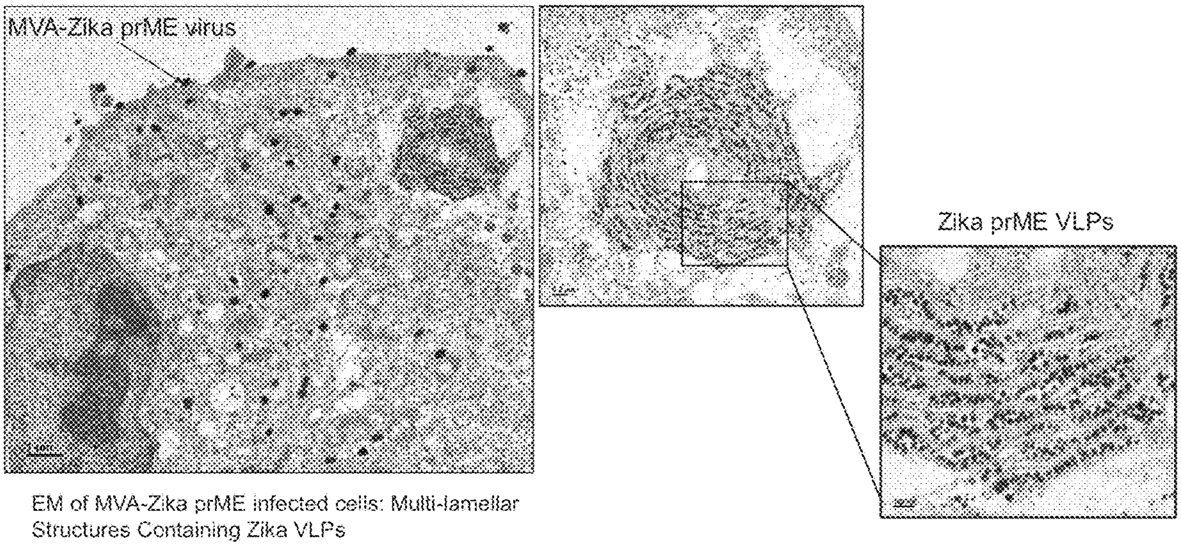

FIG. 9 provides a figure showing electron micrographs of MVA-Zika prME VLP infected cells.

Figure 10:
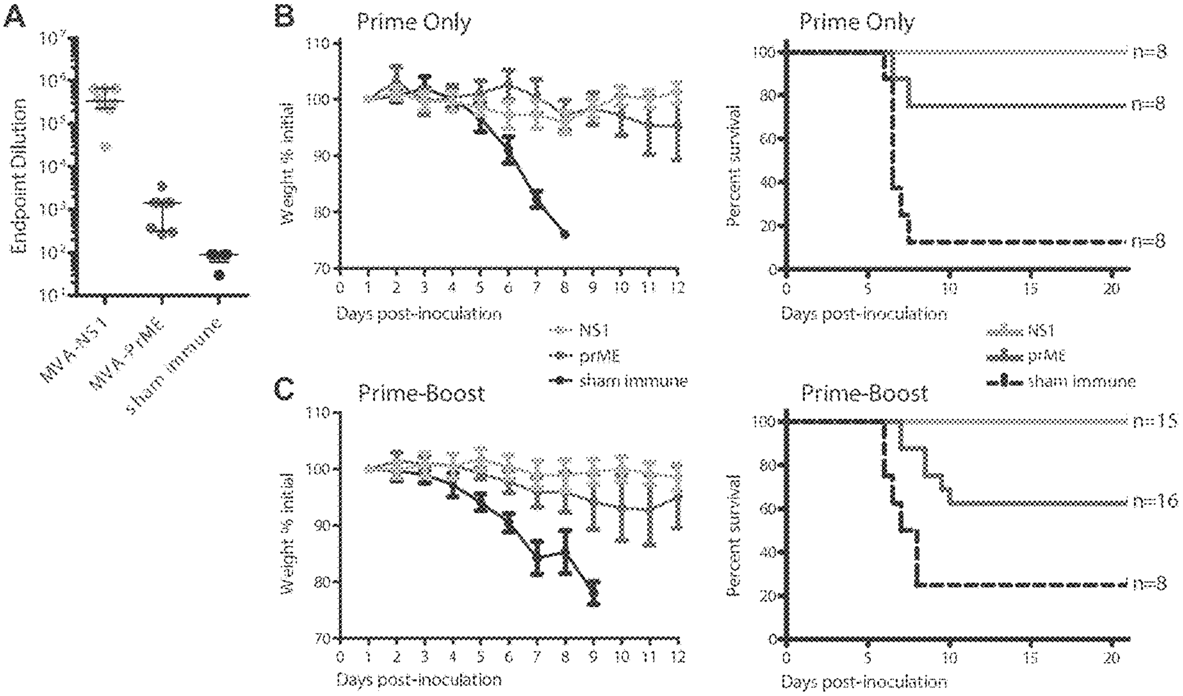

FIG. 10 provides a figure showing the immunogencity and survival of MVA-ZIKV-immunized mice. (A) Ag-specific Abs are evident by ELISA 14 days after boosting.

(B-C) Mice were challenged IC with $10^5$ pfu ZIKV (MR766) 28 days after vaccination. Mice immunized by Prime Only (B) or Prime-Boost (C) regimen maintained weight (left) and were rescued from death (right).

DETAILED DESCRIPTION OF THE INVENTION

Compositions and methods are provided to produce an immune response to a flavivirus, such as a *Zika virus*, in a subject in need thereof. The compositions and methods of the present invention can be used to prevent infection in an unexposed person or to treat disease in a subject exposed to a flavivirus who is not yet symptomatic or has minimal symptoms. In one embodiment, treatment limits an infection and/or the severity of disease.

Ideal immunogenic compositions or vaccines are safe, effective, and provide sufficient scope of protection and longevity. However, compositions having fewer than all of these characteristics may still be useful in preventing viral infection or limiting symptoms or disease progression in an exposed subject treated prior to the development of symptoms. In one embodiment the present invention provides a vaccine that permits at least partial, if not complete, protection after a single immunization.

In exemplary embodiments, the immune responses are long-lasting and durable so that repeated boosters are not required, but in one embodiment, one or more administrations of the compositions provided herein are provided to boost the initial primed immune response.

I. Definitions

Where a term is provided in the singular, the inventors also contemplate aspects of the invention described by the plural of that term. As used in this specification and in the appended claims, the singular forms “a”, “an” and “the” include plural references unless the context clearly dictates otherwise, e.g., “a peptide” includes a plurality of peptides. Thus, for example, a reference to “a method” includes one or more methods, and/or steps of the type described herein and/or which will become apparent to those persons skilled in the art upon reading this disclosure.

The term “antigen” refers to a substance or molecule, such as a protein, or fragment thereof, that is capable of inducing an immune response.

The term “binding antibody” or “bAb” refers to an antibody which either is purified from, or is present in, a body fluid (e.g., serum or a mucosal secretion) and which recognizes a specific antigen. As used herein, the antibody can be a single antibody or a plurality of antibodies. Binding antibodies comprise neutralizing and non-neutralizing antibodies.

The term “cell-mediated immune response” refers to the immunological defense provided by lymphocytes, such as the defense provided by sensitized T cell lymphocytes when they directly lyse cells expressing foreign antigens and secrete cytokines (e.g., IFN-gamma.), which can modulate macrophage and natural killer (NK) cell effector functions and augment T cell expansion and differentiation. The cellular immune response is the $2^{nd}$ branch of the adaptive immune response.

The term “conservative amino acid substitution” refers to substitution of a native amino acid residue with a non-native residue such that there is little or no effect on the size, polarity, charge, hydrophobicity, or hydrophilicity of the amino acid residue at that position, and without resulting in substantially altered immunogenicity. For example, these may be substitutions within the following groups: valine, glycine; glycine, alanine; valine, isoleucine, leucine; aspartic acid, glutamic acid; asparagine, glutamine; serine, threonine; lysine, arginine; and phenylalanine, tyrosine. Conservative amino acid modifications to the sequence of a polypeptide (and the corresponding modifications to the encoding nucleotides) may produce polypeptides having functional and chemical characteristics similar to those of a parental polypeptide.

The term “deletion” in the context of a polypeptide or protein refers to removal of codons for one or more amino acid residues from the polypeptide or protein sequence. The term deletion in the context of a nucleic acid refers to removal of one or more bases from a nucleic acid sequence.

As used herein, the term “E” refers to the flavivirus E protein or the gene or transcript encoding the flavivirus E protein.

The terms “gene”, “polynucleotide”, “nucleotide” and “nucleic acid” are used interchangeably herein.

The term “flavivirus” refers collectively to members of the Flaviridae family of single stranded(−) RNA viruses including West Nile virus, dengue virus, tick-borne encephalitis virus, yellow fever virus, and Zika viruses.

The term “fragment” in the context of a proteinaceous agent refers to a peptide or polypeptide comprising an amino acid sequence of at least 2 contiguous amino acid residues, at least 5 contiguous amino acid residues, at least 10 contiguous amino acid residues, at least 15 contiguous amino acid residues, at least 20 contiguous amino acid residues, at least 25 contiguous amino acid residues, at least 40 contiguous amino acid residues, at least 50 contiguous amino acid residues, at least 60 contiguous amino residues, at least 70 contiguous amino acid residues, at least 80 contiguous amino acid residues, at least 90 contiguous amino acid residues, at least 100 contiguous amino acid residues, at least 125 contiguous amino acid residues, at least 150 contiguous amino acid residues, at least 175 contiguous amino acid residues, at least 200 contiguous amino acid residues, or at least 250 contiguous amino acid residues of the amino acid sequence of a peptide, polypeptide or protein. In one embodiment, a fragment of a full-length protein retains activity of the full-length protein. In another embodiment, the fragment of the full-length protein does not retain the activity of the full-length protein.

The term “fragment” in the context of a nucleic acid refers to a nucleic acid comprising an nucleic acid sequence of at least 2 contiguous nucleotides, at least 5 contiguous nucleotides, at least 10 contiguous nucleotides, at least 15 contiguous nucleotides, at least 20 contiguous nucleotides, at least 25 contiguous nucleotides, at least 30 contiguous nucleotides, at least 35 contiguous nucleotides, at least 40 contiguous nucleotides, at least 50 contiguous nucleotides, at least 60 contiguous nucleotides, at least 70 contiguous nucleotides, at least contiguous 80 nucleotides, at least 90 contiguous nucleotides, at least 100 contiguous nucleotides, at least 125 contiguous nucleotides, at least 150 contiguous nucleotides, at least 175 contiguous nucleotides, at least 200 contiguous nucleotides, at least 250 contiguous nucleotides, at least 300 contiguous nucleotides, at least 350 contiguous nucleotides, or at least 380 contiguous nucleotides of the nucleic acid sequence encoding a peptide, polypeptide or protein. In a preferred embodiment, a fragment of a nucleic acid encodes a peptide or polypeptide that retains activity of the full-length protein. In another embodiment, the fragment encodes a peptide or polypeptide that of the full-length protein does not retain the activity of the full-length protein.

As used herein, the phrase “heterologous sequence” refers to any nucleic acid, protein, polypeptide or peptide sequence which is not normally associated in nature with another nucleic acid or protein, polypeptide or peptide sequence of interest.

As used herein, the phrase “heterologous gene insert” refers to any nucleic acid sequence that has been, or is to be inserted into the recombinant vectors described herein. The heterologous gene insert may refer to only the gene product encoding sequence or may refer to a sequence comprising a promoter, a gene product encoding sequence (such as GP, VP or Z), and any regulatory sequences associated or operably linked therewith.

The term “homopolymer stretch” refers to a sequence comprising at least four of the same nucleotides uninterrupted by any other nucleotide, e.g., GGGG or TTTTTTT.

The term “humeral immune response” refers to the stimulation of Ab production. Humeral immune response also refers to the accessory proteins and events that accompany antibody production, including T helper cell activation and cytokine production, affinity maturation, and memory cell generation. The humeral immune response is one of two branches of the adaptive immune response.

The term “humeral immunity” refers to the immunological defense provided by antibody, such as neutralizing Ab that can directly block infection; or, binding Ab that identifies a virus or infected cell for killing by such innate immune responses as complement (C')-mediated lysis, phagocytosis, and natural killer cells.

The term “immune” or “immunity” refers to protection from disease (e.g., preventing or attenuating (e.g., suppression) of a sign, symptom or condition of the disease) upon exposure to a pathogen (e.g., a virus) capable of causing the disease.

The term "immune response" refers to any response to an antigen or antigenic determinant by the immune system of a subject (e.g., a human). Exemplary immune responses include humeral immune responses (e.g., production of antigen-specific antibodies) and cell-mediated immune responses (e.g., production of antigen-specific T cells).

The term "improved therapeutic outcome" relative to a subject diagnosed as infected with a particular virus (e.g., a flavivirus) refers to a slowing or diminution in the growth of virus, or viral load, or detectable symptoms associated with infection by that particular virus; or a reduction in the ability of the infected subject to transmit the infection to another, uninfected subject.

The term "inducing an immune response" means eliciting a humeral response (e.g., the production of antibodies) or a cellular response (e.g., the activation of T cells) directed against a virus (e.g., zika virus) in a subject to which the composition (e.g., a vaccine) has been administered.

The term "insertion" in the context of a polypeptide or protein refers to the addition of one or more non-native amino acid residues in the polypeptide or protein sequence. Typically, no more than about from 1 to 6 residues (e.g. 1 to 4 residues) are inserted at any one site within the polypeptide or protein molecule.

The term "modified vaccinia Ankara," "modified vaccinia ankara," "Modified Vaccinia Ankara," or "MVA" refers to a highly attenuated strain of vaccinia virus developed by Dr. Anton Mayr by serial passage on chick embryo fibroblast cells; or variants or derivatives thereof. MVA is reviewed in (Mayr, A. et al. 1975 Infection 3:6-14; Swiss Patent No. 568,392).

The term "neutralizing antibody" or "NAb" refers to an antibody which is either purified from, or is present in, a body fluid (e.g., serum or a mucosal secretion) and which recognizes a specific antigen and inhibits the effect(s) of the antigen in the subject (e.g., a human). As used herein, the antibody can be a single antibody or a plurality of antibodies.

The term "non-neutralizing antibody" or "nnAb" refers to a binding antibody that is not a neutralizing antibody.

As used herein, the term "NS" refers to the flavivirus nonstructural protein or the gene or transcript encoding the flavivirus nonstructural protein. There are 7 nonstructural proteins in flavivirus denoted NS1, NS2a, NS2b, NS3, NS4a, NS4b, and NSS.

The term "operably linked", when used with reference to a promoter, refers to a configuration in which the promoter is placed at an appropriate position relative to the coding sequence of a polynucleotide such that the promoter directs expression of the coding sequence. As used herein, the term "PrM" refers to the flavivirus premembrane protein or the gene or transcript encoding the flavivirus premembrane protein.

The term "prevent", "preventing" and "prevention" refers to the inhibition of the development or onset of a condition (e.g., a flavivirus infection or a condition associated therewith), or the prevention of the recurrence, onset, or development of one or more symptoms of a condition in a subject resulting from the administration of a therapy or the administration of a combination of therapies.

The term "prophylactically effective amount" refers to the amount of a composition (e.g., the recombinant MVA vector or pharmaceutical composition) which is sufficient to result in the prevention of the development, recurrence, or onset of a condition or a symptom thereof (e.g., a flavivirus infection or a condition or symptom associated therewith) or to enhance or improve the prophylactic effect(s) of another therapy.

The term "recombinant" means a polynucleotide of semi-synthetic, or synthetic origin that either does not occur in nature or is linked to another polynucleotide in an arrangement not found in nature.

The term "recombinant," with respect to a viral vector, means a vector (e.g., a viral genome) that has been manipulated in vitro (e.g., using recombinant nucleic acid techniques) to express heterologous viral nucleic acid sequences.

The term "regulatory sequence" "regulatory sequences" refers collectively to promoter sequences, polyadenylation signals, transcription termination sequences, upstream regulatory domains, origins of replication, internal ribosome entry sites ("IRES"), enhancers, and the like, which collectively provide for the transcription and translation of a coding sequence. Not all of these control sequences need always be present so long as the selected gene is capable of being transcribed and translated.

The term "shuttle vector" refers to a genetic vector (e.g., a DNA plasmid) that is useful for transferring genetic material from one host system into another. A shuttle vector can replicate alone (without the presence of any other vector) in at least one host (e.g., *E. coli*). In the context of MVA vector construction, shuttle vectors are usually DNA plasmids that can be manipulated in *E. coli* and then introduced into cultured cells infected with MVA vectors, resulting in the generation of new recombinant MVA vectors.

The term "silent mutation" means a change in a nucleotide sequence that does not cause a change in the primary structure of the protein encoded by the nucleotide sequence, e.g., a change from AAA (encoding lysine) to AAG (also encoding lysine).

The term "subject" is means any mammal, including but not limited to, humans, domestic and farm animals, and zoo, sports, or pet animals, such as dogs, horses, cats, cows, rats, mice, guinea pigs and the like.

The term "surrogate endpoint" means a clinical measurement other than a measurement of clinical benefit that is used as a substitute for a measurement of clinical benefit.

The term "surrogate marker" means a laboratory measurement or physical sign that is used in a clinical or animal trial as a substitute for a clinically meaningful endpoint that is a direct measure of how a subject feels, functions, or survives and is expected to predict the effect of the therapy (Katz, R., NeuroRx 1:189-195 (2004); New drug, antibiotic, and biological drug product regulations; accelerated approval-FDA. Final rule. Fed Regist 57: 58942-58960, 1992.)

The term "surrogate marker for protection" means a surrogate marker that is used in a clinical or animal trial as a substitute for the clinically meaningful endpoint of prevention of flavivirus infection.

The term "synonymous codon" refers to the use of a codon with a different nucleic acid sequence to encode the same amino acid, e.g., AAA and AAG (both of which encode lysine). Codon optimization changes the codons for a protein to the synonymous codons that are most frequently used by a vector or a host cell.

The term "therapeutically effective amount" means the amount of the composition (e.g., the recombinant MVA vector or pharmaceutical composition) that, when administered to a mammal for treating an infection, is sufficient to effect treatment for the infection.

The term "treating" or "treat" refer to the eradication or control of a flavivirus, a reduction in the titer of the flavivirus, a reduction in the numbers of the flavivirus, the reduction or amelioration of the progression, severity, and/or duration of a condition or one or more symptoms caused by the flavivirus resulting from the administration of one or more therapies, or the reduction or elimination of the subject's ability to transmit the infection to another, uninfected subject.

The term "vaccine" means material used to provoke an immune response and confer immunity after administration of the material to a subject. Such immunity may include a cellular or humeral immune response that occurs when the subject is exposed to the immunogen after vaccine administration.

The term "vaccine insert" refers to a nucleic acid sequence encoding a heterologous sequence that is operably linked to a promoter for expression when inserted into a recombinant vector. The heterologous sequence may encode a PrM-E or nonstructural protein described here.

The term "viral infection" means an infection by a viral pathogen (e.g., a member of genus *Flavivirus*) wherein there is clinical evidence of the infection based on symptoms or based on the demonstration of the presence of the viral pathogen in a biological sample from the subject.

The term "virus-like particles" or "VLP" refers to a structure which resembles the native virus antigenically and morphologically.

The term "*Zika virus*" which is synonymous with "zikavirus" and "ZIKV" refers to a member of the flavivirus family flaviviridae. *Zika virus* is enveloped and icosahedral and has a non-segmented, single-stranded, positive-sense RNA genome.

11. Flaviviruses

The compositions of the present invention are useful for inducing an immune response to a flavivirus.

*Flavivirus* is a genus of viruses in the family Flaviviridae. This genus includes the West Nile virus, dengue virus, tick-borne encephalitis virus, yellow fever virus, *Zika virus* and several other viruses which may cause encephalitis (Shi, P-Y (editor) (2012). Molecular Virology and Control of Flaviviruses. Caister Academic Press).

Flaviviruses share several common aspects: common size (40-65 nm), symmetry (enveloped, icosahedral nucleocapsid), nucleic acid (positive-sense, single-stranded RNA around 10,000-11,000 bases), and appearance in the electron microscope. Like all flaviviruses, ZIKV is a single-stranded RNA virus with a positive-polarity RNA genome of approximately 11 kb. Both termini of the genomic contain sequences that do not encode viral proteins, known as the 5' and the 3' untranslated region. The encoded polyprotein is translated and co- and posttranslationally processed by viral and cellular proteases into three structural (capsid [C], premembrane [prM] or membrane [M], and envelope [E]) and seven nonstructural (NS1, NS2a, NS2b, NS3, NS4a, NS4b, and NS5) proteins.

Zika Virus Species and Sequences

The term *Zika virus* (ZIKV) refers to a genus within the family *Flavivirus*. Like other Flaviviruses, species within the *Zika virus* genus consist of a single strand of positive sense RNA that is approximately 11 kb in length with 2 flanking non-coding regions (5' and 3' NCR) and a single long open reading frame encoding a polyprotein: 5'-C-prM-E-NS1-NS2A-NS2B-NS3-NS4A-NS4B-NS5-3', that is cleaved into capsid (C), precursor of membrane (prM), envelope (E) and seven non-structural proteins (NS). The E protein (::::::53 kDa) is the major virion surface protein and is involved in various aspects of the viral cycle, mediating binding and membrane fusion. The 3'NCR of the ZIKV genome contains about 428 nucleotides, including 27 folding patterns that may be involved in the recognition by cellular or viral factors, translation, genome stabilization, RNA packaging, or cyclization.

Zika fever is a mosquito-borne illness caused by a flavivirus. Human infections with ZIKVcan cause fever, malaise and cutaneous rash. Despite several reports since 1947, when it was first isolated at Zika forest in Uganda, molecular evolution of ZIKV as an emerging agent remains poorly understood. Moreover, despite several ZIKV reports from Africa and Asia, few human cases were notified until 2007 when an epidemic took place in Micronesia. In West Africa, surveillance programs have reported periodic circulation of the virus since 1968.

Using current methodology, *Zika virus* is detectable in blood only after onset of symptoms, which accompany the rise in circulating virus. It may take up to three days after symptoms start for the virus to reach detectable levels. Laboratory tests used in diagnosis include, for example, antigen-capture enzyme-linked immunosorbent assay (ELISA) testing, IgM ELISA, polymerase chain reaction (PCR), virus isolation, and—later in the course of infection or recovery—detection of IgM and IgG antibodies.

No vaccine or therapeutic has been approved by the FDA for *Zika virus*, for either prophylactic or therapeutic use.

III. Recombinant Viral Vectors

In one aspect, the present invention is a recombinant viral vector comprising one or more genes of a flavivirus virus, such as *Zika virus*. In certain embodiments, the recombinant viral vector is a vaccinia viral vector, and more particularly, an MVA vector, comprising one or more genes of a flavivirus, such as *Zika virus*.

Vaccinia viruses have also been used to engineer viral vectors for recombinant gene expression and for the potential use as recombinant live vaccines (Mackett, M. et al 1982 PNAS USA 79:7415-7419; Smith, G. L. et al. 1984 Biotech Genet Engin Rev 2:383-407). This entails DNA sequences (genes) which code for foreign antigens being introduced, with the aid of DNA recombination techniques, into the genome of the vaccinia viruses. If the gene is integrated at a site in the viral DNA which is non-essential for the life cycle of the virus, it is possible for the newly produced recombinant vaccinia virus to be infectious, that is to say able to infect foreign cells and thus to express the integrated DNA sequence (EP Patent Applications No. 83,286 and No. 110,385). The recombinant vaccinia viruses prepared in this way can be used, on the one hand, as live vaccines for the prophylaxis of infectious diseases, on the other hand, for the preparation of heterologous proteins in eukaryotic cells.

Several such strains of vaccinia virus have been developed to avoid undesired side effects of smallpox vaccination. Thus, a modified vaccinia Ankara (MVA) has been generated by long-term serial passages of the Ankara strain of vaccinia virus (CVA) on chicken embryo fibroblasts (for review see Mayr, A. et al. 1975 Infection 3:6-14; Swiss Patent No. 568,392). The MVA virus is publicly available from American Type Culture Collection as ATCC No.: VR-1508. MVA is distinguished by its great attenuation, as demonstrated by diminished virulence and reduced ability to replicate in primate cells, while maintaining good immunogenicity. The MVA virus has been analyzed to determine alterations in the genome relative to the parental CVA strain. Six major deletions of genomic DNA (deletion I, II, III, IV, V, and VI) totaling 31,000 base pairs have been identified (Meyer, H. et al. 1991 J Gen Virol 72:1031-1038). The resulting MVA virus became severely host cell restricted to avian cells.

Furthermore, MVA is characterized by its extreme attenuation. When tested in a variety of animal models, MVA was proven to be avirulent even in immunosuppressed animals. More importantly, the excellent properties of the MVA strain have been demonstrated in extensive clinical trials (Mayr A. et al. 1978 Zentralbl Bakteriol [B] 167:375-390; Stickl et al. 1974 Dtsch Med Wschr 99:2386-2392). During these studies in over 120,000 humans, including high-risk patients, no side effects were associated with the use of MVA vaccine.

MVA replication in human cells was found to be blocked late in infection preventing the assembly to mature infectious virions. Nevertheless, MVA was able to express viral and recombinant genes at high levels even in non-permissive cells and was proposed to serve as an efficient and exceptionally safe gene expression vector (Sutter, G. and Moss, B. 1992 PNAS USA 89:10847-10851). Additionally, novel vaccinia vector vaccines were established based on MVA having foreign DNA sequences inserted at the site of deletion III within the MVA genome (Sutter, G. et al. 1994 Vaccine 12:1032-1040).

Recombinant MVA vaccinia viruses can be prepared as set out hereinafter. A DNA-construct which contains a DNA-sequence which codes for a foreign polypeptide flanked by MVA DNA sequences adjacent to a predetermined insertion site (e.g. between two conserved essential MVA genes such as I8R/G1L; in restructured and modified deletion III; or at other non-essential sites within the MVA genome) is introduced into cells infected with MVA, to allow homologous recombination. Once the DNA-construct has been introduced into the eukaryotic cell and the foreign DNA has recombined with the viral DNA, it is possible to isolate the desired recombinant vaccinia virus in a manner known per se, preferably with the aid of a marker. The DNA-construct to be inserted can be linear or circular. A plasmid or polymerase chain reaction product is preferred. Such methods of making recombinant MVA vectors are described in PCT publication WO/2006/026667 incorporated by reference herein. The DNA-construct contains sequences flanking the left and the right side of a naturally occurring deletion. The foreign DNA sequence is inserted between the sequences flanking the naturally occurring deletion. For the expression of a DNA sequence or gene, it is necessary for regulatory sequences, which are required for the transcription of the gene, to be present on the DNA. Such regulatory sequences (called promoters) are known to those skilled in the art, and include for example those of the vaccinia 11 kDa gene as are described in EP-A-198,328, and those of the 7.5 kDa gene (EP-A-110,385). The DNA-construct can be introduced into the MVA infected cells by transfection, for example by means of calcium phosphate precipitation (Graham et al. 1973 Virol 52:456-467; Wigler et al. 1979 Cell 16:777-785), by means of electroporation (Neumann et al. 1982 EMBO J. 1:841-845), by microinjection (Graessmann et al. 1983 Meth Enzymol 101:482-492), by means of liposomes (Straubinger et al. 1983 Meth Enzymol 101:512-527), by means of spheroplasts (Schaffher 1980 PNAS USA 77:2163-2167) or by other methods known to those skilled in the art.

The MVA vectors described and tested herein were unexpectedly found to be effective after a single prime or a homologous prime/boost regimen. Other MVA vector designs require a heterologous prime/boost regimen, while still other published studies have been unable to induce effective immune responses with MVA vectors. Conversely, the present MVA vector design and methods of manufacture are useful in producing effective MVA vaccine vectors for eliciting effective T-cell and antibody immune responses. Furthermore, the utility of an MVA vector capable of eliciting effective immune responses and antibody production after a single homologous prime boost is significant for considerations such as use, commercialization and transport of materials especially to affected third world locations.

In one embodiment, the present invention is a recombinant viral vector (e.g., an MVA vector) comprising one or more heterologous gene inserts of a flavivirus (e.g., a *Zika virus*). The viral vector (e.g., an MVA vector) may be constructed using conventional techniques known to one of skill in the art. The one or more heterologous gene inserts encode a polypeptide having desired immunogenicity, i.e., a polypeptide that can induce an immune reaction, cellular immunity and/or humeral immunity, in vivo by administration thereof. The gene region of the vector (e.g., an MVA vector) where the gene encoding a polypeptide having immunogenicity is introduced is flanked by regions that are indispensable. In the introduction of a gene encoding a polypeptide having immunogenicity, an appropriate promoter may be operatively linked upstream of the gene encoding a polypeptide having desired immunogenicity.

The one or more genes may be selected from any species of flavivirus. In one embodiment, the one more genes are selected from a *Zika virus* species. In exemplary embodiments, the gene encodes a polypeptide or protein capable of inducing an immune response in the subject to which it is administered, and more particularly, an immune response capable of providing a protective and/or therapeutic benefit to the subject. In one embodiment, the one or more genes encode the virus premembrane protein (PrM), the E protein (E), the or one or more nonstructural proteins (e.g. NS1, NS2a, NS2b, NS3, NS4a, NS4b, and NSS)). The heterologous gene inserts are inserted into one or more deletion sites of the vector under the control of promoters compatible with poxvirus expression systems.

In one embodiment, the deletion III site is restructured and modified to remove non-essential flanking sequences.

In exemplary embodiments, the vaccine is constructed to express an *Zika virus* premembrane-E protein (PrM-E), which is inserted between two conserved essential MVA genes (I8R and G1L) using shuttle vector pGeo-PrM-E; and to express *Zika virus* NS1, which is inserted into deletion III using shuttle vector pGeo-NS1. pGeo-PrM-E and pGeo-NS1 are constructed with an ampicillin resistance marker, allowing the vector to replicate in bacteria; with two flanking sequences, allowing the vector to recombine with a specific location in the MVA genome; with a green fluorescent protein (GFP) selection marker, allowing the selection of recombinant MVAs; with a sequence homologous to part of Flank 1 of the MVA sequence, enabling removal of the GFP sequence from the MVA vector after insertion of NS1 into the MVA genome; with a modified HS (mHS) promoter, which enables transcription of the inserted heterologous gene insert; and with a flavivirus gene. pGeo-PrM-E and pGeo-NS1 differ in that pGeo-PrM-E contains the PrM-E sequence, whereas pGeo-NS1 contains the NS1 sequence; and in that pGeo-PrM-E recombines with sequences of MVA I8R and G1L (two essential genes) and pGeo-NS1 recombines with regions flanking the restructured and modified Deletion III of MVA.

In exemplary embodiments, the present invention provides a recombinant MVA vector comprising a gene encoding the PrM-E gene and a gene encoding NS1, in each case, from a *Zika virus*.

In certain embodiments, the polypeptide, or the nucleic acid sequence encoding the polypeptide, may have a mutation or deletion (e.g., an internal deletion, truncation of the amino- or carboxy-terminus, or a point mutation).

The one or more genes introduced into the recombinant viral vector are under the control of regulatory sequences that direct its expression in a cell.

The nucleic acid material of the viral vector may be encapsulated, e.g., in a lipid membrane or by structural proteins (e.g., capsid proteins), that may include one or more viral polypeptides.

In exemplary embodiments, the present invention is a recombinant viral vector (e.g., a recombinant MVA vector) comprising one or more genes, or one or more polypeptides encoded by the gene or genes, from a *Zika virus*. The *Zika virus* gene may encode a polypeptide or protein capable of inducing an immune response in the subject to which it is administered, and more particularly, an immune response capable of providing a protective and/or therapeutic benefit to the subject, e.g., the *Zika virus* PrM-E. The nucleic acid sequences of *Zika virus* premembrane and E proteins and nonstructural are published and are available from a variety of sources, including, e.g., GenBank and PubMed. Exemplary GenBank references including *Zika virus* sequences include those corresponding to accession numbers KU312312.

In certain embodiments, the one or more genes encodes a polypeptide, or fragment thereof, that is substantially identical (e.g., at least 60%, 65%, 70%, 75%, 80%, 85%, 90%, 95%, 98%, 99%, or even 100% identical) to the selected *Zika virus* PrM-E over at least 20, 25, 30, 35, 40, 45, 50, 55, 60, 65, or 70 contiguous residues of the selected *Zika virus* PrM or E that retain immunogenic activity.

In certain embodiments, the one or more genes encodes a polypeptide, or fragment thereof, that is substantially identical (e.g., at least 60%, 65%, 70%, 75%, 80%, 85%, 90%, 95%, 98%, 99%, or even 100% identical) to the selected *Zika virus* E over at least 20, 25, 30, 35, 40, 45, 50, 55, 60, 65, or 70 contiguous residues of the selected *Zika virus* E that retains immunogenic activity.

In exemplary embodiments, the recombinant viral vector may also include an *Zika virus* PrM-E present on its surface. The *Zika virus* PrM-E may be obtained by any suitable means, including, e.g., application of genetic engineering techniques to a viral source, chemical synthesis techniques, recombinant production, or any combination thereof.

In another embodiments, the present invention is a recombinant MVA vector comprising at least one heterologous gene insert from an *Zika virus*, wherein the gene is selected from the group encoding the premembrane protein (PrM), the E protein (E), the or one or more nonstructural proteins (e.g. NS1, NS2a, NS2b, NS3, NS4a, NS4b, and NS5).

In a particular embodiment, the present invention is a recombinant MVA vector comprising a gene encoding PrM-E and a gene encoding NS1. In another embodiment, the present invention is a recombinant MVA vector comprising genes encoding PrM-E, and NS1. The heterologous gene inserts are inserted into one or more deletion sites of the MVA vector under the control of promoters compatible with poxvirus expression systems.

In one embodiment, the PrM-E is inserted into deletion site I, II, III, IV, V or VI of the MVA vector, and the NS1 is inserted into deletion site I, II, III, IV, V or VI of the MVA vector.

In one embodiment, the PrM-E is inserted between I8R and G1L of the MVA vector, or into restructured and modified deletion III of the MVA vector; and the NS1 is inserted between I8R and G1L of the MVA vector, or into restructured and modified deletion site III of the MVA vector.

In exemplary embodiments, the present invention is a recombinant MVA vector comprising at least one heterologous gene insert (e.g., one or more gene inserts) from a Zika virus which is under the control of regulatory sequences that direct its expression in a cell. The gene may be, for example, under the control of a promoter selected from the group consisting of Pm2H5, Psyn II, or mHS promoters.

In one embodiment, the recombinant MVA vaccine expresses proteins that assemble into virus-like particles (VLPs) comprising the PrM-E and NS1 proteins. While not wanting to be bound by any particular theory, it is believed that the PrM-E is provided to elicit a protective immune response and the NS1 (nonstructural protein) is provided to enable assembly of VLPs and as a target for T cell immune responses, thereby enhancing the protective immune response and providing cross-protection.

One or more genes may be optimized for use in the MVA vector. Optimization includes codon optimization, which employs silent mutations to change selected codons from the native sequences into synonymous codons that are optimally expressed by the host-vector system. Other types of optimization include the use of silent mutations to interrupt homopolymer stretches or transcription terminator motifs. Each of these optimization strategies can improve the stability of the gene, improve the stability of the transcript, or improve the level of protein expression from the gene. In exemplary embodiments, the number of homopolymer stretches in the PrM-E or NS1 sequence is reduced to stabilize the construct. A silent mutation may be provided for anything similar to a vaccinia termination signal.

In exemplary embodiments, optimization of genes may include interrupting homopolymer sequences (2::4 G/C and 2::A/T) by silent mutations, adding a second TAA stop codon, or adding a Vaccinia Transcription Terminator Sequence at the end of the gene such as TTTTTAT.

In exemplary embodiments, the PrM-E and NS1 sequences are codon optimized for expression in MVA using a computer algorithm; PrM-E and NS1 sequences with runs of 2::5 deoxyguanosines, 2::5 deoxycytidines, 2::5 deoxyadenosines, and 2::5 deoxythymidines are interrupted by silent mutation to minimize loss of expression due to frame shift mutations; and the PrM-E sequence is modified through addition of an extra nucleotide to express the transmembrane, rather than the secreted, form of *Zika virus* PrM-E.

The recombinant viral vectors of the present invention may be used alone or in combination. In one embodiment, two different recombinant viral vectors are used in combination, where the difference may refer to the one or more heterologous gene inserts or the other components of the recombinant viral vector or both. In exemplary embodiments, two or more recombinant viral vectors are used in combination in order to protect against infection by all versions of *Flavivirus* in humans.

The present invention also extends to host cells comprising the recombinant viral vector described above, as well as isolated virions prepared from host cells infected with the recombinant viral vector.

IV. Pharmaceutical Composition

The recombinant viral vectors of the present invention are readily formulated as pharmaceutical compositions for veterinary or human use, either alone or in combination. The pharmaceutical composition may comprise a pharmaceutically acceptable diluent, excipient, carrier, or adjuvant.

In one embodiment, the present invention is a vaccine effective to protect and/or treat a *Flavivirus* (e.g., a *Zika virus*) comprising a recombinant MVA vector that expresses at least one *Flavivirus* polypeptide (e.g., a PrM-E) or an immunogenic fragment thereof. The vaccine composition may comprise one or more additional therapeutic agents.

The pharmaceutical composition may comprise 1, 2, 3, 4 or more than 4 different recombinant MVA vectors.

As used herein, the phrase "pharmaceutically acceptable carrier" encompasses any suitable pharmaceutical carrier, such as those suitable for parenteral administration, such as, for example, by intramuscular, intraarticular (in the joints), intravenous, intradermal, intraperitoneal, and subcutaneous routes. Examples of such formulations include aqueous and non-aqueous, isotonic sterile injection solutions, which contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. One exemplary pharmaceutically acceptable carrier is physiological saline.

Other physiologically acceptable diluents, excipients, carriers, or adjuvants and their formulations are known to those skilled in the art.

The compositions utilized in the methods described herein can be administered by a route any suitable method, e.g., parenteral, intramuscular, intraarterial, intravascular, intravenous, intraperitoneal, subcutaneous, dermal, transdermal, ocular, inhalation, buccal, sublingual, perilingual, nasal, topical administration, and oral administration. The preferred method of administration can vary depending on various factors (e.g., the components of the composition being administered and the severity of the condition being treated). Formulations suitable for oral administration may consist of liquid solutions, such as an effective amount of the composition dissolved in a diluent (e.g., water, saline, or PEG-400), capsules, sachets or tablets, each containing a predetermined amount of the vaccine. The pharmaceutical composition may also be an aerosol formulation for inhalation, e.g., to the bronchial passageways. Aerosol formulations may be mixed with pressurized, pharmaceutically acceptable propellants (e.g., dichlorodifluoromethane, propane, or nitrogen).

For the purposes of this invention, pharmaceutical compositions suitable for delivering a therapeutic or biologically active agent can include, e.g., tablets, gelcaps, capsules, pills, powders, granulates, suspensions, emulsions, solutions, gels, hydrogels, oral gels, pastes, eye drops, ointments, creams, plasters, drenches, delivery devices, microneedles, suppositories, enemas, injectables, implants, sprays, or aerosols. Any of these formulations can be prepared by well-known and accepted methods of art. See, for example, Remington: The Science and Practice of Pharmacy (21.sup.st ed.), ed. A. R. Gennaro, Lippincott Williams & Wilkins, 2005, and Encyclopedia of Pharmaceutical Technology, ed. J. Swarbrick, Informa Healthcare, 2006, each of which is hereby incorporated by reference.

The immunogenicity of the composition (e.g., vaccine) may be significantly improved if the composition of the present invention is co-administered with an immunostimulatory agent or adjuvant. Suitable adjuvants well-known to those skilled in the art include, e.g., aluminum phosphate, aluminum hydroxide, QS21, Quil A (and derivatives and components thereof), calcium phosphate, calcium hydroxide, zinc hydroxide, glycolipid analogs, octodecyl esters of an amino acid, muramyl dipeptides, polyphosphazene, lipoproteins, ISCOM-Matrix, DC-Chol, ODA, cytokines, and other adjuvants and derivatives thereof.

Pharmaceutical compositions according to the present invention may be formulated to release the composition immediately upon administration (e.g., targeted delivery) or at any predetermined time period after administration using controlled or extended release formulations. Administration of the pharmaceutical composition in controlled or extended release formulations is useful where the composition, either alone or in combination, has (i) a narrow therapeutic index (e.g., the difference between the plasma concentration leading to harmful side effects or toxic reactions and the plasma concentration leading to a therapeutic effect is small; generally, the therapeutic index, TI, is defined as the ratio of median lethal dose (LDso) to median effective dose (EDso)); (ii) a narrow absorption window in the gastro-intestinal tract; or (iii) a short biological half-life, so that frequent dosing during a day is required in order to sustain a therapeutic level.

Many strategies can be pursued to obtain controlled or extended release in which the rate of release outweighs the rate of metabolism of the pharmaceutical composition. For example, controlled release can be obtained by the appropriate selection of formulation parameters and ingredients, including, e.g., appropriate controlled release compositions and coatings. Suitable formulations are known to those of skill in the art. Examples include single or multiple unit tablet or capsule compositions, oil solutions, suspensions, emulsions, microcapsules, microspheres, nanoparticles, patches, and liposomes.

Formulations suitable for oral administration can consist of (a) liquid solutions, such as an effective amount of the vaccine dissolved in diluents, such as water, saline or PEG 400; (b) capsules, sachets or tablets, each containing a predetermined amount of the vaccine, as liquids, solids, granules or gelatin; (c) suspensions in an appropriate liquid; (d) suitable emulsions; and (e) polysaccharide polymers such as chitins. The vaccine, alone or in combination with other suitable components, may also be made into aerosol formulations to be administered via inhalation, e.g., to the bronchial passageways. Aerosol formulations can be placed into pressurized acceptable propellants, such as dichlorodifluoromethane, propane, nitrogen, and the like.

Suitable formulations for rectal administration include, for example, suppositories, which consist of the vaccine with a suppository base. Suitable suppository bases include natural or synthetic triglycerides or paraffin hydrocarbons. In addition, it is also possible to use gelatin rectal capsules which consist of a combination of the vaccine with a base, including, for example, liquid triglycerides, polyethylene glycols, and paraffin hydrocarbons.

Pharmaceutical compositions comprising any of the nucleic acid molecules encoding flavivirus viral proteins of the present invention are useful to immunize a subject against disease caused by flavivirus infection. Thus, this invention further provides methods of immunizing a subject against disease caused by flavivirus infection, comprising administering to the subject an immunoeffective amount of a pharmaceutical composition of the invention. This subject may be an animal, for example a mammal, such as a primate or preferably a human.

The vaccines of the present invention may also be co-administered with cytokines to further enhance immunogenicity. The cytokines may be administered by methods known to those skilled in the art, e.g., as a nucleic acid molecule in plasmid form or as a protein or fusion protein.

Kits

This invention also provides kits comprising the vaccines of the present invention. For example, kits comprising a vaccine and instructions for use are within the scope of this invention.

V. Method of Use

The compositions of the invention can be used as vaccines for inducing an immune response to a *Flavivirus*, such as a *Zika virus*.

In exemplary embodiments, the present invention provides a method of preventing a *Flavivirus* (e.g., *Zika virus*) infection to a subject in need thereof (e.g., an unexposed subject), comprising administering the composition of the present invention to the subject in a prophylactically effective amount. The result of the method is that the subject is partially or completely immunized against the virus.

In exemplary embodiments, the present invention provides a method of treating a flavivirus (e.g., *Zika virus*) infection in a subject in need thereof (e.g., an exposed subject, such as a subject who has been recently exposed but is not yet symptomatic, or a subject who has been recently exposed and is only mildly symptomatic), comprising administering the composition of the present invention to the subject in a therapeutically effective amount. The result of treatment is a subject that has an improved therapeutic profile.

Typically, the vaccines will be in an admixture and administered simultaneously, but may also be administered separately.

A subject to be treated according to the methods described herein (e.g., a subject infected with, a *Zika virus*) may be one who has been diagnosed by a medical practitioner as having such a condition. Diagnosis may be performed by any suitable means. A subject in whom the development of an infection is being prevented may or may not have received such a diagnosis. One skilled in the art will understand that a subject to be treated according to the present invention may have been identified using standard tests or may have been identified, without examination, as one at high risk due to the presence of one or more risk factors (e.g., exposure to *Zika virus*, etc.).

Prophylactic treatment may be administered, for example, to a subject not yet exposed to or infected by a *Flavivirus* but who is susceptible to, or otherwise at risk of exposure or infection with an a *Flavivirus*.

Therapeutic treatment may be administered, for example, to a subject already exposed to or infected by a *Flavivirus* who is not yet ill, or showing symptoms or infection, suffering from a disorder in order to improve or stabilize the subject's condition (e.g., a patient already infected with a flavivirus). The result is an improved therapeutic profile. In some instances, as compared with an equivalent untreated control, treatment may ameliorate a disorder or a symptom thereof by, e.g., 5%, 10%, 20%, 30%, 40%, 50%, 60%, 70%, 80%, 90%, 95%, or 100% as measured by any standard technique. In some instances, treating can result in the inhibition of viral replication, a decrease in viral titers or viral load, eradication or clearing of the virus.

In other embodiments, treatment may result in amelioration of one or more symptoms of the infection, including any symptom identified above. According to this embodiment, confirmation of treatment can be assessed by detecting an improvement in or the absence of symptoms.

In other embodiments, treatment may result in reduction or elimination of the ability of the subject to transmit the infection to another, uninfected subject. Confirmation of treatment according to this embodiment is generally assessed using the same methods used to determine amelioration of the disorder, but the reduction in viral titer or viral load necessary to prevent transmission may differ from the reduction in viral titer or viral load necessary to ameliorate the disorder.

In one embodiment, the present invention is a method of inducing an immune response in a subject (e.g., a human) by administering to the subject a recombinant viral vector that encodes at least one gene from a *Flavivirus*, such as a *Zika virus*. The immune response may be a cellular immune response, a humeral immune response or a combination thereof. The immune response may be a T-cell response, a B-cell response or an antibody response.

In a particular embodiment, the present invention is a method of inducing an immune response in a subject (e.g., a human) in need thereof by administering to the subject a recombinant viral vector that encodes at least one gene from a *Zika virus*.

The composition may be administered, e.g., by injection (e.g., intramuscular, intraarterial, intravascular, intravenous, intraperitoneal, or subcutaneous).

It will be appreciated that more than one route of administering the vaccines of the present invention may be employed either simultaneously or sequentially (e.g., boosting). In addition, the vaccines of the present invention may be employed in combination with traditional immunization approaches such as employing protein antigens, vaccinia virus and inactivated virus, as vaccines. Thus, in one embodiment, the vaccines of the present invention are administered to a subject (the subject is "primed" with a vaccine of the present invention) and then a traditional vaccine is administered (the subject is "boosted" with a traditional vaccine). In another embodiment, a traditional vaccine is first administered to the subject followed by administration of a vaccine of the present invention. In yet another embodiment, a traditional vaccine and a vaccine of the present invention are co-administered.

It will also be appreciated that single or multiple administrations of the vaccine compositions of the present invention may be carried out. For example, subjects who are particularly susceptible to *Flavivirus* infection may require multiple immunizations to establish and/or maintain protective immune responses. Levels of induced immunity can be monitored by measuring amounts of binding and neutralizing secretory and serum antibodies as well as levels of T cells, and dosages adjusted or vaccinations repeated as necessary to maintain desired levels of protection.

In one embodiment, administration is repeated at least twice, at least 3 times, at least 4 times, at least 5 times, at least 6 times, at least 7 times, at least 8 times, or more than 8 times.

In one embodiment, administration is repeated twice.

In one embodiment, about 2-8, about 4-8, or about 6-8 administrations are provided.

In one embodiment, about 1-4-week, 2-4 week, 3-4 week, 1 week, 2 week, 3 week, 4 week or more than 4 week intervals are provided between administrations.

In one specific embodiment, a 4-week interval is used between 2 administrations.

Dosage

The vaccines are administered in a manner compatible with the dosage formulation, and in such amount, as will be therapeutically effective, immunogenic and protective. The quantity to be administered depends on the subject to be treated, including, for example, the capacity of the immune system of the individual to synthesize antibodies, and, if needed, to produce a cell-mediated immune response. Precise amounts of active ingredient required to be administered depend on the judgment of the practitioner and may be monitored on a patient-by-patient basis. However, suitable dosage ranges are readily determinable by one skilled in the art and generally range from about $5.0\times10^6$ TCIDso to about $5.0\times10^9$ TCIDso. The dosage may also depend, without limitation, on the route of administration, the patient's state of health and weight, and the nature of the formulation.

The pharmaceutical compositions of the invention are administered in such an amount as will be therapeutically effective, immunogenic, and/or protective against a pathogenic species of *Zika virus*. The dosage administered depends on the subject to be treated (e.g., the manner of administration and the age, body weight, capacity of the immune system, and general health of the subject being treated). The composition is administered in an amount to provide a sufficient level of expression that elicits an immune response without undue adverse physiological effects. Preferably, the composition of the invention is a heterologous viral vector that includes one or more polypeptides of the flavivirus (e.g., the *Zika virus* PrM-E protein and NS1 protein), or a nucleic acid molecule encoding one or more genes of the *Flavivirus*, and is administered at a dosage of, e.g., between $1.0\times10^4$ and $9.9\times10^{12}$ $TCID_{50}$ of the viral vector, preferably between $1.0\times10^5$ $TCID_{50}$ and $1.0\times10^{11}$ $TCID_{50}$ pfu, more preferably between $1.0\times10^6$ and $1.0\times10^{10}$ $TCID_{50}$ pfu, or most preferably between $5.0\times10^6$ and $5.0\times10^9$ $TCID_{50}$. The composition may include, e.g., at least $5.0\times10^6$ TCIDso of the viral vector (e.g., $1.0\times10^8$ TCIDso of the viral vector). A physician or researcher can decide the appropriate amount and dosage regimen.

985 The composition of the method may include, e.g., between $1.0\times10^4$ and $9.9\times10^{12}$ TCIDso of the viral vector, preferably between $1.0\times10^5$ TCIDso and $1.0\times10^{11}$ TCIDso pfu, more preferably between $1.0\times10^6$ and $1.0\times10^{10}$ $TCID_{50}$ pfu, or most preferably between $5.0\times10^6$ and $5.0\times10^9$ TCIDso. The composition may include, e.g., at least $5.0\times10^6$ TCIDso of the viral vector (e.g., $1.0\times10^8$ TCIDso of the viral vector). The method may include, e.g., administering the composition to the subject two or more times.

In certain embodiments, pharmaceutical compositions may comprise, for example, at least about 0.1% of an active compound. In other embodiments, an active compound may comprise between about 2% to about 75% of the weight of the unit, or between about 25% to about 60%, for example, and any range derivable therein. However, a suitable dosage range may be, for example, of the order of several hundred micrograms active ingredient per vaccination. In other non-limiting examples, a dose may also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per vaccination, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above. A suitable regime for initial administration and booster administrations (e.g., inoculations) are also variable, but are typified by an initial administration followed by subsequent inoculation(s) or other administration(s).

The invention also features a method of inducing an immune response to flavivirus in a subject (e.g., a human) that includes administering to the subject an effective amount of a recombinant viral vector that encodes at least one gene from the flavivirus (e.g., the *Zika virus* PrM-E protein and NS1 protein). The subject being treated may not have, but rather be at risk of developing, an infection by a flavivirus. Alternatively, the subject may already be infected with a flavivirus. The composition may be administered, e.g., by injection (e.g., intramuscular, intraarterial, intravascular, intravenous, intraperitoneal, or subcutaneous).

The term "effective amount" is meant the amount of a composition administered to improve, inhibit, or ameliorate a condition of a subject, or a symptom of a disorder, in a clinically relevant manner (e.g., improve, inhibit, or ameliorate infection by flavivirus or provide an effective immune response to infection by flavivirus). Any improvement in the subject is considered sufficient to achieve treatment. Preferably, an amount sufficient to treat is an amount that prevents the occurrence or one or more symptoms of flavivirus infection or is an amount that reduces the severity of, or the length of time during which a subject suffers from, one or more symptoms of flavivirus infection (e.g., by at least 10%, 20%, or 30%, more preferably by at least 50%, 60%, or 70%, and most preferably by at least 80%, 90%, 95%, 99%, or more, relative to a control subject that is not treated with a composition of the invention). A sufficient amount of the pharmaceutical composition used to practice the methods described herein (e.g., the treatment of flavivirus infection) varies depending upon the manner of administration and the age, body weight, and general health of the subject being treated. Ultimately, the prescribers or researchers will decide the appropriate amount and dosage.

It is important to note that the value of the present invention may never be demonstrated in terms of actual clinical benefit. Instead, it is likely that the value of the invention will be demonstrated in terms of success against a surrogate marker for protection. For an indication such as flavivirus infection, in which it is impractical or unethical to attempt to measure clinical benefit of an intervention, the FDA's Accelerated Approval process allows approval of a new vaccine based on efficacy against a surrogate endpoint. Therefore, the value of the invention may lie in its ability to induce an immune response that constitutes a surrogate marker for protection.

Similarly, FDA may allow approval of vaccines against flavivirus based on its Animal Rule. In this case, approval is achieved based on efficacy in animals. The value of the invention may lie in its ability to protect relevant animal species against infection with flaviviruses, thus providing adequate evidence to justify its approval.

The composition of the method may include, e.g., between $1.0\times10^4$ and $9.9\times10^{12}$ $TCID_{50}$ of the viral vector, preferably between $1.0\times10^5$ $TCID_{50}$ and $1.0\times10^{11}$ $TCID_{50}$ pfu, more preferably between $1.0\times10^6$ and $1.0\times10^{10}$ $TCID_{50}$ pfu, or most preferably between $5.0\times10^6$ and $5.0\times10^9$ $TCID_{50}$. The composition may include, e.g., at least $5.0\times10^6$ $TCID_{50}$ of the viral vector. The method may include, e.g., administering the composition two or more times.

In some instances it may be desirable to combine the flavivirus vaccines of the present invention with vaccines which induce protective responses to other agents, particularly other viruses. For example, the vaccine compositions of the present invention can be administered simultaneously, separately or sequentially with other genetic immunization vaccines such as those for influenza (Ulmer, J. B. et al., Science 259:1745-1749 (1993); Raz, E. et al., PNAS (USA) 91:9519-9523 (1994)), malaria (Doolan, D. L. et al., J. Exp. Med. 183:1739-1746 (1996); Sedegah, M. et al., PNAS (USA) 91:9866-9870 (1994)), and tuberculosis (Tascon, R. C. et al., Nat. Med. 2:888-892 (1996)).

Administration

As used herein, the term "administering" refers to a method of giving a dosage of a pharmaceutical composition of the invention to a subject. The compositions utilized in the methods described herein can be administered by a route selected from, e.g., parenteral, dermal, transdermal, ocular, inhalation, buccal, sublingual, perilingual, nasal, rectal, topical administration, and oral administration. Parenteral administration includes intravenous, intraperitoneal, subcutaneous, intraarterial, intravascular, and intramuscular administration. The preferred method of administration can vary depending on various factors (e.g., the components of the composition being administered and the severity of the condition being treated).

Administration of the pharmaceutical compositions (e.g., vaccines) of the present invention can be by any of the routes known to one of skill in the art. Administration may be by, e.g., intramuscular injection. The compositions utilized in the methods described herein can also be administered by a route selected from, e.g., parenteral, dermal, transdermal, ocular, inhalation, buccal, sublingual, perilingual, nasal, rectal, topical administration, and oral administration. Parenteral administration includes intravenous, intraperitoneal, subcutaneous, and intramuscular administration. The preferred method of administration can vary depending on various factors, e.g., the components of the composition being administered and the severity of the condition being treated.

In addition, single or multiple administrations of the compositions of the present invention may be given to a subject. For example, subjects who are particularly susceptible to flavivirus infection may require multiple administrations to establish and/or maintain protection against the virus. Levels of induced immunity provided by the pharmaceutical compositions described herein can be monitored by, e.g., measuring amounts of neutralizing secretory and serum antibodies. The dosages may then be adjusted or repeated as necessary to maintain desired levels of protection against viral infection.

The claimed invention is further described by way of the following non-limiting examples. Further aspects and embodiments of the present invention will be apparent to those of ordinary skill in the art, in view of the above disclosure and following experimental exemplification, included by way of illustration and not limitation, and with reference to the attached figures.

EXAMPLES

Example 1. MVA Vaccine Vectors and Native Zika Virus Sequences

This example provides information on exemplary MVA vaccine vectors.

TABLE 1

MVA vaccine vectors

| Vaccine designation | PrM-E sequence | NS1 protein sequence |
|---|---|---|
| GEO-ZM01 | PrM-E | none |
| GEO-ZM02 | none | NS1 (Full length) |
| GEO-ZM03 | none | NS1 (Soluble C Terminus) |
| GEO-ZM04 | PrM-E | NS1 (Full length) |
| GEO-ZM05 | PrM-E | NS1 (Soluble C Terminus) |
| GEO-ZM06 | E, full length | NS1 (Full length) |
| GEO-ZM07 | E, full length | NS1 (Soluble C Terminus) |
| GEO-ZM08 | Truncated Es | NS1 (Full length) |
| GEO-ZM09 | Truncated Es | NS1 (Soluble C Terminus) |
| GEO-ZM10 | E, full length | none |
| GEO-ZM11 | Truncated Es | none |

Native sequences are provided below which were used for development of viral inserts

```
SEQ ID 01: Native nucleotide sequence for Zika PrM-E, from GenBank (KU312312):
   1   acaggtttta ttttggattt ggaaacgaga gtttctggtc atgaaaaacc caaaaaagaa

  61   atccggagga ttccggattg tcaatatgct aaaacgcgga gtagcccgtg tgagcccctt

 121   tgggggcttg aagaggctgc cagccggact tctgctgggt catgggccca tcaggatggt

 181   cttggcgatt ctagcctttt tgagattcac ggcaatcaag ccatcactgg gtctcatcaa

 241   tagatggggt tcagtgggga aaaaagaggc tatggaaata ataaagaagt tcaagaaaga

 301   tctggctgcc atgctgagaa taatcaatgc taggaaggag aagaagagac gaggcgcaga

 361   tactagtgtc ggaattgttg gcctcctgct gaccacagct atggcagcgg aggtcactag

 421   acgtgggagt gcatactata tgtacttgga cagaaacgat gctggggagg ccatatcttt

 481   tccaaccaca ttggggatga ataagtgtta tatacagatc atggatcttg gacacacgtg
```

-continued

```
541   tgatgccacc atgagctatg aatgccctat gctggatgag gggtggaac cagatgacgt
601   cgattgttgg tgcaacacga cgtcaacttg ggttgtgtac ggaacctgcc atcacaaaaa
661   aggtgaagca cggagatcta gaagagctgt gacgctcccc tcccattcca ctaggaagct
721   gcaaacgcgg tcgcaaacct ggttggaatc aagagaatac acaaagcact tgattagagt
781   cgaaaattgg atattcagga accctggctt cgcgttagca gcagctgcca tcgcttggct
841   tttgggaagc tcaacgagcc aaaaagtcat atacttggtc atgatactgc tgattgcccc
901   ggcatacagc atcaggtgca taggagtcag caatagggac tttgtggaag gtatgtcagg
961   tgggacttgg gttgatgttg tcttggaaca tggaggttgt gtcactgtaa tggcacagga
1021  caaaccgact gtcgacatag agctggttac aacaacagtc agcaacatgg cggaggtaag
1081  atcctactgc tatgaggcat caatatcaga catggcttcg gacagccgct gcccaacaca
1141  aggtgaagcc taccttgaca agcaatcaga cactcaatat gtctgcaaaa gaacgttagt
1201  ggacagaggc tggggaaatg gatgtggact tttggcaaa gggagcctgg tgacatgcgc
1261  taagtttgca tgctccaaga aaatgaccgg gaagagcatc cagccagaga atctggagta
1321  ccggataatg ctgtcagttc atggctccca gcacagtggg atgatcgtta atgacacagg
1381  acatgaaact gatgagaata gagcgaaagt tgagataacg cccaattcac caagagccga
1441  agccaccctg ggggggtttg gaagcctagg acttgattgt gaaccgagga caggccttga
1501  cttttcagat ttgtattact tgactatgaa taacaagcac tggctggttc acaaggagtg
1561  gttccacgac attccattac cttggcacgc tggggcagac accggaactc cacactggaa
1621  caacaaagaa gcactggtag agttcaagga cgcacatgcc aaaaggcaaa ctgtcgtggt
1681  tctagggagt caagaaggag cagttcacac ggcccttgct ggagctctgg aggctgagat
1741  ggatggtgca aagggaaggc tgtcctctgg ccacttgaaa tgtcgcctga aaatggataa
1801  acttagattg aagggcgtgt catactcctt gtgtactgca gcgttcacat tcaccaagat
1861  cccggctgaa acactgcacg ggacagtcac agtggaggta cagtacgcag ggacagatgg
1921  accttgcaag gttccagctc agatggcggt ggacatgcaa actctgaccc cagttgggag
1981  gttgataacc gctaaccccg taatcactga aagcactgag aactctaaga tgatgctgga
2041  acttgatcca ccatttgggg actcttacat tgtcatagga gtcggggaga agaagatcac
2101  ccaccactgg cacaggagtg gcagcaccat tggaaaagca tttgaagcca ctgtgagagg
2161  tgccaagaga atggcagtct tgggagacac agcctgggac tttggatcag ttggaggcgc
2221  tctcaactca ttgggcaagg gcatccatca aatctttgga gcagctttca aatcattgtt
2281  tggaggaatg tcctggttct cacaaattct cattggaacg ttgctgatgt ggttgggtct
2341  gaacgcaaag aatggatcta tttcccttat gtgcttggcc ttagggggag tgttgatctt
2401  cttatccaca gccgtctctg ctgatgtggg gtgctcggtg gacttctcaa agaaggagac
2461  gagatgcggt acaggggtgt tcgtctataa cgacgttgaa gcctggaggg acaggtacaa
2521  gtaccatcct gactcccccc gtagattggc agcagcagtc aagcaagcct gggaagatgg
2581  tatctgcggg atctcctctg tttcaagaat ggaaaacatc atgtggagat cagtagaagg
2641  ggagctcaac gcaatcctgg aagagaatgg agttcaactg acggtcgttg tgggatctgt
2701  aaaaaacccc atgtggagag gtccacagag attgcccgtg cctgtgaacg agctgcccca
2761  cggctggaag gcttggggga aatcgtactt cgtcagagca gcaaagacaa ataacagctt
2821  tgtcgtggat ggtgacacac tgaaggaatg cccactcaaa catagagcat ggaacagctt
2881  tcttgtggag gatcatgggt tcggggtatt tcacactagt gtctggctca aggttagaga
2941  agattattca ttagagtgtg atccagccgt tattggaaca gctgttaagg gaaaggaggc
```

-continued 3001 tgtacacagt gatctaggct actggattga gagtgagaag aatgacacat ggaggctgaa 3061 gagggcccat ctgatcgaga tgaaaacatg tgaatggcca aagtcccaca cattgtggac 3121 agatggaata gaagagagtg atctgatcat acccaagtct ttagctgggc cactcagcca 3181 tcacaatacc agagagggct acaggaccca aatgaaaggg ccatggcaca gtgaagagct 3241 tgaaattcgg tttgaggaat gcccaggcac taaggtccac gtggaggaaa catgtggaac 3301 gagaggacca tctctgagat caaccactgc aagcggaagg gtgatcgagg aatggtgctg 3361 cagggagtgc acaatgcccc cactgtcgtt ccgggctaaa gatggctgtt ggtatggaat 3421 ggagataagg cccaggaaag aaccagaaag caacttagta aggtcaatgg tgactgcagg 3481 atcaactgat cacatggacc acttctccct tggagtgctt gtgattctgc tcatggtgca 3541 ggaagggttg aagaagagaa tgaccacaaa gatcatcata agcacatcaa tggcagtgct 3601 ggtagctatg atcctgggag gattttcaat gagtgacctg gctaagcttg caattttgat 3661 gggtgccacc ttcgcggaaa tgaacactgg aggagatgta gctcatctgg cgctgatagc 3721 ggcattcaaa gtcagaccag cgttgctggt atctttcatc ttcagagcta attggacacc 3781 ccgtgaaagc atgctgctgg ccttggcctc gtgtcttttg caaactgcga tctccgcctt 3841 ggaaggcgac ctgatggttc tcatcaatgg ttttgctttg gcctggttgg caatacgagc 3901 gatggttgtt ccacgcactg ataacatcac cttggcaatc ctggctgctc tgacaccact 3961 ggcccggggc acactgcttg tggcgtggag agcaggcctt gctacttgcg gggggtttat 4021 gctcctctct ctgaagggaa aaggcagtgt gaagaagaac ttaccatttg tcatggccct 4081 gggactaacc gctgtgaggc tggtcgaccc catcaacgtg gtgggactgc tgttgctcac 4141 aaggagtggg aagcggagct ggccccctag cgaagtactc acagctgttg gcctgatatg 4201 cgcattggct ggagggttcg ccaaggcaga tatagagatg gctgggccca tggccgcggt 4261 cggtctgcta attgtcagtt acgtggtctc aggaaagagt gtggacatgt acattgaaag 4321 agcaggtgac atcacatggg aaaaagatgc ggaagtcact ggaaacagtc cccggctcga 4381 tgtggcgcta gatgagagtg gtgatttctc cctggtggag gatgacggtc cccccatgag 4441 agagatcata ctcaaggtgg tcctgatgac catctgtggc atgaacccaa tagccatacc 4501 ctttgcagct ggagcgtggt acgtatacgt gaagactgga aaaaggagtg gtgctctatg 4561 ggatgtgcct gctcccaagg aagtaaaaaa gggggagacc acagatggag tgtacagagt 4621 aatgactcgt agactgctag gttcaacaca agttggagtg ggagttatgc aagagggggt 4681 ctttcacact atgtggcacg tcacaaaagg atccgcgctg agaagcggtg aagggagact 4741 tgatccatac tggggagatg tcaagcagga tctggtgtca tactgtggtc catggaagct 4801 agatgccgcc tgggacgggc acagcgaggt gcagctcttg gccgtgcccc ccggagagag 4861 agcgaggaac atccagactc tgcccggaat atttaagaca aaggatgggg acattggagc 4921 ggttgcgctg gattacccag caggaacttc aggatctcct atcctagaca agtgtgggag 4981 agtgatagga ctttatggca atggggtcgt gatcaaaaat gggagttatg ttagtgccat 5041 cacccaaggg aggagggagg aagagactcc tgttgagtgc ttcgagcctt cgatgctgaa 5101 gaagaagcag ctaactgtct tagacttgca tcctggagct gggaaaacca ggagagttct 5161 tcctgaaata gtccgtgaag ccataaaaac aagactccgt actgtgatct tagctccaac 5221 cagggttgtc gctgctgaaa tggaggaggc ccttagaggg cttccagtgc gttatatgac 5281 aacagcagtc aatgtcaccc actctggaac agaaatcgtc gacttaatgt gccatgccac 5341 cttcacttcg cgtctactac agccaatcag agtccccaac tataatctgt atattatgga -continued 5401 tgaggcccac ttcacagatc cctcaagtat agcagcaaga ggatacattt caacaagggt 5461 tgagatgggc gaggcggccg ccatcttcat gaccgccacg ccaccaggaa cccgtgacgc 5521 atttccggac tccaactcac caattatgga caccgaagtg gaagtcccag agagagcctg 5581 gagctcaggc tttgattggg tgacggatca ttctggaaaa acagtttggt ttgttccaag 5641 cgtgaggaac ggcaatgaga tcgcagcttg tctgacaaag gctggaaaac gggtcataca 5701 gctcagcaga aagacttttg agacagagtt ccagaaaaca aaacatcaag agtgggactt 5761 tgtcgtgaca actgacattt cagagatggg cgccaacttt aaagctgacc gtgtcataga 5821 ttccaggaga tgcctaaagc cggtcatact tgatggcgag agagtcattc tggctggacc 5881 catgcctgtc acacatgcca gcgctgccca gaggaggggg cgcataggca ggaatcccaa 5941 caaacctgga gatgagtatc tgtatggagg tgggtgcgca gagactgacg aagaccatgc 6001 acactggctt gaagcaagaa tgctccttga caatatttac ctccaagatg gcctcatagc 6061 ctcgctctat cgacctgagg ccgacaaagt agcagccatt gagggagagt tcaagcttag 6121 gacggagcaa aggaagacct ttgtggaact catgaaaaga ggagatcttc ctgtttggct 6181 ggcctatcag gttgcatctg ccggaataac ctacacagat agaagatggt gctttgatgg 6241 cacgaccaac aacaccataa tggaagacag tgtgccggca gaagtgtgga ccagacacgg 6301 agagaaaaga gtgctcaaac cgaggtggat ggacgccaga gtttgttcag atcatgcggc 6361 cctgaagtca ttcaaggagt ttgccgctgg gaaaagagga gcggcttttg gagtgatgga 6421 agccctggga acactgccag gacacatgac agagagattc caggaagcca ttgacaacct 6481 cgctgtgctc atgcgggcag agactggaag caggccttac aaagccgcgg cggcccaatt 6541 gccggagacc ctagagacca ttatgctttt ggggttgctg ggaacagtct cgctgggaat 6601 cttcttcgtc ttgatgagga acaagggcat agggaagatg ggctttggaa tggtgactct 6661 tggggccagc gcatggctca tgtggctctc ggaaattgag ccagccagaa ttgcatgtgt 6721 cctcattgtt gtgttcctat tgctggtggt gctcatacct gagccagaaa agcaaagatc 6781 tccccaggac aaccaaatgg caatcatcat catggtagca gtaggtcttc tgggcttgat 6841 taccgccaat gaactcggat ggttggagag aacaaagagt gacctaagcc atctaatggg 6901 aaggagagag gagggggcaa ccataggatt ctcaatggac attgacctgc ggccagcctc 6961 agcttgggcc atctatgctg ccttgacaac tttcattacc ccagccgtcc aacatgcagt 7021 gaccacctca tacaacaact actccttaat ggcgatggcc acgcaagctg gagtgttgtt 7081 tggtatgggc aaagggatgc cattctacgc atgggacttt ggagtcccgc tgctaatgat 7141 aggttgctac tcacaattaa cacccctgac cctaatagtg gccatcattt tgctcgtggc 7201 gcactacatg tacttgatcc cagggctgca ggcagcagct gcgcgtgctg cccagaagag 7261 aacggcagct ggcatcatga agaaccctgt tgtggatgga atagtggtga ctgacattga 7321 cacaatgaca attgaccccc aagtggagaa aaagatggga caggtgctac tcatagcagt 7381 agccgtctcc agcgccatac tgtcgcggac cgcctggggg tggggggagg ctggggccct 7441 gatcacagcc gcaacttcca ctttgtggga aggctctccg aacaagtact ggaactcctc 7501 tacagccact tcactgtgta acattttag gggaagttac ttggctggag cttctctaat 7561 ctacacagta acaagaaacg ctggcttggt caagagacgt gggggtggaa caggagagac 7621 cctgggagag aaatggaagg cccgcttgaa ccagatgtcg gccctggagt tctactccta 7681 caaaaagtca ggcatcaccg aggtgtgcag agaagaggcc cgccgcgccc tcaaggacgg 7741 tgtggcaacg ggaggccatg ctgtgtcccg aggaagtgca aagctgagat ggttggtgga 7801 gcggggatac ctgcagccct atggaaaggt cattgatctt ggatgtggca gagggggctg -continued

```
7861 gagttactac gccgccacca tccgcaaagt tcaagaagtg aaaggataca caaaaggagg
7921 ccctggtcat gaagaacccg tgttggtgca aagctatggg tggaacatag tccgtcttaa
7981 gagtggggtg gacgtctttc atatggcggc tgagccgtgt gacacgttgc tgtgtgacat
8041 aggtgagtca tcatctagtc ctgaagtgga agaagcacgg acgctcagag tcctctccat
8101 ggtgggggat tggcttgaaa aaagaccagg agccttttgt ataaaagtgt tgtgcccata
8161 caccagcact atgatggaaa ccctggagcg actgcagcgt aggtatgggg gaggactggt
8221 cagagtgcca ctctcccgca actctacaca tgagatgtac tgggtctctg gagcgaaaag
8281 caacaccata aaaagtgtgt ccaccacgag ccagctcctc ttggggcgca tggacgggcc
8341 taggaggcca gtgaaatatg aggaggatgt gaatctcggc tctggcacgc gggctgtggt
8401 aagctgcgct gaagctccca acatgaagat cattggtaac cgcattgaaa ggatccgcag
8461 tgagcacgcg gaaacgtggt tctttgacga gaaccaccca tataggacat gggcttacca
8521 tggaagctat gaggccccca cacaagggtc agcgtcctct ctaataaacg gggttgtcag
8581 gctcctgtca aaaccctggg atgtggtgac tggagtcaca ggaatagcca tgaccgacac
8641 cacaccgtat ggtcagcaaa gagttttcaa ggaaaaagtg gacactaggg tgccagaccc
8701 ccaagaaggc actcgtcagg ttatgagcat ggtctcttcc tggttgtgga aagagctagg
8761 caaacacaaa cggccacgag tctgtaccaa agaagagttc atcaacaagg ttcgtagcaa
8821 tgcagcatta ggggcaatat ttgaagagga aaaagagtgg aagactgcag tggaagctgt
8881 gaacgatcca aggttctggg ctctagtgga caaggaaaga gagcaccacc tgagaggaga
8941 gtgccagagt tgtgtgtaca acatgatggg aaaaagagaa aagaaacaag gggaatttgg
9001 aaaggccaag ggcagccgcg ccatctggta tatgtggcta ggggctagat ttctagagtt
9061 cgaagccctt ggattcttga acgaggatca ctggatgggg agagagaact caggaggtgg
9121 tgttgaaggg ctgggattac aaagactcgg atatgtccta gaagagatga gtcgtatacc
9181 aggaggaagg atgtatgcag atgacactgc tggctgggac acccgcatta gcaggtttga
9241 tctggagaat gaagctctaa tcaccaacca aatggagaaa gggcacaggg ccttggcatt
9301 ggccataatc aagtacacat accaaaacaa agtggtaaag gtccttagac cagctgaaaa
9361 agggaaaaca gttatggaca ttatttcgag acaagaccaa agggggagcg gacaagttgt
9421 cacttacgct cttaacacat ttaccaacct agtggtgcaa ctcattcgga atatggaggc
9481 tgaggaagtt ctagagatgc aagacttgtg gctgctgcgg aggtcagaga aagtgactaa
9541 ctggttgcag agcaacggat gggataggct caaacgaatg gcagtcagtg gagatgattg
9601 cgttgtgaag ccaattgatg ataggtttgc acatgccctc aggttcttga atgatatggg
9661 aaaagttagg aaggacacac aagagtggaa accctcaact ggatgggaca actgggaaga
9721 agttccgttt tgctcccacc acttcaacaa gctccatctc aaggacggga ggtccattgt
9781 ggttccctgc cgccaccaag atgaactgat tggccgggcc cgcgtctctc caggggcggg
9841 atggagcatc cgggagactg cttgcctagc aaaatcatat gcgcaaatgt ggcagctcct
9901 ttatttccac agaagggacc tccgactgat ggccaatgcc atttgttcat ctgtgccagt
9961 tgactgggtt ccaactggga gaactacctg gtcaatccat ggaaagggag aatggatgac
10021 cactgaagac atgcttgtgg tgtggaacag agtgtggatt gaggagaacg accacatgga
10081 agacaagacc ccagttacga aatggacaga cattccctat ttgggaaaaa gggaagactt
10141 gtggtgtgga tctctcatag ggcacagacc gcgcaccacc tgggctgaga acattaaaaa
10201 cacagtcaac atggtgcgca ggatcatagg tgatgaagaa aagtacatgg actacctatc
```

-continued

```
10261   cacccaagtt cgctacttgg gtgaagaagg gtctacacct ggagtgctgt aagcaccaat

10321   cttaatgttg tcaggcctgc tagtcagcca cagcttgggg aaagctgtgc agcc
```

SEQ ID 02: Native polyprotein sequence for Zika, from GenBank (ALX35659):

```
   1    MKNPKKKSGG FRIVNMLKRG VARVSPFGGL KRLPAGLLLG HGPIRMVLAI LAFLRFTAIK

  61    PSLGLINRWG SVGKKEAMEI IKKFKKDLAA MLRIINARKE KKRRGADTSV GIVGLLLTTA

 121    MAAEVTRRGS AYYMYLDRND AGEAISFPTT LGMNKCYIQI MDLGHTCDAT MSYECPMLDE

 181    GVEPDDVDCW CNTTSTWVVY GTCHHKKGEA RRSRRAVTLP SHSTRKLQTR SQTWLESREY

 241    TKHLIRVENW IFRNPGFALA AAAIAWLLGS STSQKVIYLV MILLIAPAYS IRCIGVSNRD

 301    FVEGMSGGTW VDVVLEHGGC VTVMAQDKPT VDIELVTTTV SNMAEVRSYC YEASISDMAS

 361    DSRCPTQGEA YLDKQSDTQY VCKRTLVDRG WGNGCGLFGK GSLVTCAKFA CSKKMTGKSI

 421    QPENLEYRIM LSVHGSQHSG MIVNDTGHET DENRAKVEIT PNSPRAEATL GGFGSLGLDC

 481    EPRTGLDFSD LYYLTMNNKH WLVHKEWFHD IPLPWHAGAD TGTPHWNNKE ALVEFKDAHA

 541    KRQTVVVLGS QEGAVHTALA GALEAEMDGA KGRLSSGHLK CRLKMDKLRL KGVSYSLCTA

 601    AFTFTKIPAE TLHGTVTVEV QYAGTDGPCK VPAQMAVDMQ TLTPVGRLIT ANPVITESTE

 661    NSKMMLELDP PFGDSYIVIG VGEKKITHHW HRSGSTIGKA FEATVRGAKR MAVLGDTAWD

 721    FGSVGGALNS LGKGIHQIFG AAFKSLFGGM SWFSQILIGT LLMWLGLNAK NGSISLMCLA

 781    LGGVLIFLST AVSADVGCSV DFSKKETRCG TGVFVYNDVE AWRDRYKYHP DSPRRLAAAV

 841    KQAWEDGICG ISSVSRMENI MWRSVEGELN AILEENGVQL TVVVGSVKNP MWRGPQRLPV

 901    PVNELPHGWK AWGKSYFVRA AKTNNSFVVD GDTLKECPLK HRAWNSFLVE DHGFGVFHTS

 961    VWLKVREDYS LECDPAVIGT AVKGKEAVHS DLGYWIESEK NDTWRLKRAH LIEMKTCEWP

1021    KSHTLWTDGI EESDLIIPKS LAGPLSHHNT REGYRTQMKG PWHSEELEIR FEECPGTKVH

1081    VEETCGTRGP SLRSTTASGR VIEEWCCREC TMPPLSFRAK DGCWYGMEIR PRKEPESNLV

1141    RSMVTAGSTD HMDHFSLGVL VILLMVQEGL KKRMTTKIII STSMAVLVAM ILGGFSMSDL

1201    AKLAILMGAT FAEMNTGGDV AHLALIAAFK VRPALLVSFI FRANWTPRES MLLALASCLL

1261    QTAISALEGD LMVLINGFAL AWLAIRAMVV PRTDNITLAI LAALTPLARG TLLVAWRAGL

1321    ATCGGFMLLS LKGKGSVKKN LPFVMALGLT AVRLVDPINV VGLLLLTRSG KRSWPPSEVL

1381    TAVGLICALA GGFAKADIEM AGPMAAVGLL IVSYVVSGKS VDMYIERAGD ITWEKDAEVT

1441    GNSPRLDVAL DESGDFSLVE DDGPPMREII LKVVLMTICG MNPIAIPFAA GAWYVYVKTG

1501    KRSGALWDVP APKEVKKGET TDGVYRVMTR RLLGSTQVGV GVMQEGVFHT MWHVTKGSAL

1561    RSGEGRLDPY WGDVKQDLVS YCGPWKLDAA WDGHSEVQLL AVPPGERARN IQTLPGIFKT

1621    KDGDIGAVAL DYPAGTSGSP ILDKCGRVIG LYGNGVVIKN GSYVSAITQG RREEETPVEC

1681    FEPSMLKKKQ LTVLDLHPGA GKTRRVLPEI VREAIKTRLR TVILAPTRVV AAEMEEALRG

1741    LPVRYMTTAV NVTHSGTEIV DLMCHATFTS RLLQPIRVPN YNLYIMDEAH FTDPSSIAAR

1801    GYISTRVEMG EAAAIFMTAT PPGTRDAFPD SNSPIMDTEV EVPERAWSSG FDWVTDHSGK

1861    TVWFVPSVRN GNEIAACLTK AGKRVIQLSR KTFETEFQKT KHQEVVDFWT TDISEMGANF

1921    KADRVIDSRR CLKPVILDGE RVILAGPMPV THASAAQRRG RIGRNPNKPG DEYLYGGGCA

1981    ETDEDHAHWL EARMLLDNIY LQDGLIASLY RPEADKVAAI EGEFKLRTEQ RKTFVELMKR

2041    GDLPVWLAYQ VASAGITYTD RRWCFDGTTN NTIMEDSVPA EVWTRHGEKR VLKPRWMDAR

2101    VCSDHAALKS FKEFAAGKRG AAFGVMEALG TLPGHMTERF QEAIDNLAVL MRAETGSRPY

2161    KAAAAQLPET LETIMLLGLL GTVSLGIFFV LMRNKGIGKM GFGMVTLGAS AWLMWLSEIE

2221    PARIACVLIV VFLLLVVLIP EPEKQRSPQD NQMAIIIMVA VGLLGLITAN ELGWLERTKS
```

-continued

2281 DLSHLMGRRE EGATIGFSMD IDLRPASAWA IYAALTTFIT PAVQHAVTTS YNNYSLMAMA

2341 TQAGVLFGMG KGMPFYAWDF GVPLLMIGCY SQLTPLTLIV AIILLVAHYM YLIPGLQAAA

2401 ARAAQKRTAA GIMKNPVVDG IVVTDIDTMT IDPQVEKKMG QVLLIAVAVS SAILSRTAWG

2461 WGEAGALITA ATSTLWEGSP NKYWNSSTAT SLCNIFRGSY LAGASLIYTV TRNAGLVKRR

2521 GGGTGETLGE KWKARLNQMS ALEFYSYKKS GITEVCREEA RRALKDGVAT GGHAVSRGSA

2581 KLRWLVERGY LQPYGKVIDL GCGRGGWSYY AATIRKVQEV KGYTKGGPGH EEPVLVQSYG

2641 WNIVRLKSGV DVFHMAAEPC DTLLCDIGES SSSPEVEEAR TLRVLSMVGD WLEKRPGAFC

2701 IKVLCPYTST MMETLERLQR RYGGGLVRVP LSRNSTHEMY WVSGAKSNTI KSVSTTSQLL

2761 LGRMDGPRRP VKYEEDVNLG SGTRAVVSCA EAPNMKIIGN RIERIRSEHA ETWFFDENHP

2821 YRTWAYHGSY EAPTQGSASS LINGVVRLLS KPWDVVTGVT GIAMTDTTPY GQQRVFKEKV

2881 DTRVPDPQEG TRQVMSMVSS WLWKELGKHK RPRVCTKEEF INKVRSNAAL GAIFEEEKEW

2941 KTAVEAVNDP RFWALVDKER EHHLRGECQS CVYNMMGKRE KKQGEFGKAK GSRAIWYMWL

3001 GARFLEFEAL GFLNEDHWMG RENSGGGVEG LGLQRLGYVL EEMSRIPGGR MYADDTAGWD

3061 TRISRFDLEN EALITNQMEK GHRALALAII KYTYQNKVVK VLRPAEKGKT VMDIISRQDQ

3121 RGSGQVVTYA LNTFTNLVVQ LIRNMEAEEV LEMQDLWLLR RSEKVTNWLQ SNGWDRLKRM

3181 AVSGDDCVVK PIDDRFAHAL RFLNDMGKVR KDTQEWKPST GWDNWEEVPF CSHHFNKLHL

3241 KDGRSIVVPC RHQDELIGRA RVSPGAGWSI RETACLAKSY AQMWQLLYFH RRDLRLMANA

3301 ICSSVPVDWV PTGRTTWSIH GKGEWMTTED MLVVWNRVWI EENDHMEDKT PVTKWTDIPY

3361 LGKREDLWCG SLIGHRPRTT WAENIKNTVN MVRRIIGDEE KYMDYLSTQV RYLGEEGSTP

3421 GVL

Example 2: Preparation of PrM-E Zika Sequences for Vaccine Development

This example shows the optimization of one PrM-E sequence. A vaccine construct is designed that encodes both the PrM gene and the E gene in the same construct. These two gene products are synthesized in the cell as a polyprotein and after translocation into the ER membrane are cleaved by signal peptidase into their individual forms.

Sequences of whole Zika genomes and of the PrM+E genes were acquired from across several different Zika viruses and the variability of the sequences were determined by multiple sequence alignment and analysis with Clustal Omega. From this analysis, it was decided that the sequence of the most recent viral isolate from Suriname (Genbank accession numbers ALX35659 (protein) and KU312312 (nucleic acid)) would be used as the template from which to create the PrM-E construct.

According to the gene annotation of the French Polynesian isolate of Zika, 'PrM' is located at position 126-290 of the amino acid sequence and 'E' is located at position 291-794 of the amino acid sequence. The amino acid sequence from position 126-794 is the sequence that we will therefore use for vaccine development. This sequence is 669 amino acids in length.

This sequence is as follows, with PrM distinguished from E by <u>underlining</u> the sequence and the predicted transmembrane helix domains marked by Boldlettering:

(SEQ ID NO: 3)

1 <u>TRRGSAYYMY LDRNDAGEAI SFPTTLGMNK CYIQIMDLGH TCDATMSYEC PMLDEGVEPD</u>

61 <u>DVDCWCNTTS TWVVYGTCHH KKGEARRSRR AVTLPSHSTR KLQTRSQTWL ESREYTKHLI</u>

121 <u>RVENWIFRNP GFALAAAAIA WLLGSSTSQK VIYLVMILLI APAYS</u>IRCIG VSNRDFVEGM

181 SGGTWVDVVL EHGGCVTVMA QDKPTVDIEL VTTTVSNMAE VRSYCYEASI SDMASDSRCP

241 TQGEAYLDKQ SDTQYVCKRT LVDRGWGNGC GLFGKGSLVT CAKFACSKKM TGKSIQPENL

301 EYRIMLSVHG SQHSGMIVND TGHETDENRA KVEITPNSPR AEATLGGFGS LGLDCEPRTG

361 LDFSDLYYLT MNNKHWLVHK EWFHDIPLPW HAGADTGTPH WNNKEALVEF KDAHAKRQTV

421 VVLGSQEGAV HTALAGALEA EMDGAKGRLS SGHLKCRLKM DKLRLKGVSY SLCTAAFTFT

481 KIPAETLHGT VTVEVQYAGT DGPCKVPAQM AVDMQTLTPV GRLITANPVI TESTENSKMM

541 LELDPPFGDS YIVIGVGEKK ITHHWHRSGS TIGKAFEATV RGAKRMAVLG DTAWDFGSVG

-continued

601 GALNSLGKGI HQIFGAAFKS LFGGMSWFSQ ILIGTLLMWL GLNAKNGSIS LMCLALGGVL

661 IFLSTAVSA

The signal sequence for PrM that directs the viral polyprotein to the ER translocon is located in the C-terminal end of the C gene. This signal sequence is complicated by the fact that under normal viral infection it is targeted by both the signal peptidase (in the ER lumen) and the viral protease NS3 (in the cytoplasm).

For the present design, a Japanese Encephalitis Virus (JEV) signal sequence is used instead that has been optimized for prM-E VLP production in other Flaviviruses. This JEV signal sequence is 24 amino acids long and the sequence is as follows:

(SEQ ID NO: 4)

MGKRSAGSIM WLASLAVVIA CAGA

Appending the JEV signal sequence (underlined) provides the following sequence:

(SEQ ID NO: 5)

MGKRSAGSIMWLASLAVVIACAGATRRGSAYYMYLDRNDAGEAISFPTT

LGMNKCYIQIMDLGHTCDATMSYECPMLDEGVEPDDVDCWCNTTSTWVV

YGTCHHKKGEARRSRRAVTLPSHSTRKLQTRSQTWLESREYTKHLIRVE

NWIFRNPGFALAAAAIAWLLGSSTSQKVIYLVMILLIAPAYSIRCIGVS

NRDFVEGMSGGTWVDVVLEHGGCVTVMAQDKPTVDIELVTTTVSNMAEV

RSYCYEASISDMASDSRCPTQGEAYLDKQSDTQYVCKRTLVDRGWGNGC

GLFGKGSLVTCAKFACSKKMTGKSIQPENLEYRIMLSVHGSQHSGMIVN

DTGHETDENRAKVEITPNSPRAEATLGGFGSLGLDCEPRTGLDFSDLYY

LTMNNKHWLVHKEWFHDIPLPWHAGADTGTPHWNNKEALVEFKDAHAKR

QTVVVLGSQEGAVHTALAGALEAEMDGAKGRLSSGHLKCRLKMDKLRLK

GVSYSLCTAAFTFTKIPAETLHGTVTVEVQYAGTDGPCKVPAQMAVDMQ

TLTPVGRLITANPVITESTENSKMMLELDPPFGDSYIVIGVGEKKITHH

WHRSGSTIGKAFEATVRGAKRMAVLGDTAWDFGSVGGALNSLGKGIHQI

FGAAFKSLFGGMSWFSQILIGTLLMWLGLNAKNGSISLMCLALGGVLIF

LSTAVSA

Appending this signal sequence to the N-terminal of prM-E results in the following sequence:

(SEQ ID NO: 6)

1 MGKRSAGSIM WLASLAVVIA CAGATRRGSA YYMYLDRNDA GEAISFPTTL GMNKCYIQIM

61 DLGHTCDATM SYECPMLDEG VEPDDVDCWC NTTSTWVVYG TCHHKKGEAR RSRRAVTLPS

121 HSTRKLQTRS QTWLESREYT KHLIRVENWI FRNPGFALAA AAIAWLLGSS TSQKVIYLVM

181 ILLIAPAYSI RCIGVSNRDF VEGMSGGTWV DVVLEHGGCV TVMAQDKPTV DIELVTTTVS

241 NMAEVRSYCY EASISDMASD SRCPTQGEAY LDKQSDTQYV CKRTLVDRGW GNGCGLFGKG

-continued

301 SLVTCAKFAC SKKMTGKSIQ PENLEYRIML SVHGSQHSGM IVNDTGHETD ENRAKVEITP

361 NSPRAEATLG GFGSLGLDCE PRTGLDFSDL YYLTMNNKHW LVHKEWFHDI PLPWHAGADT

421 GTPHWNNKEA LVEFKDAHAK RQTVVVLGSQ EGAVHTALAG ALEAEMDGAK GRLSSGHLKC

481 RLKMDKLRLK GVSYSLCTAA FTFTKIPAET LHGTVTVEVQ YAGTDGPCKV PAQMAVDMQT

541 LTPVGRLITA NPVITESTEN SKMMLELDPP FGDSYIVIGV GEKKITHHWH RSGSTIGKAF

601 EATVRGAKRM AVLGDTAWDF GSVGGALNSL GKGIHQIFGA AFKSLFGGMS WFSQILIGTL

661 LMWLGLNAKN GSISLMCLAL GGVLIFLSTA VSA

Using this sequence, codon optimization for Vaccinia was performed using the IDT Codon Optimization Tool. This yielded the following codon-optimized DNA sequence of length 2079 bp:

PrM-E DNA Final Optimized Nucleotide Sequence (SEQ ID NO: 7)

ATGGGAAAACGATCAGCCGGATCTATAATGTGGCTTGCAAGTCTAGCT

GTTGTTATTGCCTGTGCGGGAGCGACGCGTAGAGGATCCGCGTATTAT

ATGTATCTAGATCGTAACGACGCAGGAGAGGCTATTTCATTCCCTACG

ACTTTGGGTATGAATAAGTGCTACATTCAGATCATGGACTTAGGACAC

ACCTGTGATGCCACGATGTCCTACGAGTGCCCTATGCTAGATGAAGGA

GTAGAACCAGATGACGTAGATTGTTGGTGCAATACGACTTCCACATGG

GTTGTTTATGGTACCTGTCACCACAAGAAAGGTGAAGCTCGTAGATCT

AGACGTGCCGTGACTCTTCCCAGTCATTCCACAAGAAAACTTCAAACG

CGTTCTCAAACTTGGCTAGAAAGTCGTGAATACACGAAGCATTTAATT

CGTGTAGAGAACTGGATCTTTCGTAACCCAGGTTTCGCTCTAGCGGCC

GCCGCGATAGCTTGGTTATTGGGTTCATCAACTTCCCAAAAGGTCATT

TACTTAGTCATGATTCTTCTTATAGCCCCGGCGTACTCTATACGTTGC

ATCGGTGTATCGAATCGAGACTTTGTGGAAGGAATGTCCGGAGGAACC

TGGGTTGATGTAGTCCTAGAGCATGGTGGATGTGTCACAGTCATGGCC

CAGGATAAACCTACGGTAGACATCGAATTGGTTACGACAACAGTCAGT

AATATGGCAGAGGTAAGATCGTATTGTTATGAAGCATCCATTTCTGAC

ATGGCGTCCGATTCACGATGCCCTACCCAGGGTGAAGCATATCTAGAT

AAACAGAGTGATACACAGTACGTGTGTAAGAGAACCCTAGTTGACAGA

GGATGGGGTAACGGTTGCGGATTGTTTGGTAAAGGAAGTCTAGTGACG

TGCGCCAAGTTCGCGTGCTCAAAGAAGATGACGGGAAAGTCAATCCAA

CCGGAGAATCTTGAATACCGTATCATGTTATCAGTGCACGGATCTCAG

CATTCAGGAATGATAGTAAACGACACTGGACATGAGACGGACGAGAAC

-continued

```
AGAGCCAAGGTCGAAATCACGCCCAATTCACCTCGTGCAGAGGCAACC
CTTGGTGGATTTGGATCGCTAGGTCTTGACTGCGAACCGCGAACGGGA
TTGGACTTTTCGGATTTGTATTATCTAACTATGAATAACAAACATTGG
CTAGTTCATAAGGAATGGTTCCATGATATTCCCCTTCCCTGGCATGCA
GGAGCTGATACCGGAACACCTCATTGGAACAACAAGGAAGCACTTGTC
GAATTTAAAGATGCGCATGCGAAGCGACAAACCGTAGTTGTGTTGGGT
TCCCAAGAGGGTGCTGTGCACACAGCCCTAGCAGGTGCGCTTGAGGCG
GAAATGGATGGAGCAAAAGGTAGACTATCTTCCGGACACTTAAAATGC
AGATTAAAGATGGACAAACTTCGACTAAAAGGAGTAAGTTATTCATTA
TGTACGGCCGCATTTACTTTTACCAAAATACCAGCCGAGACGTTGCAC
GGTACGGTTACCGTGGAGGTACAGTATGCGGGTACAGATGGTCCGTGC
AAGGTGCCCGCCCAAATGGCAGTTGACATGCAGACTTTGACGCCCGTG
GGTCGTTTGATCACCGCCAACCCCGTCATCACGGAGTCTACGGAAAAC
TCCAAGATGATGTTAGAGCTAGACCCTCCATTCGGTGACTCGTACATA
GTCATTGGTGTGGGAGAGAAGAAGATTACGCATCATTGGCACAGATCG
GGATCAACAATCGGTAAGGCGTTTGAGGCGACAGTGCGAGGTGCTAAG
AGAATGGCGGTCCTTGGTGATACGGCGTGGGATTTTGGATCTGTCGGA
GGTGCTCTAAATAGTCTTGGAAAAGGTATCCACCAGATATTTGGAGCA
GCGTTTAAATCATTATTTGGTGGAATGAGTTGGTTCAGTCAAATACTT
ATCGGAACGCTTCTTATGTGGTTGGGATTGAATGCTAAGAACGGAAGT
ATTTCCTTGATGTGTCTTGCTTTGGGAGGAGTACTTATCTTCCTATCA
ACAGCCGTCTCAGCATAATAA
```

Example 3: Preparation of NS1 Sequences for Vaccine Development

According to the Zika annotation of the French Polynesian Zika isolate (GenBank Accession AHZ13508), NS1 is present as amino acids 796-1148 of the Zika polyprotein. This sequence is 353 nt long and is as follows:

```
SEQ ID 02:
Full-length Zika virus NS1 protein sequence:
                                    (SEQ ID NO: 8)
VGCSVDFSKKETRCGTGVFVYNDVEAWRDRYKYHPDSPRRLAAAVKQA
WEDGICGISSVSRMENIMWRSVEGELNAILEENGVQLTVVVGSVKNPM
WRGPQRLPVPVNELPHGWKAWGKSYFVRAAKTNNSFVVDGDTLKECPL
KHRAWNSFLVEDHGFGVFHTSVWLKVREDYSLECDPAVIGTAVKGKEA
VHSDLGYWIESEKNDTWRLKRAHLIEMKTCEWPKSHTLWTDGIEESDL
IIPKSLAGPLSHHNTREGYRTQMKGPWHSEELEIRFEECPGTKVHVEE
TCGTRGPSLRSTTASGRVIEEWCCRECTMPPLSFRAKDGCWYGMEIRP
RKEPESNLVRSMVTAGS
```

The nucleotide sequence used to encode the full-length *Zika virus* NS1 protein is as follows:

```
                                             (SEQ ID NO: 9)
ATGAAATGCCTTCTATACTTAGCCTTCTTGTTCATAGGTGTTAACTGC
GACGTTGGATGTTCCGTGGATTTCTCAAAGAAGGAGACTCGTTGCGGT
ACGGGAGTGTTTGTGTATAATGACGTGGAAGCGTGGCGTGACAGATAT
AAGTATCATCCAGATTCGCCACGTCGTCTTGCGGCTGCTGTGAAGCAA
GCGTGGGAGGATGGTATCTGTGGTATTTCCTCCGTATCTCGAATGGAG
AATATTATGTGGCGTAGTGTTGAGGGAGAACTAAACGCAATCCTAGAG
GAGAACGGAGTCCAACTTACCGTCGTCGTTGGATCCGTAAAGAATCCT
ATGTGGCGAGGTCCCCAGCGTTTACCTGTCCCCGTCAATGAGTTGCCA
CATGGTTGGAAAGCGTGGGGAAAGTCCTACTTCGTACGTGCCGCGAAG
ACCAATAATTCATTTGTGGTAGACGGAGATACATTGAAGGAGTGCCCT
TTAAAGCACCGTGCTTGGAACTCTTTCTTAGTAGAAGATCACGGTTTC
GGAGTATTTCACACATCGGTATGGCTAAAGGTACGTGAAGATTACTCG
CTTGAATGTGACCCAGCTGTTATAGGTACGGCGGTCAAAGGTAAGGAA
GCAGTGCATAGTGACCTTGGATATTGGATTGAGTCAGAGAAGAATGAC
ACATGGAGACTAAAGAGAGCACATCTTATAGAAATGAAAACTTGCGAG
TGGCCCAAATCACACACTTTGTGGACAGACGGTATTGAAGAATCCGAT
CTTATCATACCTAAATCGCTTGCAGGACCACTATCGCATCACAACACG
AGAGAGGGTTATAGAACCCAGATGAAGGGACCTTGGCATAGTGAGGAG
CTTGAAATACGTTTTGAGGAGTGTCCCGGTACTAAGGTGCATGTCGAG
GAAACTTGCGGTACTCGTGGACCATCGCTACGTTCAACAACAGCCTCG
GGTCGAGTCATTGAGGAATGGTGCTGTCGTGAATGTACCATGCCGCCT
TTATCCTTTCGTGCGAAAGACGGATGTTGGTATGGTATGGAAATTCGT
CCCAGAAAAGAGCCGGAGTCGAACCTAGTAAGATCCATGGTCACCGCG
TAATAA
```

A soluble C-terminal part of the protein can be isolated and used in place of the full length protein. This sequence is provided as follows:

```
                                             (SEQ ID NO: 10)
ATGAAATGCCTTCTATACTTAGCCTTCTTGTTCATAGGTGTTAACTGC
CGTGAAGATTACTCGCTTGAATGTGACCCAGCTGTTATAGGTACGGCG
GTCAAAGGTAAGGAAGCAGTGCATAGTGACCTTGGATATTGGATTGAG
TCAGAGAAGAATGACACATGGAGACTAAAGAGAGCACATCTTATAGAA
ATGAAAACTTGCGAGTGGCCCAAATCACACACTTTGTGGACAGACGGT
ATTGAAGAATCCGATCTTATCATACCTAAATCGCTTGCAGGACCACTA
TCGCATCACAACACGAGAGAGGGTTATAGAACCCAGATGAAGGGACCT
TGGCATAGTGAGGAGCTTGAAATACGTTTTGAGGAGTGTCCCGGTACT
AAGGTGCATGTCGAGGAAACTTGCGGTACTCGTGGACCATCGCTACGT
TCAACAACAGCCTCGGGTCGAGTCATTGAGGAATGGTGCTGTCGTGAA
TGTACCATGCCGCCTTTATCCTTTCGTGCGAAAGACGGATGTTGGTAT
```

-continued

GGTATGGAAATTCGTCCCAGAAAAGAGCCGGAGTCGAACCTAGTAAGA

TCCATGGTCACCGCGTAATAA

Example 4: Construction of Zika Sequences for Vaccine Development: Derivation of Soluble E by PCR A ZIKV soluble E (sE) gene was cloned into pLW-73. This method for production of sE required only a C-terminal truncation, so a second method is used to derive sE by PCR from the E sequences already in-house.

In short, pGZ-02 (the original prME shuttle vector in which the prME gene was cloned into pLW-73) was used as substrate for PCR. The PCR reaction incorporated (i) a forward primer that was placed upstream of the 5' restriction site for pLW-73 cloning (SmaI), and (ii) a reverse primer that truncated the E gene at the codon encoding the final lumenal amino acid Uust in front of the first amino acid of the first transmembrane domain of the E protein) using a primer with a tail that introduced two stop codons as well as the 3' restriction site for pLW-73 cloning (SalI).

A map of the PCR substrate pGZ-02 is shown in FIG. 5. This plasmid was designed to drive expression of the following ZIKV polyprotein behind the mH5 MVA promoter:

(SEQ ID NO:11)

(SEQ ID NO: 11)

```
1   IMGKRSAGSIM WLASLAVVIA CAGAIRRGSA YYMYLDRNDA GEAISFPTTL GMNKCYIQIM
61  DLGHTCDATM SYECPMLDEG VEPDDVDCWC NTTSTWVVYG TCHHKKGEAR RSRRAVTLPS
121 HSTRKLQTRS QTWLESREYT KHLIRVENWI FRNPGFALAA AAIAWLLGSS TSQKVIYLVM
181 ILLIAPAYSI RCIGVSNRDF VEGMSGGTWV DVVLEHGGCV TVMAQDKPTV DIELVTTTVS
241 NMAEVRSYCY EASISDMASD SRCPTQGEAY LDKQSDTQYV CKRTLVDRGW GNGCGLFGKG
301 SLVTCAKFAC SKKMTGKSIQ PENLEYRIML SVHGSQHSGM IVNDTGHETD ENRAKVEITP
361 NSPRAEATLG GFGSLGLDCE PRTGLDFSDL YYLTMNNKHW LVHKEWFHDI PLPWHAGADT
421 GTPHWNNKEA LVEFKDAHAK RQTVVVLGSQ EGAVHTALAG ALEAEMDGAK GRLSSGHLKC
481 RLKMDKLRLK GVSYSLCTAA FTFTKIPAET LHGTVTVEVQ YAGTDGPCKV PAQMAVDMQT
541 LTPVGRLITA NPVITESTEN SKMMLELDPP FGDSYIVIGV GEKKITHHWH RSGSTIGKAF
601 EATVRGALRM AVLGDTAWDF GSVGGALNSL GKGIHQIFGA AF9LFGGMS WFSQILIGTL
661 LMWLGLNAKN GSISLMCLAL GGVLIFLSTA VSA*
```

Seqence Annotation:

JEVSS is in *lboxed italics* prM sequence is underlined
Predicted transmembrane domains are in BOLD
E protein begins at residue 190 in this sequence numbering
|!Keia.:..Se44| (grey box) is the proposed truncation site for creating sE Tunneling down to the DNA sequence level, primers were designed to touch down on the substrate at the following locations (indicated by gray arrows, with partial 5'→3' primer sequences visible inside the arrows):

The forward (F) and reverse (R) primer sequences used here for annealing to the substrate are as follows:

F primer sequence:

(SEQ ID NO: 12)
5'-GAAAGCGAGAAATAATCATAAATAAGCC-3'

Substrate sequence:

(SEQ ID NO: 13)
5'-GAAAGCGAGAAATAATCATAAATAAGCC-3'

R primer sequence:

(SEQ ID NO: 14)
3'-GTCTATAAACCTCGTCGCAAATTT-5'

Substrate sequence:

(SEQ ID NO: 15)
5'-CAGATATTTGGAGCAGCGTTTAAA-3'

In addition, it was necessary to add a 5' tail to the R primer to facilitate introduction of stop codons and a SalI restriction site. In order to keep the primers comparable in composition, a 5' tail were added to the F primer as well. Thus, the final primer sequences (with physical characteristics annotated) were as follows, with 5' tails marked by underlying and the SalI restriction site in lower-case letters:

F primer final sequence:

(SEQ ID NO: 16)
5'-GACTCAGTCTAGGAAAGCGAGAAATAATCATAAATAAGCC-3'

28 nt annealing, 12 nt tail: 40 nt total
predicted Tm: 62.8° C. (annealing), 73.8° C. (final)
38% CG content R primer final sequence:

(SEQ ID NO: 17)
5'-TACTAgtcgacTACTATTTAAACGCTGCTCCAAATATCTG-3'

24 nt annealing, 16 nt tail: 40 nt total
predicted Tm: 60.1° C. (annealing), 73.8° C. (final)
38% CG content PCR of the pGZ-02 plasmid with these two primers yielded a PCR product 1989 nt in length, as follows with the SmaI site labeled as BOLD and the SalI site labeled as BOLD ITALIC in green and the start codon and two stop codons underlined:

(SEQ ID NO: 18)

1 GACTCAGTCT AGGAAAGCGA GAAATAATCA TAAATAAGCC CGGGATGGGA AAACGATCAG

61 CCGGATCTAT AATGTGGCTT GCAAGTCTAG CTGTTGTTAT TGCCTGTGCG GGAGCGACGC

121 GTAGAGGATC CGCGTATTAT ATGTATCTAG ATCGTAACGA CGCAGGAGAG GCTATTTCAT

181 TCCCTACGAC TTTGGGTATG AATAAGTGCT ACATTCAGAT CATGGACTTA GGACACACCT

241 GTGATGCCAC GATGTCCTAC GAGTGCCCTA TGCTAGATGA AGGAGTAGAA CCAGATGACG

301 TAGATTGTTG GTGCAATACG ACTTCCACAT GGGTTGTTTA TGGTACCTGT CACCACAAGA

361 AAGGTGAAGC TCGTAGATCT AGACGTGCCG TGACTCTTCC CAGTCATTCC ACAAGAAAAC

421 TTCAAACGCG TTCTCAAACT TGGCTAGAAA GTCGTGAATA CACGAAGCAT TTAATTCGTG

481 TAGAGAACTG GATCTTTCGT AACCCAGGTT TCGCTCTAGC GGCCGCCGCG ATAGCTTGGT

541 TATTGGGTTC ATCAACTTCC CAAAAGGTCA TTTACTTAGT CATGATTCTT CTTATAGCCC

601 CGGCGTACTC TATACGTTGC ATCGGTGTAT CGAATCGAGA CTTTGTGGAA GGAATGTCCG

661 GAGGAACCTG GGTTGATGTA GTCCTAGAGC ATGGTGGATG TGTCACAGTC ATGGCCCAGG

721 ATAAACCTAC GGTAGACATC GAATTGGTTA CGACAACAGT CAGTAATATG GCAGAGGTAA

781 GATCGTATTG TTATGAAGCA TCCATTTCTG ACATGGCGTC CGATTCACGA TGCCCTACCC

841 AGGGTGAAGC ATATCTAGAT AAACAGAGTG ATACACAGTA CGTGTGTAAG AGAACCCTAG

901 TTGACAGAGG ATGGGGTAAC GGTTGCGGAT TGTTTGGTAA AGGAAGTCTA GTGACGTGCG

961 CCAAGTTCGC GTGCTCAAAG AAGATGACGG GAAAGTCAAT CCAACCGGAG AATCTTGAAT

1021 ACCGTATCAT GTTATCAGTG CACGGATCTC AGCATTCAGG AATGATAGTA AACGACACTG

-continued

1081 GACATGAGAC GGACGAGAAC AGAGCCAAGG TCGAAATCAC GCCCAATTCA CCTCGTGCAG

1141 AGGCAACCCT TGGTGGATTT GGATCGCTAG GTCTTGACTG CGAACCGCGA ACGGGATTGG

1201 ACTTTTCGGA TTTGTATTAT CTAACTATGA ATAACAAACA TTGGCTAGTT CATAAGGAAT

1261 GGTTCCATGA TATTCCCCTT CCCTGGCATG CAGGAGCTGA TACCGGAACA CCTCATTGGA

1321 ACAACAAGGA AGCACTTGTC GAATTTAAAG ATGCGCATGC GAAGCGACAA ACCGTAGTTG

1381 TGTTGGGTTC CCAAGAGGGT GCTGTGCACA CAGCCCTAGC AGGTGCGCTT GAGGCGGAAA

1441 TGGATGGAGC AAAAGGTAGA CTATCTTCCG GACACTTAAA ATGCAGATTA AAGATGGACA

1501 AACTTCGACT AAAAGGAGTA AGTTATTCAT TATGTACGGC CGCATTTACT TTTACCAAAA

1561 TACCAGCCGA GACGTTGCAC GGTACGGTTA CCGTGGAGGT ACAGTATGCG GGTACAGATG

1621 GTCCGTGCAA GGTGCCCGCC CAAATGGCAG TTGACATGCA GACTTTGACG CCCGTGGGTC

1681 GTTTGATCAC CGCCAACCCC GTCATCACGG AGTCTACGGA AAACTCCAAG ATGATGTTAG

1741 AGCTAGACCC TCCATTCGGT GACTCGTACA TAGTCATTGG TGTGGGAGAG AAGAAGATTA

1801 CGCATCATTG GCACAGATCG GGATCAACAA TCGGTAAGGC GTTTGAGGCG ACAGTGCGAG

1861 GTGCTAAGAG AATGGCGGTC CTTGGTGATA CGGCGTGGGA TTTTGGATCT GTCGGAGGTG

1921 CTCTAAATAG TCTTGGAAAA GGTATCCACC AGATATTTGG AGCAGCGTTT *AAATAGTAGT*

1961 CGACTAGTA

Once digested with SmaI and SalI, this sequence was ligated into similarly digested pLW-73. The resulting plasmid was named pGZ-05. This plasmid was slightly different from pGZ-04 (the sE shuttle plasmid constructed from the synthetic gene produced by Genscript) by (1) using stop codons of sequence 'TAG' (as necessitated by primer design) whereas pGZ-04 uses stop codons of sequence 'TAA', and (2) pGZ-05 is 1 nt smaller in size than pGZ-04 because the last nt of the second codon is also the first nt of the SalI site in pGZ-05, whereas these two are juxtaposed and non-overlapping in pGZ-04.

The map for pGZ-05 is shown in FIG. 6.

For completeness, it should be noted that this construct drives expression of the following gene product from the mHS MVA promoter:

(SEQ ID NO: 19)

1 *IMGKRSAGSIM WLASLAVVIA* CAGAIRRGSA YYMYLDRNDA GEAISFPTTL GMNKCYIQIM

61 DLGHTCDATM SYECPMLDEG VEPDDVDCWC NTTSTWVVYG TCHHKKGEAR RSRRAVTLPS

121 HSTRKLQTRS QTWLESREYT KHLIRVENWI FRNPGFALAA AAIAWLLGSS TSQKVIYLVM

181 ILLIAPAYSI RCIGVSNRDF VEGMSGGTWV DVVLEHGGCV TVMAQDKPTV DIELVTTTVS

241 NMAEVRSYCY EASISDMASD SRCPTQGEAY LDKQSDTQYV CKRTLVDRGW GNGCGLFGKG

301 SLVTCAKFAC SKKMTGKSIQ PENLEYRIML SVHGSQHSGM IVNDTGHETD ENRAKVEITP

361 NSPRAEATLG GFGSLGLDCE PRTGLDFSDL YYLTMNNKHW LVHKEWFHDI PLPWHAGADT

-continued

```
421  GTPHWNNKEA LVEFKDAHAK RQTVVVLGSQ EGAVHTALAG ALEAEMDGAK GRLSSGHLKC

481  RLKMDKLRLK GVSYSLCTAA FTFTKIPAET LHGTVTVEVQ YAGTDGPCKV PAQMAVDMQT

541  LTPVGRLITA NPVITESTEN SKMMLELDPP FGDSYIVIGV GEKKITHHWH RSGSTIGKAF

601  EATVRGAKRM AVLGDTAWDF GSVGGALNSL GKGIHQIFGA AFK*
Seqence Annotation:

JEVSS is in axed italics

prM sequence is underlined
Predicted prM transmembrane domains are in BOLD
E protein begins at I190 and ends with K643 in this numbering.
```

Example 5: Construction of Zika Sequences for Vaccine Development: Soluble E 160628

In addition to the prME-expressing vector, a soluble version was created wherein the transmembrane domains of the E protein have been removed to facilitate expression and secretion of E.

The soluble E (sE) sequence uses the same prME sequences, but in this case the sE protein is truncated just upstream of the first transmembrane domain.

According to the gene annotation of the French Polynesian isolate of Zika, 'prM' is located at position 126-290 of the amino acid sequence and 'E' is located at position 291-794 of the amino acid sequence. The amino acid sequence from position 126-794 is the sequence that was used for vaccine development. This sequence is 669 amino acids in length. Prediction of transmembrane helix domains of E was obtained from ViPR Virus Pathogen Resource annotation of the gene. This sequence is as follows, with prM distinguished from E by underlining the sequence and the predicted transmembrane helix domains marked by BOLD lettering:

```
                                                          (SEQ ID NO: 20)
  1 TRRGSAYYMY LDRNDAGEAI SFPTTLGMNK CYIQIMDLGH TCDATMSYEC PMLDEGVEPD

 61 DVDCWCNTTS TWVVYGTCHH KKGEARRSRR AVTLPSHSTR KLQTRSQTWL ESREYTKHLI

121 RVENWIFRNP GFALAAAAIA WLLGSSTSQK VIYLVMILLI APAYSIRCIG VSNRDFVEGM

181 SGGTWVDVVL EHGGCVTVMA QDKPTVDIEL VTTTVSNMAE VRSYCYEASI SDMASDSRCP

241 TQGEAYLDKQ SDTQYVCKRT LVDRGWGNGC GLFGKGSLVT CAKFACSKKM TGKSIQPENL

301 EYRIMLSVHG SQHSGMIVND TGHETDENRA KVEITPNSPR AEATLGGFGS LGLDCEPRTG

361 LDFSDLYYLT MNNKHWLVHK EWFHDIPLPW HAGADTGTPH WNNKEALVEF KDAHAKRQTV

421 VVLGSQEGAV HTALAGALEA EMDGAKGRLS SGHLKCRLKM DKLRLKGVSY SLCTAAFTFT

481 KIPAETLHGT VTVEVQYAGT DGPCKVPAQM AVDMQTLTPV GRLITANPVI TESTENSKMM

541 LELDPPFGDS YIVIGVGEKK ITHHWHRSGS TIGKAFEATV RGAKRMAVLG DTAWDFGSVG

601 GALNSLGKGI HQIFGAAFKS LFGGMSWFSQ ILIGTLLMWL GLNAKNGSIS LMCLALGGVL

661 IFLSTAVSA
```

It should be possible to create sE by truncating the sequence after amino acid 619 to yield the following sequence for prMsE:

```
                                                          (SEQ ID NO: 21)
  1 TRRGSAYYMY LDRNDAGEAI SFPTTLGMNK CYIQIMDLGH TCDATMSYEC PMLDEGVEPD

 61 DVDCWCNTTS TWVVYGTCHH KKGEARRSRR AVTLPSHSTR KLQTRSQTWL ESREYTKHLI

121 RVENWIFRNP GFALAAAAIA WLLGSSTSQK VIYLVMILLI APAYSIRCIG VSNRDFVEGM

181 SGGTWVDVVL EHGGCVTVMA QDKPTVDIEL VTTTVSNMAE VRSYCYEASI SDMASDSRCP

241 TQGEAYLDKQ SDTQYVCKRT LVDRGWGNGC GLFGKGSLVT CAKFACSKKM TGKSIQPENL

301 EYRIMLSVHG SQHSGMIVND TGHETDENRA KVEITPNSPR AEATLGGFGS LGLDCEPRTG
```

-continued

```
361 LDFSDLYYLT MNNKHWLVHK EWFHDIPLPW HAGADTGTPH WNNKEALVEF KDAHAKRQTV

421 VVLGSQEGAV HTALAGALEA EMDGAKGRLS SGHLKCRLKM DKLRLKGVSY SLCTAAFTFT

481 KIPAETLHGT VTVEVQYAGT DGPCKVPAQM AVDMQTLTPV GRLITANPVI TESTENSKMM

541 LELDPPFGDS YIVIGVGEKK ITHHWHRSGS TIGKAFEATV RGAKRMAVLG DTAWDFGSVG

601 GALNSLGKGI HQIFGAAFK
```

The signal sequence for prM that directs the viral polyprotein to the ER translocon is located in the C-terminal end of the C gene. This signal sequence is complicated by the fact that under normal viral infection it is targeted by both the signal peptidase (in the ER lumen) and the viral protease NS3 (in the cytoplasm). This construct was chosen to utilize a Japanese Encephalitis Virus signal sequence that has been optimized for prM-E VLP production in other Flaviviruses. This JEV signal sequence is 24 amino acids long and the sequence is as follows:

MGKRSAGSIM WLASLAWIA CAGA (SEQ ID NO:22)

Appending this signal sequence to the N-terminal of prMsE results in the following sequence:

```
                                                   (SEQ ID :23)
  1 MGKRSAGSIM WLASLAVVIA CAGATRRGSA YYMYLDRNDA
    GEAISFPTTL GMNKCYIQIM

 61 DLGHTCDATM SYECPMLDEG VEPDDVDCWC NTTSTWVVYG
    TCHHKKGEAR RSRRAVTLPS

121 HSTRKLQTRS QTWLESREYT KHLIRVENWI FRNPGFALAA
    AAIAWLLGSS TSQKVIYLVM

181 ILLIAPAYSI RCIGVSNRDF VEGMSGGTWV DVVLEHGGCV
    TVMAQDKPTV DIELVTTTVS

241 NMAEVRSYCY EASISDMASD SRCPTQGEAY LDKQSDTQYV
    CKRTLVDRGW GNGCGLFGKG

301 SLVTCAKFAC SKKMTGKSIQ PENLEYRIML SVHGSQHSGM
    IVNDTGHETD ENRAKVEITP

361 NSPRAEATLG GFGSLGLDCE PRTGLDFSDL YYLTMNNKHW
    LVHKEWFHDI PLPWHAGADT

421 GTPHWNNKEA LVEFKDAHAK RQTVVVLGSQ EGAVHTALAG
    ALEAEMDGAK GRLSSGHLKC

481 RLKMDKLRLK GVSYSLCTAA FTFTKIPAET LHGTVTVEVQ
    YAGTDGPCKV PAQMAVDMQT

541 LTPVGRLITA NPVITESTEN SKMMLELDPP FGDSYIVIGV
    GEKKITHHWH RSGSTIGKAF

601 EATVRGAKRM AVLGDTAWDF GSVGGALNSL GKGIHQIFGA AFK
```

Using this sequence, codon optimization for Vaccinia was performed using the IDT Codon Optimization Tool. This yielded the following codon-optimized DNA sequence of length 1929 bp:

```
                                              (SEQ ID NO: 24)
ATGGGAAAACGATCAGCCGGATCTATAATGTGGCTTGCAAGTCTAGCT

GTTGTTATTGCCTGTGCGGGAGCGACGCGTAGAGGATCCGCGTATTAT

ATGTATCTAGATCGTAACGACGCAGGAGAGGCTATTTCATTCCCTACG

ACTTTGGGTATGAATAAGTGCTACATTCAGATCATGGACTTAGGACAC

ACCTGTGATGCCACGATGTCCTACGAGTGCCCTATGCTAGATGAAGGA
```

-continued

```
GTAGAACCAGATGACGTAGATTGTTGGTGCAATACGACTTCCACATGG

GTTGTTTATGGTACCTGTCACCACAAGAAAGGTGAAGCTCGTAGATCT

AGACGTGCCGTGACTCTTCCCAGTCATTCCACAAGAAAACTTCAAACG

CGTTCTCAAACTTGGCTAGAAAGTCGTGAATACACGAAGCATTTAATT

CGTGTAGAGAACTGGATCTTTCGTAACCCAGGTTTCGCTCTAGCGGCC

GCCGCGATAGCTTGGTTATTGGGTTCATCAACTTCCCAAAAGGTCATT

TACTTAGTCATGATTCTTCTTATAGCCCCGGCGTACTCTATACGTTGC

ATCGGTGTATCGAATCGAGACTTTGTGGAAGGAATGTCCGGAGGAACC

TGGGTTGATGTAGTCCTAGAGCATGGTGGATGTGTCACAGTCATGGCC

CAGGATAAACCTACGGTCGACATCGAATTGGTTACGACAACAGTCAGT

AATATGGCAGAGGTAAGATCGTATTGTTATGAAGCATCCATTTCTGAC

ATGGCGTCCGATTCACGATGCCCTACCCAGGGTGAAGCATATCTAGAT

AAACAGAGTGATACACAGTACGTGTGTAAGAGAACCCTAGTTGACAGA

GGATGGGGTAACGGTTGCGGATTGTTTGGTAAAGGAAGTCTAGTGACG

TGCGCCAAGTTCGCGTGCTCAAAGAAGATGACGGGAAAGTCAATCCAA

CCGGAGAATCTTGAATACCGTATCATGTTATCAGTGCACGGATCTCAG

CATTCAGGAATGATAGTAAACGACACTGGACATGAGACGGACGAGAAC

AGAGCCAAGGTCGAAATCACGCCCAATTCACCTCGTGCAGAGGCAACC

CTTGGTGGATTIGGATCGCTAGGTCTTGACTGCGAACCGCGAACGGGA

TTGGACTTTTCGGATTTGTATTATCTAACTATGAATAACAAACATTGG

CTAGTTCATAAGGAATGGTTCCATGATATTCCCCTTCCCTGGCATGCA

GGAGCTGATACCGGAACACCTCATTGGAACAACAAGGAAGCACTTGTC

GAATTTAAAGATGCGCATGCGAAGCGACAAACCGTAGTTGTGTTGGGT

TCCCAAGAGGGTGCTGTGCACACAGCCCTAGCAGGTGCGCTTGAGGCG

GAAATGGATGGAGCAAAAGGTAGACTATCTTCCGGACACTTAAAATGC

AGATTAAAAATGGACAAACTTCGACTAAAAGGAGTAAGTTATTCATTA

TGTACGGCCGCATTTACTTTTACCAAAATACCAGCCGAGACGTTGCAC

GGTACGGTTACCGTGGAGGTACAGTATGCGGGTACAGATGGTCCGTGC

AAGGTGCCCGCCCAAATGGCAGTTGACATGCAGACTTTGACGCCCGTG

GGTCGTTTGATCACCGCCAACCCCGTCATCACGGAGTCTACGGAAAAC

TCCAAGATGATGTTAGAGCTAGACCCTCCATTCGGTGACTCGTACATA

GTCATTGGTGTGGGAGAGAAGAAGATTACGCATCATTGGCACAGATCG

GGATCAACAATCGGTAAGGCGTTTGAGGCGACAGTGCGAGGTGCTAAG
```

-continued

```
AGAATGGCGGTCCTTGGTGATACGGCGTGGGATTTTGGATCTGTCGGA

GGTGCTCTAAATAGTCTTGGAAAAGGTATCCACCAGATATTTGGAGCA

GCGTTTAAA
```

The preparation of the sequence used the following protocol:

1. Start with the natural sequence
2. Codon optimize DNA sequence for vaccinia virus
3. Research the sequence for homopolymers stretches of >4 nt: 2::G, 2::C, 2::T and 2::A
4. If any, interrupt all homopolymer sequences by silent mutations
5. Research sequence for vaccinia virus transcription terminator: TsNT (UUUUUNU)
6. If any, interrupt all transcription terminator motifs by silent mutation
7. Add a second stop codon (TAA)
8. Add restriction enzymes for cloning of the Zika genes into MVA-shuttles plasmids
   i. Modified deletion III: Smal-Sall
   ii. Between essential genes (I8/G1): Smal-Sall
9. Choose the site and location of the gene into MVA virus
10. Choose the appropriate MVA-shuttle No homopolymer stretches of >4 nt were found in the sequence for bases G, C, or T after steps 1-2. One As sequences was found at sites 1446-1450. The AAAAA was changed to AAACA, a silent mutation for lysine.

Next the sequence was scanned for vaccinia virus transcriptional terminator sequences. None were found.

Two stop codons were appended to the end of the sequence (TAATAA), as no stop codon was present in the original sequence above.

The sequence was scanned for internal Smal or Sall restriction sites. A Sall restriction site (GTCGAC) was found at 688-693. This sequence was changed to GT6GAC, a silent mutation for valine.

A Smal site (CCCGGG) was added to the 5' end of the construct. A Sall (GTCGAC) site was added to the 3' end of the construct. This yielded a final sequence of length 1947 nt as follows:

```
                                              (SEQ ID NO: 25)
   1 CCCGGGATGG GAAAACGATC AGCCGGATCT ATAATGTGGC
     TTGCAAGTCT AGCTGTTGTT

  61 ATTGCCTGTG CGGGAGCGAC GCGTAGAGGA TCCGCGTATT
     ATATGTATCT AGATCGTAAC

 121 GACGCAGGAG AGGCTATTTC ATTCCCTACG ACTTTGGGTA
     TGAATAAGTG CTACATTCAG

 181 ATCATGGACT TAGGACACAC CTGTGATGCC ACGATGTCCT
     ACGAGTGCCC TATGCTAGAT

 241 GAAGGAGTAG AACCAGATGA CGTAGATTGT TGGTGCAATA
     CGACTTCCAC ATGGGTTGTT

 301 TATGGTACCT GTCACCACAA GAAAGGTGAA GCTCGTAGAT
     CTAGACGTGC CGTGACTCTT

 361 CCCAGTCATT CCACAAGAAA ACTTCAAACG CGTTCTCAAA
     CTTGGCTAGA AAGTCGTGAA

 421 TACACGAAGC ATTTAATTCG TGTAGAGAAC TGGATCTTTC
     GTAACCCAGG TTTCGCTCTA

 481 GCGGCCGCCG CGATAGCTTG GTTATTGGGT TCATCAACTT
     CCCAAAAGGT CATTTACTTA

 541 GTCATGATTC TTCTTATAGC CCCGGCGTAC TCTATACGTT
     GCATCGGTGT ATCGAATCGA

 601 GACTTTGTGG AAGGAATGTC CGGAGGAACC TGGGTTGATG
     TAGTCCTAGA GCATGGTGGA

 661 TGTGTCACAG TCATGGCCCA GGATAAACCT ACGGTAGACA
     TCGAATTGGT TACGACAACA

 721 GTCAGTAATA TGGCAGAGGT AAGATCGTAT TGTTATGAAG
     CATCCATTTC TGACATGGCG

 781 TCCGATTCAC GATGCCCTAC CCAGGGTGAA GCATATCTAG
     ATAAACAGAG TGATACACAG

 841 TACGTGTGTA AGAGAACCCT AGTTGACAGA GGATGGGGTA
     ACGGTTGCGG ATTGTTTGGT

 901 AAAGGAAGTC TAGTGACGTG CGCCAAGTTC GCGTGCTCAA
     AGAAGATGAC GGGAAAGTCA

 961 ATCCAACCGG AGAATCTTGA ATACCGTATC ATGTTATCAG
     TGCACGGATC TCAGCATTCA

1021 GGAATGATAG TAAACGACAC TGGACATGAG ACGGACGAGA
     ACAGAGCCAA GGTCGAAATC

1081 ACGCCCAATT CACCTCGTGC AGAGGCAACC CTTGGTGGAT
     TTGGATCGCT AGGTCTTGAC

1141 TGCGAACCGC GAACGGGATT GGACTTTTCG GATTTGTATT
     ATCTAACTAT GAATAACAAA

1201 CATTGGCTAG TTCATAAGGA ATGGTTCCAT GATATTCCCC
     TTCCCTGGCA TGCAGGAGCT

1261 GATACCGGAA CACCTCATTG GAACAACAAG GAAGCACTTG
     TCGAATTTAA AGATGCGCAT

1321 GCGAAGCGAC AAACCGTAGT TGTGTTGGGT TCCCAAGAGG
     GTGCTGTGCA CACAGCCCTA

1381 GCAGGTGCGC TTGAGGCGGA AATGGATGGA GCAAAAGGTA
     GACTATCTTC CGGACACTTA

1441 AAATGCAGAT TAAAGATGGA CAAACTTCGA CTAAAAGGAG
     TAAGTTATTC ATTATGTACG

1501 GCCGCATTTA CTTTTACCAA AATACCAGCC GAGACGTTGC
     ACGGTACGGT TACCGTGGAG

1561 GTACAGTATG CGGGTACAGA TGGTCCGTGC AAGGTGCCCG
     CCCAAATGGC AGTTGACATG

1621 CAGACTTTGA CGCCCGTGGG TCGTTTGATC ACCGCCAACC
     CCGTCATCAC GGAGTCTACG

1681 GAAAACTCCA AGATGATGTT AGAGCTAGAC CCTCCATTCG
     GTGACTCGTA CATAGTCATT

1741 GGTGTGGGAG AGAAGAAGAT TACGCATCAT TGGCACAGAT
     CGGGATCAAC AATCGGTAAG

1801 GCGTTTGAGG CGACAGTGCG AGGTGCTAAG AGAATGGCGG
     TCCTTGGTGA TACGGCGTGG

1861 GATTTTGGAT CTGTCGGAGG TGCTCTAAAT AGTCTTGGAA
     AAGGTATCCA CCAGATATTT

1921 GGAGCAGCGT TTAAATAATA AGTCGAC
```

This construct was submitted for synthesis and cloning into pLW-73, driven by the mHS promoter, with the P11 promoter driving GFP expression in the same plasmid and all CDS flanked 5' by 18 (I8R) and 3' by G1 (GIL). This plasmid will be named pGZ-04. A map is shown in FIG. 7:

Example 6: Preclinical Evaluation of MVA-Zika Vaccine Compositions

Western Blots and Electron Microscopy.

The expression of full-length prME and NS1 was confirmed by western blot (WB). MVA-Zika plaques were stained with Zika specific antibodies directed to the E proteins (FIG. 8). VLP formation was evaluated with thin section electron micrographs performed at the Emory University Apkarian Integrated Electron Microscopy Core (FIG. 9). The native conformation of the E and NS1 proteins expressed on MVA-VLPs was assessed by immunostaining using ZIKV-specific E and NS1 antibodies (Aalto Bio Reagents) and flavivirus group reactive E-specific monoclonal antibody (mAb) 4G2.

Efficacy Testing of MVA-ZIKA Vaccine Candidates in Mice.

Pre-clinical testing of MVA-ZIKV-NS1 and MVA-ZIKV-prME in mice demonstrated outstanding protection for the MVA-ZIKV-NS1 vaccine (FIG. 10). We have developed a rigorous challenge model system using high-dose intracranial/intracerebral (IC) inoculation of CD1 mice with a heterologous ZIKV strain (MR766). Protection in this context represents a very high bar for immunity and no other vaccine has yet been shown to confer protection with this challenge model. Vaccination with $10^7$ TCIDso MVA-ZIKV-NS1 or MVA-ZIKV-prME was well tolerated by recipient mice with no overt signs of illness or weight loss prior to challenge. ELISA data demonstrated abundant Abs generated to ZIKV NS1 and E proteins, respectively (FIG. 3A). Upon challenge, MVA-ZIKV-NS1-immunized mice were completely (100%) protected after both prime only and prime-boost immunizations, whereas MVA-ZIKV-prME-immunized mice showed 60-80% protection. No significant symptoms or weight loss were observed with any vaccinated animals. In contrast, most sham-immunized animals lost weight and were euthanized according to the approved animal protocols at CDC.

Due to its structure, NS1 is expressed by cells as either a dimer that non-covalently binds to the surface of cells or as a hexamer that is secreted. As an immunogen, NS1 provides two potential targets for protective immune responses: (i) intracellular NS1 as a target for CDS+ T cell responses, and (ii) cell-associated extracellular dimeric NS1 is present as repetitive epitopes on the surface of infected cells as a target for Fe-mediated Ab killing. Expression of NS1 alone does not lead to VLP formation. Our data indicate that cells infected with the MVA-ZIKV-NS1 vaccine express both the cell-associated NS1 and secrete NS1 into the supernatant (FIG. 8).

MVA-ZIKV-prME drives excellent production of E protein in infected cells (FIG. 8) and produces VLPs that bud into the secretory pathway of cells and are secreted into supernatant (FIG. 9). This vaccination approach provides two pools of Ag to stimulate the immune system: (i) intracellular E protein, and (ii) E protein displayed on the plasma membrane surface of secreted VLPs, thereby strongly stimulating both the cellular and humeral arms of the immune system.

Using the MVA platform, two vaccines have been constructed: (1) an MVA vaccine that expresses ZIKV NS1 in host cells, leading to both endogenous expression and secretion of NS1 (MVA-ZIKV-NS1); and (2) an MVA vaccine that drives expression of ZIKV prME in host cells and has the additional feature of budding virus-like particles (VLPs) that display E protein in its native form from the same cells (MVA-ZIKV-prME). The sequences used in these vaccine constructs were derived from the Asian Suriname isolate Z1106033 of the 2015 ZIKV epidemic. The Asian and American strains have maintained >96% amino acid homologies with their African ancestors (Lanciotti, R. S., Lambert, A. J., Holodniy, M., Saavedra, S. & del Carmen Castillo, L. Phylogeny of Zika Virus in Western Hemisphere, 2015. Emerging Infectious Disease 1865 journal 22(2016); Stauft, C. B., Gorbatsevych, O., Cello, J., Wimmer, E. & Futcher, B. Comparison of African, Asian, and American Zika Viruses in Swiss Webster mice: Virulence, neutralizing antibodies, and serotypes. bioRxiv (2016) (e.g. MR766 used in our challenge studies) and immunity to one strain has been shown to confer immunity to other strains (Dowd, K. A., et al. Broadly Neutralizing Activity of Zika Virus-Immune Sera Identifies a Single Viral Serotype. Cell Rep 16, 1485-1491 (2016). Both African and Asian lineages shown to induce microcephaly in mice. NS1 and prME sequences in our vaccine maintain 96-99% identity with their Asian and African strains indicating that our vaccines will likely be effective for all circulating strains.

Although NS1 is expressed on infected cells, it is not incorporated into ZIKV virions 1875 (Diamond, M. S., Pierson, T. C. & Fremont, D. H. The structural immunology of antibody protection against West Nile virus. Immunol Rev 225, 212-225 (2008). The expression of prME is sufficient to generate secreted VLPs (Fuchs, J., et al. Investigating the efficacy of monovalent and tetravalent dengue vaccine formulations against DENV-4 challenge in AG129 mice. Vaccine 32, 16 (2014). Galula, J. U., Shen, W.-F., Chuang, S.-T., Chang, G.-J. J. & Chao, D.-Y. Virus-Like Particle Secretion and Genotype-Dependent Immunogenicity of Dengue Virus Serotype 2 DNA Vaccine. Journal of Virology 88, 18 (2014). Vaughan, K., Greenbaum, J., Blythe, M., Peters, B. & Sette, A. Meta-analysis of All Immune Epitope Data in the *Flavivirus* Genus: Inventory of Current Immune Epitope Data Status in the Context of Virus Immunity and Immunopathology. Viral Immunol 23, 26 (2010). The prME proteins are expressed as a single polypeptide chain, which is cleaved into prM and E proteins by signal peptidase in the host cells (Faye, O., et al. Molecular Evolution of Zika Virus during Its Emergence in the 20th Century. PLoS Negl Trop Dis 8, 10 (2014). Perera, R., Khaliq, M. & Kuhn, R. J. Closing the door on flaviviruses: Entry as a target for antiviral drug design. Antiviral Research 80, 11-22 (2008). The prM protein is in turn cleaved into pr (non-M) and M proteins during virus maturation, with M protein being primarily incorporated into mature virions to produce a heterodimer with trimers of E protein (Lee, P. O., et al. The Fe region of an antibody impacts the neutralization of West Nile viruses in different maturation states. J Virol 87, 13729-13740 (2013). These Ags were chosen based on documented evidence that flavivirus NS1 or prME proteins are sufficient to elicit a protective immune response (Edeling, M. A., Diamond, M. S. & Fremont, D. H. Structural basis of *Flavivirus* NS1 assembly and antibody recognition. Proceedings of the National Academy of Sciences 111, 4285-4290 (2014). Heinz, F. X. & Stiasny, K. Flaviviruses and flavivirus vaccines. Vaccine 30, 4301-4306 (2012). This novel combination of vector platform and native Ag conformation yields a vaccine that is expected to elicit a strong, broad, and durable immune response.

The ideal ZIKV vaccine is safe for women of child-bearing age, cost effective to manufacture, and induces protective levels of long-lasting antibody and T cell responses after a single dose. Given that ZIKV is currently circulating predominantly in developing countries, the MVA-NS1 vaccine is attractive for accelerated development of a ZIKV vaccine because it provides the potential for single dose elicitation of durable immune responses (Marzi et al, in preparation) and cost effective manufacturability. MVA vaccines are replication competent in avian cells used for vaccine production, yet replication deficient in mammalian cells making them safe for humans, including immunocompromised individuals. MVA has been shown to be safe in >120,000 individuals, including HIV-infected individuals, and has shown no reproductive toxicity in studies in pregnant rats (CHMP), C.f.M.P.f.H.U. Assessment report, IMVANEX, Common name: Modified Vaccinia Ankara virus, Procedure No. EMEA/H/C/002596. (ed. (CHMP), C.f.M.P.f.H.U.) (European Medicines Agency, London, U K, 2013). Cosma, A., et al. Therapeutic vaccination with MVA-HIV-1 nef elicits Net-specific T-helper cell responses in chronically HIV-1 infected individuals. Vaccine 22, 21-29 (2003). Carroll, M. W. & Moss, B. Host range and cytopathogenicity of the highly attenuated MVA strain of vaccinia virus: propagation and generation of recombinant viruses in a nonhuman mammalian cell line. Virology 238, 198-211 (1997). For ZIKV vaccines, WHO recommended non-live/inactivated approaches for vaccination of women of child-bearing age (WHO and experts prioritize vaccines, diagnostics and innovative vector control tools for Zika R&D. (2016). Our approach is in line with this recommendation as MVA-ZIKV vaccines match the excellent safety profile of non-live/inactivated vaccines without the need for an adjuvant, and additionally offer potential for high levels of immunogenicity and efficacy after a single dose. Moreover, the NS1 vaccine poses no potential risk of induction of ADE in vaccinated subjects living in dengue endemic areas Using the very high bar of intracranial inoculation with heterologous virus, MVA-ZIKV-prME vaccine showed good protection (FIG. 10) and will be tested side-by-side with MVA-ZIKV-NS1 in NHP before selection of the final candidate to be advanced into clinic.

A high level of protection against ZIKV infection is expected through at least 3 different mechanisms: (1) Fe-mediated non-neutralizing antibodies that bind virus or virus infected cells displaying E or NS1 proteins and kill through such mechanisms as binding complement, initiating antibody-dependent cellular cytotoxicity and phagocytosis; (2) Ag-specific T cells targeting prME or NS1 epitopes in infected cells; and (3) neutralizing antibodies that target viral epitopes on E that are critical for virus entry (e.g. receptor binding and fusion peptides).

The foregoing discussion discloses and describes merely exemplary embodiments of the present invention. One skilled in the art will readily recognize from such discussion, and from the accompanying drawings and claims, that various changes, modifications and variations can be made therein without departing from the spirit and scope of the invention as defined in the following claims.

All references cited herein are incorporated by reference in their entirety.

We claim:

1. A recombinant modified vaccinia Ankara (MVA) vector comprising a nucleic acid sequence encoding a *Zika virus* nonstructural 1 (NS1) protein or a fragment thereof, wherein the nucleic acid sequence is under the control of a promoter compatible with poxvirus expression systems.

2. The recombinant MVA vector of claim 1, wherein the nucleic acid sequence is inserted into a deletion site selected from I, II, III, IV, V, or VI.

3. The recombinant MVA vector of claim 1, wherein the nucleic acid sequence is inserted between two essential and highly conserved MVA genes or into a restructured and modified deletion III.

4. The recombinant MVA vector of claim 1, wherein the promoter is selected from the group consisting of Pm2H5 promoter, Psyn II promoter, and mH5 promoter.

5. A pharmaceutical composition comprising a recombinant MVA vector, wherein the MVA vector comprises a nucleic acid sequence encoding a *Zika virus* non-structural 1 (NS1) protein, wherein the nucleic acid is inserted into the MVA vector under the control of a promoters compatible with poxvirus expression systems, and a pharmaceutically acceptable carrier.

6. The pharmaceutical composition of claim 5, wherein the recombinant MVA vector is formulated for intraperitoneal, intramuscular, intradermal, epidermal, mucosal or intravenous administration.

7. A method of inducing an immune response in a subject in need thereof, said method comprising administering to the subject an effective amount of a recombinant MVA vector effective to induce an immune response against a *Zika virus*, wherein the recombinant MVA vector comprises a nucleic acid sequence encoding a-*Zika virus* nonstructural 1 (NS1) protein, and wherein the nucleic acid is under the control of a promoters compatible with poxvirus expression systems.

8. The method of claim 7, wherein the immune response is a humoral immune response, a cellular immune response, or a combination thereof.

9. The method of claim 7, wherein the immune response comprises production of binding antibodies against the *Zika virus*.

10. The method of claim 7, wherein the immune response comprises production of neutralizing antibodies against the *Zika virus*.

11. The method of claim 7, wherein the immune response comprises production of a cell-mediated immune response against the *Zika virus*.

12. A method of treating a *Zika virus* infection in a subject in need thereof, said method comprising administering to the subject an amount of a recombinant MVA vector effective to induce an immune response, wherein the recombinant MVA vector comprises a nucleic acid sequence encoding a *Zika virus* nonstructural 1 (NS1) protein, and wherein the nucleic acid sequence is under the control of a promoters compatible with poxvirus expression systems.

13. The method of claim 12, wherein the subject is exposed to *Zika virus*, but not yet symptomatic of *Zika virus* infection.

14. The recombinant MVA vector of claim 1, wherein the nucleic acid sequence comprises the nucleic acid sequence of SEQ ID NO:9.

15. The recombinant MVA vector of claim 1, wherein the *Zika virus* NS1 protein comprises the amino acid sequence of SEQ ID NO:8.

16. The recombinant MVA vector of claim 1, wherein the nucleic acid sequence comprises the nucleic acid sequence of SEQ ID NO:10.

17. The recombinant MVA vector of claim 1, wherein the nucleic acid sequence further comprises a signal peptide sequence.

18. The recombinant MVA vector of claim 1, wherein the nucleic acid is optimized by one or more methods selected from changing selected codons to other synonymous codons that are optimal for protein expression by MVA, interrupting homopolymer stretches using silent mutations, interrupting transcription terminator motifs using silent mutations, or a combination thereof.

19. The recombinant MVA vector of claim 3, wherein the nucleic acid sequence is inserted into the restructured and modified deletion site III between MVA genes A50R and B1R.

20. The pharmaceutical composition of claim 5, wherein the nucleic acid sequence comprises the nucleic acid sequence of SEQ ID NO:9.

21. The pharmaceutical composition of claim 5, wherein the *Zika virus* NS1 protein comprises the amino acid sequence of SEQ ID NO:8.

22. The pharmaceutical composition of claim 5, wherein the nucleic acid sequence comprises the nucleic acid sequence of SEQ ID NO:10.

* * * * *

SEQUENCE LISTING

```
<160> NUMBER OF SEQ ID NOS: 25

<210> SEQ ID NO 1
<211> LENGTH: 10374
<212> TYPE: DNA
<213> ORGANISM: Zika virus

<400> SEQUENCE: 1

acaggtttta ttttggattt ggaaacgaga gtttctggtc atgaaaaacc caaaaaagaa      60

atccggagga ttccggattg tcaatatgct aaaacgcgga gtagcccgtg tgagcccctt     120

tgggggcttg aagaggctgc cagccggact tctgctgggt catgggccca tcaggatggt     180

cttggcgatt ctagcctttt tgagattcac ggcaatcaag ccatcactgg gtctcatcaa     240

tagatggggt tcagtgggga aaaaagaggc tatggaaata ataaagaagt tcaagaaaga     300

tctggctgcc atgctgagaa taatcaatgc taggaaggag aagaagagac gaggcgcaga     360

tactagtgtc ggaattgttg gcctcctgct gaccacagct atggcagcgg aggtcactag     420

acgtgggagt gcatactata tgtacttgga cagaaacgat gctggggagg ccatatcttt     480

tccaaccaca ttggggatga ataagtgtta tatacagatc atggatcttg gacacacgtg     540

tgatgccacc atgagctatg aatgccctat gctggatgag ggggtggaac cagatgacgt     600

cgattgttgg tgcaacacga cgtcaacttg ggttgtgtac ggaacctgcc atcacaaaaa     660

aggtgaagca cggagatcta gaagagctgt gacgctcccc tcccattcca ctaggaagct     720

gcaaacgcgg tcgcaaacct ggttggaatc aagagaatac acaaagcact tgattagagt     780

cgaaaattgg atattcagga accctggctt cgcgttagca gcagctgcca tcgcttggct     840

tttgggaagc tcaacgagcc aaaaagtcat atacttggtc atgatactgc tgattgcccc     900

ggcatacagc atcaggtgca taggagtcag caatagggac tttgtggaag gtatgtcagg     960

tgggacttgg gttgatgttg tcttggaaca tggaggttgt gtcactgtaa tggcacagga    1020
```

-continued caaaccgact gtcgacatag agctggttac aacaacagtc agcaacatgg cggaggtaag 1080
atcctactgc tatgaggcat caatatcaga catggcttcg gacagccgct gcccaacaca 1140
aggtgaagcc taccttgaca agcaatcaga cactcaatat gtctgcaaaa gaacgttagt 1200
ggacagaggc tggggaaatg gatgtggact ttttggcaaa gggagcctgg tgacatgcgc 1260
taagtttgca tgctccaaga aaatgaccgg gaagagcatc cagccagaga atctggagta 1320
ccggataatg ctgtcagttc atggctccca gcacagtggg atgatcgtta atgacacagg 1380
acatgaaact gatgagaata gagcgaaagt tgagataacg cccaattcac caagagccga 1440
agccaccctg ggggggtttg gaagcctagg acttgattgt gaaccgagga caggccttga 1500
cttttcagat ttgtattact tgactatgaa taacaagcac tggctggttc acaaggagtg 1560
gttccacgac attccattac cttggcacgc tggggcagac accggaactc cacactggaa 1620
caacaaagaa gcactggtag agttcaagga cgcacatgcc aaaaggcaaa ctgtcgtggt 1680
tctagggagt caagaaggag cagttcacac ggcccttgct ggagctctgg aggctgagat 1740
ggatggtgca aagggaaggc tgtcctctgg ccacttgaaa tgtcgcctga aaatggataa 1800
acttagattg aagggcgtgt catactcctt gtgtactgca gcgttcacat tcaccaagat 1860
cccggctgaa acactgcacg ggacagtcac agtggaggta cagtacgcag ggacagatgg 1920
accttgcaag gttccagctc agatggcggt ggacatgcaa actctgaccc cagttgggag 1980
gttgataacc gctaaccccg taatcactga aagcactgag aactctaaga tgatgctgga 2040
acttgatcca ccatttgggg actcttacat tgtcatagga gtcggggaga agaagatcac 2100
ccaccactgg cacaggagtg gcagcaccat tggaaaagca tttgaagcca ctgtgagagg 2160
tgccaagaga atggcagtct tgggagacac agcctgggac tttggatcag ttggaggcgc 2220
tctcaactca ttgggcaagg gcatccatca aatctttgga gcagctttca aatcattgtt 2280
tggaggaatg tcctggttct cacaaattct cattggaacg ttgctgatgt ggttgggtct 2340
gaacgcaaag aatggatcta tttcccttat gtgcttggcc ttagggggag tgttgatctt 2400
cttatccaca gccgtctctg ctgatgtggg gtgctcggtg gacttctcaa agaaggagac 2460
gagatgcggt acaggggtgt tcgtctataa cgacgttgaa gcctggaggg acaggtacaa 2520
gtaccatcct gactcccccc gtagattggc agcagcagtc aagcaagcct gggaagatgg 2580
tatctgcggg atctcctctg tttcaagaat ggaaaacatc atgtggagat cagtagaagg 2640
ggagctcaac gcaatcctgg aagagaatgg agttcaactg acggtcgttg tgggatctgt 2700
aaaaaacccc atgtggagag gtccacagag attgcccgtg cctgtgaacg agctgcccca 2760
cggctggaag gcttggggga aatcgtactt cgtcagagca gcaaagacaa ataacagctt 2820
tgtcgtggat ggtgacacac tgaaggaatg cccactcaaa catagagcat ggaacagctt 2880
tcttgtggag gatcatgggt tcggggtatt tcacactagt gtctggctca aggttagaga 2940
agattattca ttagagtgtg atccagccgt tattggaaca gctgttaagg gaaaggaggc 3000
tgtacacagt gatctaggct actggattga gagtgagaag aatgacacat ggaggctgaa 3060
gagggcccat ctgatcgaga tgaaaacatg tgaatggcca aagtcccaca cattgtggac 3120
agatggaata gaagagagtg atctgatcat acccaagtct ttagctgggc cactcagcca 3180
tcacaatacc agagagggct acaggaccca aatgaaaggg ccatggcaca gtgaagagct 3240
tgaaattcgg tttgaggaat gcccaggcac taaggtccac gtggaggaaa catgtggaac 3300
gagaggacca tctctgagat caaccactgc aagcggaagg gtgatcgagg aatggtgctg 3360
cagggagtgc acaatgcccc cactgtcgtt ccgggctaaa gatggctgtt ggtatggaat 3420

-continued

```
ggagataagg cccaggaaag aaccagaaag caacttagta aggtcaatgg tgactgcagg   3480
atcaactgat cacatggacc acttctccct tggagtgctt gtgattctgc tcatggtgca   3540
ggaagggttg aagaagagaa tgaccacaaa gatcatcata agcacatcaa tggcagtgct   3600
ggtagctatg atcctgggag gattttcaat gagtgacctg gctaagcttg caattttgat   3660
gggtgccacc ttcgcggaaa tgaacactgg aggagatgta gctcatctgg cgctgatagc   3720
ggcattcaaa gtcagaccag cgttgctggt atctttcatc ttcagagcta attggacacc   3780
ccgtgaaagc atgctgctgg ccttggcctc gtgtcttttg caaactgcga tctccgcctt   3840
ggaaggcgac ctgatggttc tcatcaatgg ttttgctttg gcctggttgg caatacgagc   3900
gatggttgtt ccacgcactg ataacatcac cttggcaatc ctggctgctc tgacaccact   3960
ggcccggggc acactgcttg tggcgtggag agcaggcctt gctacttgcg gggggtttat   4020
gctcctctct ctgaagggaa aaggcagtgt gaagaagaac ttaccatttg tcatggccct   4080
gggactaacc gctgtgaggc tggtcgaccc catcaacgtg gtgggactgc tgttgctcac   4140
aaggagtggg aagcggagct ggccccctag cgaagtactc acagctgttg gcctgatatg   4200
cgcattggct ggagggttcg ccaaggcaga tatagagatg gctgggccca tggccgcggt   4260
cggtctgcta attgtcagtt acgtggtctc aggaaagagt gtggacatgt acattgaaag   4320
agcaggtgac atcacatggg aaaaagatgc ggaagtcact ggaaacagtc cccggctcga   4380
tgtggcgcta gatgagagtg gtgatttctc cctggtggag gatgacggtc cccccatgag   4440
agagatcata ctcaaggtgg tcctgatgac catctgtggc atgaacccaa tagccatacc   4500
ctttgcagct ggagcgtggt acgtatacgt gaagactgga aaaaggagtg gtgctctatg   4560
ggatgtgcct gctcccaagg aagtaaaaaa gggggagacc acagatggag tgtacagagt   4620
aatgactcgt agactgctag gttcaacaca agttggagtg ggagttatgc aagagggggt   4680
ctttcacact atgtggcacg tcacaaaagg atccgcgctg agaagcggtg aagggagact   4740
tgatccatac tggggagatg tcaagcagga tctggtgtca tactgtggtc catggaagct   4800
agatgccgcc tgggacgggc acagcgaggt gcagctcttg gccgtgcccc ccggagagag   4860
agcgaggaac atccagactc tgcccggaat atttaagaca aaggatgggg acattggagc   4920
ggttgcgctg gattacccag caggaacttc aggatctcct atcctagaca agtgtgggag   4980
agtgatagga ctttatggca atggggtcgt gatcaaaaat gggagttatg ttagtgccat   5040
cacccaaggg aggagggagg aagagactcc tgttgagtgc ttcgagcctt cgatgctgaa   5100
gaagaagcag ctaactgtct tagacttgca tcctggagct gggaaaacca ggagagttct   5160
tcctgaaata gtccgtgaag ccataaaaac aagactccgt actgtgatct tagctccaac   5220
cagggttgtc gctgctgaaa tggaggaggc ccttagaggg cttccagtgc gttatatgac   5280
aacagcagtc aatgtcaccc actctggaac agaaatcgtc gacttaatgt gccatgccac   5340
cttcacttcg cgtctactac agccaatcag agtccccaac tataatctgt atattatgga   5400
tgaggcccac ttcacagatc cctcaagtat agcagcaaga ggatacattt caacaagggt   5460
tgagatgggc gaggcggccg ccatcttcat gaccgccacg ccaccaggaa cccgtgacgc   5520
atttccggac tccaactcac caattatgga caccgaagtg gaagtcccag agagagcctg   5580
gagctcaggc tttgattggg tgacggatca ttctggaaaa acagtttggt ttgttccaag   5640
cgtgaggaac ggcaatgaga tcgcagcttg tctgacaaag gctggaaaac gggtcataca   5700
gctcagcaga aagacttttg agacagagtt ccagaaaaca aaacatcaag agtgggactt   5760
```

-continued

```
tgtcgtgaca actgacattt cagagatggg cgccaacttt aaagctgacc gtgtcataga   5820
ttccaggaga tgcctaaagc cggtcatact tgatggcgag agagtcattc tggctggacc   5880
catgcctgtc acacatgcca gcgctgccca gaggaggggg cgcataggca ggaatcccaa   5940
caaacctgga gatgagtatc tgtatggagg tgggtgcgca gagactgacg aagaccatgc   6000
acactggctt gaagcaagaa tgctccttga caatatttac ctccaagatg gcctcatagc   6060
ctcgctctat cgacctgagg ccgacaaagt agcagccatt gagggagagt tcaagcttag   6120
gacggagcaa aggaagacct ttgtggaact catgaaaaga ggagatcttc ctgtttggct   6180
ggcctatcag gttgcatctg ccggaataac ctacacagat agaagatggt gctttgatgg   6240
cacgaccaac aacaccataa tggaagacag tgtgccggca gaagtgtgga ccagacacgg   6300
agagaaaaga gtgctcaaac cgaggtggat ggacgccaga gtttgttcag atcatgcggc   6360
cctgaagtca ttcaaggagt ttgccgctgg gaaaagagga gcggcttttg gagtgatgga   6420
agccctggga acactgccag gacacatgac agagagattc caggaagcca ttgacaacct   6480
cgctgtgctc atgcgggcag agactggaag caggccttac aaagccgcgg cggcccaatt   6540
gccggagacc ctagagacca ttatgctttt ggggttgctg ggaacagtct cgctgggaat   6600
cttcttcgtc ttgatgagga acaagggcat agggaagatg ggctttggaa tggtgactct   6660
tggggccagc gcatggctca tgtggctctc ggaaattgag ccagccagaa ttgcatgtgt   6720
cctcattgtt gtgttcctat tgctggtggt gctcatacct gagccagaaa agcaaagatc   6780
tccccaggac aaccaaatgg caatcatcat catggtagca gtaggtcttc tgggcttgat   6840
taccgccaat gaactcggat ggttggagag aacaaagagt gacctaagcc atctaatggg   6900
aaggagagag gagggggcaa ccataggatt ctcaatggac attgacctgc ggccagcctc   6960
agcttgggcc atctatgctg ccttgacaac tttcattacc ccagccgtcc aacatgcagt   7020
gaccacctca tacaacaact actccttaat ggcgatggcc acgcaagctg gagtgttgtt   7080
tggtatgggc aaagggatgc cattctacgc atgggacttt ggagtcccgc tgctaatgat   7140
aggttgctac tcacaattaa cacccctgac cctaatagtg gccatcattt tgctcgtggc   7200
gcactacatg tacttgatcc cagggctgca ggcagcagct gcgcgtgctg cccagaagag   7260
aacggcagct ggcatcatga agaaccctgt tgtggatgga atagtggtga ctgacattga   7320
cacaatgaca attgaccccc aagtggagaa aaagatggga caggtgctac tcatagcagt   7380
agccgtctcc agcgccatac tgtcgcggac cgcctggggg tggggggagg ctggggccct   7440
gatcacagcc gcaacttcca ctttgtggga aggctctccg aacaagtact ggaactcctc   7500
tacagccact tcactgtgta acatttttag ggggaagttac ttggctggag cttctctaat   7560
ctacacagta acaagaaacg ctggcttggt caagagacgt gggggtggaa caggagagac   7620
cctgggagag aaatggaagg cccgcttgaa ccagatgtcg gccctggagt tctactccta   7680
caaaaagtca ggcatcaccg aggtgtgcag agaagaggcc cgccgcgccc tcaaggacgg   7740
tgtggcaacg ggaggccatg ctgtgtcccg aggaagtgca aagctgagat ggttggtgga   7800
gcggggatac ctgcagccct atggaaaggt cattgatctt ggatgtggca gagggggctg   7860
gagttactac gccgccacca tccgcaaagt tcaagaagtg aaaggataca caaaaggagg   7920
ccctggtcat gaagaacccg tgttggtgca aagctatggg tggaacatag tccgtcttaa   7980
gagtggggtg gacgtctttc atatggcggc tgagccgtgt gacacgttgc tgtgtgacat   8040
aggtgagtca tcatctagtc ctgaagtgga agaagcacgg acgctcagag tcctctccat   8100
ggtgggggat tggcttgaaa aaagaccagg agccttttgt ataaaagtgt tgtgcccata   8160
```

-continued

```
caccagcact atgatggaaa ccctggagcg actgcagcgt aggtatgggg gaggactggt   8220

cagagtgcca ctctcccgca actctacaca tgagatgtac tgggtctctg gagcgaaaag   8280

caacaccata aaaagtgtgt ccaccacgag ccagctcctc ttggggcgca tggacgggcc   8340

taggaggcca gtgaaatatg aggaggatgt gaatctcggc tctggcacgc gggctgtggt   8400

aagctgcgct gaagctccca acatgaagat cattggtaac cgcattgaaa ggatccgcag   8460

tgagcacgcg gaaacgtggt tctttgacga gaaccaccca tataggacat gggcttacca   8520

tggaagctat gaggccccca cacaagggtc agcgtcctct ctaataaacg ggttgtcag   8580

gctcctgtca aaaccctggg atgtggtgac tggagtcaca ggaatagcca tgaccgacac   8640

cacaccgtat ggtcagcaaa gagttttcaa ggaaaaagtg gacactaggg tgccagaccc   8700

ccaagaaggc actcgtcagg ttatgagcat ggtctcttcc tggttgtgga aagagctagg   8760

caaacacaaa cggccacgag tctgtaccaa agaagagttc atcaacaagg ttcgtagcaa   8820

tgcagcatta ggggcaatat ttgaagagga aaaagagtgg aagactgcag tggaagctgt   8880

gaacgatcca aggttctggg ctctagtgga caaggaaaga gagcaccacc tgagaggaga   8940

gtgccagagt tgtgtgtaca acatgatggg aaaaagagaa aagaaacaag gggaatttgg   9000

aaaggccaag ggcagccgcg ccatctggta tatgtggcta ggggctagat ttctagagtt   9060

cgaagccctt ggattcttga acgaggatca ctggatgggg agagagaact caggaggtgg   9120

tgttgaaggg ctgggattac aaagactcgg atatgtccta gaagagatga gtcgtatacc   9180

aggaggaagg atgtatgcag atgacactgc tggctgggac acccgcatta gcaggtttga   9240

tctggagaat gaagctctaa tcaccaacca aatggagaaa gggcacaggg ccttggcatt   9300

ggccataatc aagtacacat accaaaacaa agtggtaaag gtccttagac cagctgaaaa   9360

agggaaaaca gttatggaca ttatttcgag acaagaccaa agggggagcg gacaagttgt   9420

cacttacgct cttaacacat ttaccaacct agtggtgcaa ctcattcgga atatggaggc   9480

tgaggaagtt ctagagatgc aagacttgtg gctgctgcgg aggtcagaga aagtgactaa   9540

ctggttgcag agcaacggat gggataggct caaacgaatg gcagtcagtg gagatgattg   9600

cgttgtgaag ccaattgatg ataggtttgc acatgccctc aggttcttga atgatatggg   9660

aaaagttagg aaggacacac aagagtggaa accctcaact ggatgggaca actgggaaga   9720

agttccgttt tgctcccacc acttcaacaa gctccatctc aaggacggga ggtccattgt   9780

ggttccctgc cgccaccaag atgaactgat tggccgggcc cgcgtctctc caggggcggg   9840

atggagcatc cgggagactg cttgcctagc aaaatcatat gcgcaaatgt ggcagctcct   9900

ttatttccac agaagggacc tccgactgat ggccaatgcc atttgttcat ctgtgccagt   9960

tgactgggtt ccaactggga gaactacctg gtcaatccat ggaaagggag aatggatgac  10020

cactgaagac atgcttgtgg tgtggaacag agtgtggatt gaggagaacg accacatgga  10080

agacaagacc ccagttacga aatggacaga cattccctat ttgggaaaaa gggaagactt  10140

gtggtgtgga tctctcatag ggcacagacc gcgcaccacc tgggctgaga acattaaaaa  10200

cacagtcaac atggtgcgca ggatcatagg tgatgaagaa aagtacatgg actacctatc  10260

cacccaagtt cgctacttgg gtgaagaagg gtctacacct ggagtgctgt aagcaccaat  10320

cttaatgttg tcaggcctgc tagtcagcca cagcttgggg aaagctgtgc agcc        10374
```

<210> SEQ ID NO 2
<211> LENGTH: 3423
<212> TYPE: PRT

-continued

<213> ORGANISM: Zika virus

<400> SEQUENCE: 2

```
Met Lys Asn Pro Lys Lys Lys Ser Gly Gly Phe Arg Ile Val Asn Met
1               5                   10                  15

Leu Lys Arg Gly Val Ala Arg Val Ser Pro Phe Gly Gly Leu Lys Arg
            20                  25                  30

Leu Pro Ala Gly Leu Leu Leu Gly His Gly Pro Ile Arg Met Val Leu
        35                  40                  45

Ala Ile Leu Ala Phe Leu Arg Phe Thr Ala Ile Lys Pro Ser Leu Gly
    50                  55                  60

Leu Ile Asn Arg Trp Gly Ser Val Gly Lys Lys Glu Ala Met Glu Ile
65                  70                  75                  80

Ile Lys Lys Phe Lys Lys Asp Leu Ala Ala Met Leu Arg Ile Ile Asn
                85                  90                  95

Ala Arg Lys Glu Lys Lys Arg Arg Gly Ala Asp Thr Ser Val Gly Ile
            100                 105                 110

Val Gly Leu Leu Leu Thr Thr Ala Met Ala Ala Glu Val Thr Arg Arg
        115                 120                 125

Gly Ser Ala Tyr Tyr Met Tyr Leu Asp Arg Asn Asp Ala Gly Glu Ala
    130                 135                 140

Ile Ser Phe Pro Thr Thr Leu Gly Met Asn Lys Cys Tyr Ile Gln Ile
145                 150                 155                 160

Met Asp Leu Gly His Thr Cys Asp Ala Thr Met Ser Tyr Glu Cys Pro
                165                 170                 175

Met Leu Asp Glu Gly Val Glu Pro Asp Asp Val Asp Cys Trp Cys Asn
            180                 185                 190

Thr Thr Ser Thr Trp Val Val Tyr Gly Thr Cys His His Lys Lys Gly
        195                 200                 205

Glu Ala Arg Arg Ser Arg Arg Ala Val Thr Leu Pro Ser His Ser Thr
    210                 215                 220

Arg Lys Leu Gln Thr Arg Ser Gln Thr Trp Leu Glu Ser Arg Glu Tyr
225                 230                 235                 240

Thr Lys His Leu Ile Arg Val Glu Asn Trp Ile Phe Arg Asn Pro Gly
                245                 250                 255

Phe Ala Leu Ala Ala Ala Ala Ile Ala Trp Leu Leu Gly Ser Ser Thr
            260                 265                 270

Ser Gln Lys Val Ile Tyr Leu Val Met Ile Leu Leu Ile Ala Pro Ala
        275                 280                 285

Tyr Ser Ile Arg Cys Ile Gly Val Ser Asn Arg Asp Phe Val Glu Gly
    290                 295                 300

Met Ser Gly Gly Thr Trp Val Asp Val Val Leu Glu His Gly Gly Cys
305                 310                 315                 320

Val Thr Val Met Ala Gln Asp Lys Pro Thr Val Asp Ile Glu Leu Val
                325                 330                 335

Thr Thr Thr Val Ser Asn Met Ala Glu Val Arg Ser Tyr Cys Tyr Glu
            340                 345                 350

Ala Ser Ile Ser Asp Met Ala Ser Asp Ser Arg Cys Pro Thr Gln Gly
        355                 360                 365

Glu Ala Tyr Leu Asp Lys Gln Ser Asp Thr Gln Tyr Val Cys Lys Arg
    370                 375                 380

Thr Leu Val Asp Arg Gly Trp Gly Asn Gly Cys Gly Leu Phe Gly Lys
385                 390                 395                 400
```

-continued

```
Gly Ser Leu Val Thr Cys Ala Lys Phe Ala Cys Ser Lys Lys Met Thr
                405                 410                 415

Gly Lys Ser Ile Gln Pro Glu Asn Leu Glu Tyr Arg Ile Met Leu Ser
            420                 425                 430

Val His Gly Ser Gln His Ser Gly Met Ile Val Asn Asp Thr Gly His
        435                 440                 445

Glu Thr Asp Glu Asn Arg Ala Lys Val Glu Ile Thr Pro Asn Ser Pro
    450                 455                 460

Arg Ala Glu Ala Thr Leu Gly Gly Phe Gly Ser Leu Gly Leu Asp Cys
465                 470                 475                 480

Glu Pro Arg Thr Gly Leu Asp Phe Ser Asp Leu Tyr Tyr Leu Thr Met
                485                 490                 495

Asn Asn Lys His Trp Leu Val His Lys Glu Trp Phe His Asp Ile Pro
            500                 505                 510

Leu Pro Trp His Ala Gly Ala Asp Thr Gly Thr Pro His Trp Asn Asn
        515                 520                 525

Lys Glu Ala Leu Val Glu Phe Lys Asp Ala His Ala Lys Arg Gln Thr
    530                 535                 540

Val Val Val Leu Gly Ser Gln Glu Gly Ala Val His Thr Ala Leu Ala
545                 550                 555                 560

Gly Ala Leu Glu Ala Glu Met Asp Gly Ala Lys Gly Arg Leu Ser Ser
                565                 570                 575

Gly His Leu Lys Cys Arg Leu Lys Met Asp Lys Leu Arg Leu Lys Gly
            580                 585                 590

Val Ser Tyr Ser Leu Cys Thr Ala Ala Phe Thr Phe Thr Lys Ile Pro
        595                 600                 605

Ala Glu Thr Leu His Gly Thr Val Thr Val Glu Val Gln Tyr Ala Gly
    610                 615                 620

Thr Asp Gly Pro Cys Lys Val Pro Ala Gln Met Ala Val Asp Met Gln
625                 630                 635                 640

Thr Leu Thr Pro Val Gly Arg Leu Ile Thr Ala Asn Pro Val Ile Thr
                645                 650                 655

Glu Ser Thr Glu Asn Ser Lys Met Met Leu Glu Leu Asp Pro Pro Phe
            660                 665                 670

Gly Asp Ser Tyr Ile Val Ile Gly Val Gly Glu Lys Lys Ile Thr His
        675                 680                 685

His Trp His Arg Ser Gly Ser Thr Ile Gly Lys Ala Phe Glu Ala Thr
    690                 695                 700

Val Arg Gly Ala Lys Arg Met Ala Val Leu Gly Asp Thr Ala Trp Asp
705                 710                 715                 720

Phe Gly Ser Val Gly Gly Ala Leu Asn Ser Leu Gly Lys Gly Ile His
                725                 730                 735

Gln Ile Phe Gly Ala Ala Phe Lys Ser Leu Phe Gly Gly Met Ser Trp
            740                 745                 750

Phe Ser Gln Ile Leu Ile Gly Thr Leu Leu Met Trp Leu Gly Leu Asn
        755                 760                 765

Ala Lys Asn Gly Ser Ile Ser Leu Met Cys Leu Ala Leu Gly Gly Val
    770                 775                 780

Leu Ile Phe Leu Ser Thr Ala Val Ser Ala Asp Val Gly Cys Ser Val
785                 790                 795                 800

Asp Phe Ser Lys Lys Glu Thr Arg Cys Gly Thr Gly Val Phe Val Tyr
                805                 810                 815

Asn Asp Val Glu Ala Trp Arg Asp Arg Tyr Lys Tyr His Pro Asp Ser
```

-continued

```
            820                 825                 830

Pro Arg Arg Leu Ala Ala Ala Val Lys Gln Ala Trp Glu Asp Gly Ile
        835                 840                 845

Cys Gly Ile Ser Ser Val Ser Arg Met Glu Asn Ile Met Trp Arg Ser
    850                 855                 860

Val Glu Gly Glu Leu Asn Ala Ile Leu Glu Glu Asn Gly Val Gln Leu
865                 870                 875                 880

Thr Val Val Val Gly Ser Val Lys Asn Pro Met Trp Arg Gly Pro Gln
                885                 890                 895

Arg Leu Pro Val Pro Val Asn Glu Leu Pro His Gly Trp Lys Ala Trp
            900                 905                 910

Gly Lys Ser Tyr Phe Val Arg Ala Ala Lys Thr Asn Asn Ser Phe Val
        915                 920                 925

Val Asp Gly Asp Thr Leu Lys Glu Cys Pro Leu Lys His Arg Ala Trp
    930                 935                 940

Asn Ser Phe Leu Val Glu Asp His Gly Phe Gly Val Phe His Thr Ser
945                 950                 955                 960

Val Trp Leu Lys Val Arg Glu Asp Tyr Ser Leu Glu Cys Asp Pro Ala
                965                 970                 975

Val Ile Gly Thr Ala Val Lys Gly Lys Glu Ala Val His Ser Asp Leu
            980                 985                 990

Gly Tyr Trp Ile Glu Ser Glu Lys  Asn Asp Thr Trp Arg  Leu Lys Arg
        995                 1000                1005

Ala His  Leu Ile Glu Met Lys  Thr Cys Glu Trp Pro  Lys Ser His
    1010                1015                1020

Thr Leu  Trp Thr Asp Gly Ile  Glu Glu Ser Asp Leu  Ile Ile Pro
    1025                1030                1035

Lys Ser  Leu Ala Gly Pro Leu  Ser His His Asn Thr  Arg Glu Gly
    1040                1045                1050

Tyr Arg  Thr Gln Met Lys Gly  Pro Trp His Ser Glu  Glu Leu Glu
    1055                1060                1065

Ile Arg  Phe Glu Glu Cys Pro  Gly Thr Lys Val His  Val Glu Glu
    1070                1075                1080

Thr Cys  Gly Thr Arg Gly Pro  Ser Leu Arg Ser Thr  Thr Ala Ser
    1085                1090                1095

Gly Arg  Val Ile Glu Glu Trp  Cys Cys Arg Glu Cys  Thr Met Pro
    1100                1105                1110

Pro Leu  Ser Phe Arg Ala Lys  Asp Gly Cys Trp Tyr  Gly Met Glu
    1115                1120                1125

Ile Arg  Pro Arg Lys Glu Pro  Glu Ser Asn Leu Val  Arg Ser Met
    1130                1135                1140

Val Thr  Ala Gly Ser Thr Asp  His Met Asp His Phe  Ser Leu Gly
    1145                1150                1155

Val Leu  Val Ile Leu Leu Met  Val Gln Glu Gly Leu  Lys Lys Arg
    1160                1165                1170

Met Thr  Thr Lys Ile Ile Ile  Ser Thr Ser Met Ala  Val Leu Val
    1175                1180                1185

Ala Met  Ile Leu Gly Gly Phe  Ser Met Ser Asp Leu  Ala Lys Leu
    1190                1195                1200

Ala Ile  Leu Met Gly Ala Thr  Phe Ala Glu Met Asn  Thr Gly Gly
    1205                1210                1215

Asp Val  Ala His Leu Ala Leu  Ile Ala Ala Phe Lys  Val Arg Pro
    1220                1225                1230
```

-continued

```
Ala Leu Leu Val Ser Phe Ile Phe Arg Ala Asn Trp Thr Pro Arg
    1235                1240                1245

Glu Ser Met Leu Leu Ala Leu Ala Ser Cys Leu Leu Gln Thr Ala
    1250                1255                1260

Ile Ser Ala Leu Glu Gly Asp Leu Met Val Leu Ile Asn Gly Phe
    1265                1270                1275

Ala Leu Ala Trp Leu Ala Ile Arg Ala Met Val Val Pro Arg Thr
    1280                1285                1290

Asp Asn Ile Thr Leu Ala Ile Leu Ala Ala Leu Thr Pro Leu Ala
    1295                1300                1305

Arg Gly Thr Leu Leu Val Ala Trp Arg Ala Gly Leu Ala Thr Cys
    1310                1315                1320

Gly Gly Phe Met Leu Leu Ser Leu Lys Gly Lys Gly Ser Val Lys
    1325                1330                1335

Lys Asn Leu Pro Phe Val Met Ala Leu Gly Leu Thr Ala Val Arg
    1340                1345                1350

Leu Val Asp Pro Ile Asn Val Val Gly Leu Leu Leu Leu Thr Arg
    1355                1360                1365

Ser Gly Lys Arg Ser Trp Pro Pro Ser Glu Val Leu Thr Ala Val
    1370                1375                1380

Gly Leu Ile Cys Ala Leu Ala Gly Gly Phe Ala Lys Ala Asp Ile
    1385                1390                1395

Glu Met Ala Gly Pro Met Ala Ala Val Gly Leu Leu Ile Val Ser
    1400                1405                1410

Tyr Val Val Ser Gly Lys Ser Val Asp Met Tyr Ile Glu Arg Ala
    1415                1420                1425

Gly Asp Ile Thr Trp Glu Lys Asp Ala Glu Val Thr Gly Asn Ser
    1430                1435                1440

Pro Arg Leu Asp Val Ala Leu Asp Glu Ser Gly Asp Phe Ser Leu
    1445                1450                1455

Val Glu Asp Asp Gly Pro Pro Met Arg Glu Ile Ile Leu Lys Val
    1460                1465                1470

Val Leu Met Thr Ile Cys Gly Met Asn Pro Ile Ala Ile Pro Phe
    1475                1480                1485

Ala Ala Gly Ala Trp Tyr Val Tyr Val Lys Thr Gly Lys Arg Ser
    1490                1495                1500

Gly Ala Leu Trp Asp Val Pro Ala Pro Lys Glu Val Lys Lys Gly
    1505                1510                1515

Glu Thr Thr Asp Gly Val Tyr Arg Val Met Thr Arg Arg Leu Leu
    1520                1525                1530

Gly Ser Thr Gln Val Gly Val Gly Val Met Gln Glu Gly Val Phe
    1535                1540                1545

His Thr Met Trp His Val Thr Lys Gly Ser Ala Leu Arg Ser Gly
    1550                1555                1560

Glu Gly Arg Leu Asp Pro Tyr Trp Gly Asp Val Lys Gln Asp Leu
    1565                1570                1575

Val Ser Tyr Cys Gly Pro Trp Lys Leu Asp Ala Ala Trp Asp Gly
    1580                1585                1590

His Ser Glu Val Gln Leu Leu Ala Val Pro Pro Gly Glu Arg Ala
    1595                1600                1605

Arg Asn Ile Gln Thr Leu Pro Gly Ile Phe Lys Thr Lys Asp Gly
    1610                1615                1620
```

```
Asp Ile  Gly Ala Val Ala Leu  Asp Tyr Pro Ala Gly  Thr Ser Gly
    1625                 1630                 1635

Ser Pro  Ile Leu Asp Lys Cys  Gly Arg Val Ile Gly  Leu Tyr Gly
    1640                 1645                 1650

Asn Gly  Val Val Ile Lys Asn  Gly Ser Tyr Val Ser  Ala Ile Thr
    1655                 1660                 1665

Gln Gly  Arg Arg Glu Glu Glu  Thr Pro Val Glu Cys  Phe Glu Pro
    1670                 1675                 1680

Ser Met  Leu Lys Lys Lys Gln  Leu Thr Val Leu Asp  Leu His Pro
    1685                 1690                 1695

Gly Ala  Gly Lys Thr Arg Arg  Val Leu Pro Glu Ile  Val Arg Glu
    1700                 1705                 1710

Ala Ile  Lys Thr Arg Leu Arg  Thr Val Ile Leu Ala  Pro Thr Arg
    1715                 1720                 1725

Val Val  Ala Ala Glu Met Glu  Glu Ala Leu Arg Gly  Leu Pro Val
    1730                 1735                 1740

Arg Tyr  Met Thr Thr Ala Val  Asn Val Thr His Ser  Gly Thr Glu
    1745                 1750                 1755

Ile Val  Asp Leu Met Cys His  Ala Thr Phe Thr Ser  Arg Leu Leu
    1760                 1765                 1770

Gln Pro  Ile Arg Val Pro Asn  Tyr Asn Leu Tyr Ile  Met Asp Glu
    1775                 1780                 1785

Ala His  Phe Thr Asp Pro Ser  Ser Ile Ala Ala Arg  Gly Tyr Ile
    1790                 1795                 1800

Ser Thr  Arg Val Glu Met Gly  Glu Ala Ala Ala Ile  Phe Met Thr
    1805                 1810                 1815

Ala Thr  Pro Pro Gly Thr Arg  Asp Ala Phe Pro Asp  Ser Asn Ser
    1820                 1825                 1830

Pro Ile  Met Asp Thr Glu Val  Glu Val Pro Glu Arg  Ala Trp Ser
    1835                 1840                 1845

Ser Gly  Phe Asp Trp Val Thr  Asp His Ser Gly Lys  Thr Val Trp
    1850                 1855                 1860

Phe Val  Pro Ser Val Arg Asn  Gly Asn Glu Ile Ala  Ala Cys Leu
    1865                 1870                 1875

Thr Lys  Ala Gly Lys Arg Val  Ile Gln Leu Ser Arg  Lys Thr Phe
    1880                 1885                 1890

Glu Thr  Glu Phe Gln Lys Thr  Lys His Gln Glu Trp  Asp Phe Val
    1895                 1900                 1905

Val Thr  Thr Asp Ile Ser Glu  Met Gly Ala Asn Phe  Lys Ala Asp
    1910                 1915                 1920

Arg Val  Ile Asp Ser Arg Arg  Cys Leu Lys Pro Val  Ile Leu Asp
    1925                 1930                 1935

Gly Glu  Arg Val Ile Leu Ala  Gly Pro Met Pro Val  Thr His Ala
    1940                 1945                 1950

Ser Ala  Ala Gln Arg Arg Gly  Arg Ile Gly Arg Asn  Pro Asn Lys
    1955                 1960                 1965

Pro Gly  Asp Glu Tyr Leu Tyr  Gly Gly Gly Cys Ala  Glu Thr Asp
    1970                 1975                 1980

Glu Asp  His Ala His Trp Leu  Glu Ala Arg Met Leu  Leu Asp Asn
    1985                 1990                 1995

Ile Tyr  Leu Gln Asp Gly Leu  Ile Ala Ser Leu Tyr  Arg Pro Glu
    2000                 2005                 2010

Ala Asp  Lys Val Ala Ala Ile  Glu Gly Glu Phe Lys  Leu Arg Thr
```

-continued

```
    2015                2020                2025

Glu Gln  Arg Lys Thr Phe Val  Glu Leu Met Lys Arg  Gly Asp Leu
    2030                2035                2040

Pro Val  Trp Leu Ala Tyr Gln  Val Ala Ser Ala Gly  Ile Thr Tyr
    2045                2050                2055

Thr Asp  Arg Arg Trp Cys Phe  Asp Gly Thr Thr Asn  Asn Thr Ile
    2060                2065                2070

Met Glu  Asp Ser Val Pro Ala  Glu Val Trp Thr Arg  His Gly Glu
    2075                2080                2085

Lys Arg  Val Leu Lys Pro Arg  Trp Met Asp Ala Arg  Val Cys Ser
    2090                2095                2100

Asp His  Ala Ala Leu Lys Ser  Phe Lys Glu Phe Ala  Ala Gly Lys
    2105                2110                2115

Arg Gly  Ala Ala Phe Gly Val  Met Glu Ala Leu Gly  Thr Leu Pro
    2120                2125                2130

Gly His  Met Thr Glu Arg Phe  Gln Glu Ala Ile Asp  Asn Leu Ala
    2135                2140                2145

Val Leu  Met Arg Ala Glu Thr  Gly Ser Arg Pro Tyr  Lys Ala Ala
    2150                2155                2160

Ala Ala  Gln Leu Pro Glu Thr  Leu Glu Thr Ile Met  Leu Leu Gly
    2165                2170                2175

Leu Leu  Gly Thr Val Ser Leu  Gly Ile Phe Phe Val  Leu Met Arg
    2180                2185                2190

Asn Lys  Gly Ile Gly Lys Met  Gly Phe Gly Met Val  Thr Leu Gly
    2195                2200                2205

Ala Ser  Ala Trp Leu Met Trp  Leu Ser Glu Ile Glu  Pro Ala Arg
    2210                2215                2220

Ile Ala  Cys Val Leu Ile Val  Val Phe Leu Leu Leu  Val Val Leu
    2225                2230                2235

Ile Pro  Glu Pro Glu Lys Gln  Arg Ser Pro Gln Asp  Asn Gln Met
    2240                2245                2250

Ala Ile  Ile Ile Met Val Ala  Val Gly Leu Leu Gly  Leu Ile Thr
    2255                2260                2265

Ala Asn  Glu Leu Gly Trp Leu  Glu Arg Thr Lys Ser  Asp Leu Ser
    2270                2275                2280

His Leu  Met Gly Arg Arg Glu  Glu Gly Ala Thr Ile  Gly Phe Ser
    2285                2290                2295

Met Asp  Ile Asp Leu Arg Pro  Ala Ser Ala Trp Ala  Ile Tyr Ala
    2300                2305                2310

Ala Leu  Thr Thr Phe Ile Thr  Pro Ala Val Gln His  Ala Val Thr
    2315                2320                2325

Thr Ser  Tyr Asn Asn Tyr Ser  Leu Met Ala Met Ala  Thr Gln Ala
    2330                2335                2340

Gly Val  Leu Phe Gly Met Gly  Lys Gly Met Pro Phe  Tyr Ala Trp
    2345                2350                2355

Asp Phe  Gly Val Pro Leu Leu  Met Ile Gly Cys Tyr  Ser Gln Leu
    2360                2365                2370

Thr Pro  Leu Thr Leu Ile Val  Ala Ile Ile Leu Leu  Val Ala His
    2375                2380                2385

Tyr Met  Tyr Leu Ile Pro Gly  Leu Gln Ala Ala Ala  Ala Arg Ala
    2390                2395                2400

Ala Gln  Lys Arg Thr Ala Ala  Gly Ile Met Lys Asn  Pro Val Val
    2405                2410                2415
```

-continued

```
Asp Gly Ile Val Val Thr Asp Ile Asp Thr Met Thr Ile Asp Pro
    2420                2425                2430

Gln Val Glu Lys Lys Met Gly Gln Val Leu Leu Ile Ala Val Ala
    2435                2440                2445

Val Ser Ser Ala Ile Leu Ser Arg Thr Ala Trp Gly Trp Gly Glu
    2450                2455                2460

Ala Gly Ala Leu Ile Thr Ala Ala Thr Ser Thr Leu Trp Glu Gly
    2465                2470                2475

Ser Pro Asn Lys Tyr Trp Asn Ser Ser Thr Ala Thr Ser Leu Cys
    2480                2485                2490

Asn Ile Phe Arg Gly Ser Tyr Leu Ala Gly Ala Ser Leu Ile Tyr
    2495                2500                2505

Thr Val Thr Arg Asn Ala Gly Leu Val Lys Arg Arg Gly Gly Gly
    2510                2515                2520

Thr Gly Glu Thr Leu Gly Glu Lys Trp Lys Ala Arg Leu Asn Gln
    2525                2530                2535

Met Ser Ala Leu Glu Phe Tyr Ser Tyr Lys Lys Ser Gly Ile Thr
    2540                2545                2550

Glu Val Cys Arg Glu Glu Ala Arg Arg Ala Leu Lys Asp Gly Val
    2555                2560                2565

Ala Thr Gly Gly His Ala Val Ser Arg Gly Ser Ala Lys Leu Arg
    2570                2575                2580

Trp Leu Val Glu Arg Gly Tyr Leu Gln Pro Tyr Gly Lys Val Ile
    2585                2590                2595

Asp Leu Gly Cys Gly Arg Gly Gly Trp Ser Tyr Tyr Ala Ala Thr
    2600                2605                2610

Ile Arg Lys Val Gln Glu Val Lys Gly Tyr Thr Lys Gly Gly Pro
    2615                2620                2625

Gly His Glu Glu Pro Val Leu Val Gln Ser Tyr Gly Trp Asn Ile
    2630                2635                2640

Val Arg Leu Lys Ser Gly Val Asp Val Phe His Met Ala Ala Glu
    2645                2650                2655

Pro Cys Asp Thr Leu Leu Cys Asp Ile Gly Glu Ser Ser Ser Ser
    2660                2665                2670

Pro Glu Val Glu Glu Ala Arg Thr Leu Arg Val Leu Ser Met Val
    2675                2680                2685

Gly Asp Trp Leu Glu Lys Arg Pro Gly Ala Phe Cys Ile Lys Val
    2690                2695                2700

Leu Cys Pro Tyr Thr Ser Thr Met Met Glu Thr Leu Glu Arg Leu
    2705                2710                2715

Gln Arg Arg Tyr Gly Gly Gly Leu Val Arg Val Pro Leu Ser Arg
    2720                2725                2730

Asn Ser Thr His Glu Met Tyr Trp Val Ser Gly Ala Lys Ser Asn
    2735                2740                2745

Thr Ile Lys Ser Val Ser Thr Thr Ser Gln Leu Leu Leu Gly Arg
    2750                2755                2760

Met Asp Gly Pro Arg Arg Pro Val Lys Tyr Glu Glu Asp Val Asn
    2765                2770                2775

Leu Gly Ser Gly Thr Arg Ala Val Val Ser Cys Ala Glu Ala Pro
    2780                2785                2790

Asn Met Lys Ile Ile Gly Asn Arg Ile Glu Arg Ile Arg Ser Glu
    2795                2800                2805
```

```
His Ala  Glu Thr Trp Phe Phe  Asp Glu Asn His Pro  Tyr Arg Thr
    2810                 2815                 2820

Trp Ala  Tyr His Gly Ser Tyr  Glu Ala Pro Thr Gln  Gly Ser Ala
    2825                 2830                 2835

Ser Ser  Leu Ile Asn Gly Val  Val Arg Leu Leu Ser  Lys Pro Trp
    2840                 2845                 2850

Asp Val  Val Thr Gly Val Thr  Gly Ile Ala Met Thr  Asp Thr Thr
    2855                 2860                 2865

Pro Tyr  Gly Gln Gln Arg Val  Phe Lys Glu Lys Val  Asp Thr Arg
    2870                 2875                 2880

Val Pro  Asp Pro Gln Glu Gly  Thr Arg Gln Val Met  Ser Met Val
    2885                 2890                 2895

Ser Ser  Trp Leu Trp Lys Glu  Leu Gly Lys His Lys  Arg Pro Arg
    2900                 2905                 2910

Val Cys  Thr Lys Glu Glu Phe  Ile Asn Lys Val Arg  Ser Asn Ala
    2915                 2920                 2925

Ala Leu  Gly Ala Ile Phe Glu  Glu Glu Lys Glu Trp  Lys Thr Ala
    2930                 2935                 2940

Val Glu  Ala Val Asn Asp Pro  Arg Phe Trp Ala Leu  Val Asp Lys
    2945                 2950                 2955

Glu Arg  Glu His His Leu Arg  Gly Glu Cys Gln Ser  Cys Val Tyr
    2960                 2965                 2970

Asn Met  Met Gly Lys Arg Glu  Lys Lys Gln Gly Glu  Phe Gly Lys
    2975                 2980                 2985

Ala Lys  Gly Ser Arg Ala Ile  Trp Tyr Met Trp Leu  Gly Ala Arg
    2990                 2995                 3000

Phe Leu  Glu Phe Glu Ala Leu  Gly Phe Leu Asn Glu  Asp His Trp
    3005                 3010                 3015

Met Gly  Arg Glu Asn Ser Gly  Gly Gly Val Glu Gly  Leu Gly Leu
    3020                 3025                 3030

Gln Arg  Leu Gly Tyr Val Leu  Glu Glu Met Ser Arg  Ile Pro Gly
    3035                 3040                 3045

Gly Arg  Met Tyr Ala Asp Asp  Thr Ala Gly Trp Asp  Thr Arg Ile
    3050                 3055                 3060

Ser Arg  Phe Asp Leu Glu Asn  Glu Ala Leu Ile Thr  Asn Gln Met
    3065                 3070                 3075

Glu Lys  Gly His Arg Ala Leu  Ala Leu Ala Ile Ile  Lys Tyr Thr
    3080                 3085                 3090

Tyr Gln  Asn Lys Val Val Lys  Val Leu Arg Pro Ala  Glu Lys Gly
    3095                 3100                 3105

Lys Thr  Val Met Asp Ile Ile  Ser Arg Gln Asp Gln  Arg Gly Ser
    3110                 3115                 3120

Gly Gln  Val Val Thr Tyr Ala  Leu Asn Thr Phe Thr  Asn Leu Val
    3125                 3130                 3135

Val Gln  Leu Ile Arg Asn Met  Glu Ala Glu Glu Val  Leu Glu Met
    3140                 3145                 3150

Gln Asp  Leu Trp Leu Leu Arg  Arg Ser Glu Lys Val  Thr Asn Trp
    3155                 3160                 3165

Leu Gln  Ser Asn Gly Trp Asp  Arg Leu Lys Arg Met  Ala Val Ser
    3170                 3175                 3180

Gly Asp  Asp Cys Val Val Lys  Pro Ile Asp Asp Arg  Phe Ala His
    3185                 3190                 3195

Ala Leu  Arg Phe Leu Asn Asp  Met Gly Lys Val Arg  Lys Asp Thr
```

-continued

```
    3200                3205                3210

Gln Glu  Trp Lys Pro Ser Thr  Gly Trp Asp Asn Trp  Glu Glu Val
    3215                3220                3225

Pro Phe  Cys Ser His His Phe  Asn Lys Leu His Leu  Lys Asp Gly
    3230                3235                3240

Arg Ser  Ile Val Val Pro Cys  Arg His Gln Asp Glu  Leu Ile Gly
    3245                3250                3255

Arg Ala  Arg Val Ser Pro Gly  Ala Gly Trp Ser Ile  Arg Glu Thr
    3260                3265                3270

Ala Cys  Leu Ala Lys Ser Tyr  Ala Gln Met Trp Gln  Leu Leu Tyr
    3275                3280                3285

Phe His  Arg Arg Asp Leu Arg  Leu Met Ala Asn Ala  Ile Cys Ser
    3290                3295                3300

Ser Val  Pro Val Asp Trp Val  Pro Thr Gly Arg Thr  Thr Trp Ser
    3305                3310                3315

Ile His  Gly Lys Gly Glu Trp  Met Thr Thr Glu Asp  Met Leu Val
    3320                3325                3330

Val Trp  Asn Arg Val Trp Ile  Glu Glu Asn Asp His  Met Glu Asp
    3335                3340                3345

Lys Thr  Pro Val Thr Lys Trp  Thr Asp Ile Pro Tyr  Leu Gly Lys
    3350                3355                3360

Arg Glu  Asp Leu Trp Cys Gly  Ser Leu Ile Gly His  Arg Pro Arg
    3365                3370                3375

Thr Thr  Trp Ala Glu Asn Ile  Lys Asn Thr Val Asn  Met Val Arg
    3380                3385                3390

Arg Ile  Ile Gly Asp Glu Glu  Lys Tyr Met Asp Tyr  Leu Ser Thr
    3395                3400                3405

Gln Val  Arg Tyr Leu Gly Glu  Glu Gly Ser Thr Pro  Gly Val Leu
    3410                3415                3420


<210> SEQ ID NO 3
<211> LENGTH: 669
<212> TYPE: PRT
<213> ORGANISM: Zika virus

<400> SEQUENCE: 3

Thr Arg Arg Gly Ser Ala Tyr Tyr Met Tyr Leu Asp Arg Asn Asp Ala
1               5                   10                  15

Gly Glu Ala Ile Ser Phe Pro Thr Thr Leu Gly Met Asn Lys Cys Tyr
            20                  25                  30

Ile Gln Ile Met Asp Leu Gly His Thr Cys Asp Ala Thr Met Ser Tyr
        35                  40                  45

Glu Cys Pro Met Leu Asp Glu Gly Val Glu Pro Asp Asp Val Asp Cys
    50                  55                  60

Trp Cys Asn Thr Thr Ser Thr Trp Val Val Tyr Gly Thr Cys His His
65                  70                  75                  80

Lys Lys Gly Glu Ala Arg Arg Ser Arg Arg Ala Val Thr Leu Pro Ser
                85                  90                  95

His Ser Thr Arg Lys Leu Gln Thr Arg Ser Gln Thr Trp Leu Glu Ser
            100                 105                 110

Arg Glu Tyr Thr Lys His Leu Ile Arg Val Glu Asn Trp Ile Phe Arg
        115                 120                 125

Asn Pro Gly Phe Ala Leu Ala Ala Ala Ala Ile Ala Trp Leu Leu Gly
    130                 135                 140
```

-continued

```
Ser Ser Thr Ser Gln Lys Val Ile Tyr Leu Val Met Ile Leu Leu Ile
145                 150                 155                 160

Ala Pro Ala Tyr Ser Ile Arg Cys Ile Gly Val Ser Asn Arg Asp Phe
                165                 170                 175

Val Glu Gly Met Ser Gly Gly Thr Trp Val Asp Val Val Leu Glu His
            180                 185                 190

Gly Gly Cys Val Thr Val Met Ala Gln Asp Lys Pro Thr Val Asp Ile
        195                 200                 205

Glu Leu Val Thr Thr Thr Val Ser Asn Met Ala Glu Val Arg Ser Tyr
    210                 215                 220

Cys Tyr Glu Ala Ser Ile Ser Asp Met Ala Ser Asp Ser Arg Cys Pro
225                 230                 235                 240

Thr Gln Gly Glu Ala Tyr Leu Asp Lys Gln Ser Asp Thr Gln Tyr Val
                245                 250                 255

Cys Lys Arg Thr Leu Val Asp Arg Gly Trp Gly Asn Gly Cys Gly Leu
            260                 265                 270

Phe Gly Lys Gly Ser Leu Val Thr Cys Ala Lys Phe Ala Cys Ser Lys
        275                 280                 285

Lys Met Thr Gly Lys Ser Ile Gln Pro Glu Asn Leu Glu Tyr Arg Ile
    290                 295                 300

Met Leu Ser Val His Gly Ser Gln His Ser Gly Met Ile Val Asn Asp
305                 310                 315                 320

Thr Gly His Glu Thr Asp Glu Asn Arg Ala Lys Val Glu Ile Thr Pro
                325                 330                 335

Asn Ser Pro Arg Ala Glu Ala Thr Leu Gly Gly Phe Gly Ser Leu Gly
            340                 345                 350

Leu Asp Cys Glu Pro Arg Thr Gly Leu Asp Phe Ser Asp Leu Tyr Tyr
        355                 360                 365

Leu Thr Met Asn Asn Lys His Trp Leu Val His Lys Glu Trp Phe His
    370                 375                 380

Asp Ile Pro Leu Pro Trp His Ala Gly Ala Asp Thr Gly Thr Pro His
385                 390                 395                 400

Trp Asn Asn Lys Glu Ala Leu Val Glu Phe Lys Asp Ala His Ala Lys
                405                 410                 415

Arg Gln Thr Val Val Val Leu Gly Ser Gln Glu Gly Ala Val His Thr
            420                 425                 430

Ala Leu Ala Gly Ala Leu Glu Ala Glu Met Asp Gly Ala Lys Gly Arg
        435                 440                 445

Leu Ser Ser Gly His Leu Lys Cys Arg Leu Lys Met Asp Lys Leu Arg
    450                 455                 460

Leu Lys Gly Val Ser Tyr Ser Leu Cys Thr Ala Ala Phe Thr Phe Thr
465                 470                 475                 480

Lys Ile Pro Ala Glu Thr Leu His Gly Thr Val Thr Val Glu Val Gln
                485                 490                 495

Tyr Ala Gly Thr Asp Gly Pro Cys Lys Val Pro Ala Gln Met Ala Val
            500                 505                 510

Asp Met Gln Thr Leu Thr Pro Val Gly Arg Leu Ile Thr Ala Asn Pro
        515                 520                 525

Val Ile Thr Glu Ser Thr Glu Asn Ser Lys Met Met Leu Glu Leu Asp
    530                 535                 540

Pro Pro Phe Gly Asp Ser Tyr Ile Val Ile Gly Val Gly Glu Lys Lys
545                 550                 555                 560

Ile Thr His His Trp His Arg Ser Gly Ser Thr Ile Gly Lys Ala Phe
```

```
                565                 570                 575

Glu Ala Thr Val Arg Gly Ala Lys Arg Met Ala Val Leu Gly Asp Thr
            580                 585                 590

Ala Trp Asp Phe Gly Ser Val Gly Gly Ala Leu Asn Ser Leu Gly Lys
        595                 600                 605

Gly Ile His Gln Ile Phe Gly Ala Ala Phe Lys Ser Leu Phe Gly Gly
    610                 615                 620

Met Ser Trp Phe Ser Gln Ile Leu Ile Gly Thr Leu Leu Met Trp Leu
625                 630                 635                 640

Gly Leu Asn Ala Lys Asn Gly Ser Ile Ser Leu Met Cys Leu Ala Leu
                645                 650                 655

Gly Gly Val Leu Ile Phe Leu Ser Thr Ala Val Ser Ala
            660                 665


<210> SEQ ID NO 4
<211> LENGTH: 24
<212> TYPE: PRT
<213> ORGANISM: Zika virus

<400> SEQUENCE: 4

Met Gly Lys Arg Ser Ala Gly Ser Ile Met Trp Leu Ala Ser Leu Ala
1               5                   10                  15

Val Val Ile Ala Cys Ala Gly Ala
            20


<210> SEQ ID NO 5
<211> LENGTH: 693
<212> TYPE: PRT
<213> ORGANISM: Zika virus

<400> SEQUENCE: 5

Met Gly Lys Arg Ser Ala Gly Ser Ile Met Trp Leu Ala Ser Leu Ala
1               5                   10                  15

Val Val Ile Ala Cys Ala Gly Ala Thr Arg Arg Gly Ser Ala Tyr Tyr
            20                  25                  30

Met Tyr Leu Asp Arg Asn Asp Ala Gly Glu Ala Ile Ser Phe Pro Thr
        35                  40                  45

Thr Leu Gly Met Asn Lys Cys Tyr Ile Gln Ile Met Asp Leu Gly His
    50                  55                  60

Thr Cys Asp Ala Thr Met Ser Tyr Glu Cys Pro Met Leu Asp Glu Gly
65                  70                  75                  80

Val Glu Pro Asp Asp Val Asp Cys Trp Cys Asn Thr Thr Ser Thr Trp
                85                  90                  95

Val Val Tyr Gly Thr Cys His His Lys Lys Gly Glu Ala Arg Arg Ser
            100                 105                 110

Arg Arg Ala Val Thr Leu Pro Ser His Ser Thr Arg Lys Leu Gln Thr
        115                 120                 125

Arg Ser Gln Thr Trp Leu Glu Ser Arg Glu Tyr Thr Lys His Leu Ile
    130                 135                 140

Arg Val Glu Asn Trp Ile Phe Arg Asn Pro Gly Phe Ala Leu Ala Ala
145                 150                 155                 160

Ala Ala Ile Ala Trp Leu Leu Gly Ser Ser Thr Ser Gln Lys Val Ile
                165                 170                 175

Tyr Leu Val Met Ile Leu Leu Ile Ala Pro Ala Tyr Ser Ile Arg Cys
            180                 185                 190

Ile Gly Val Ser Asn Arg Asp Phe Val Glu Gly Met Ser Gly Gly Thr
```

-continued

```
        195                 200                 205

Trp Val Asp Val Val Leu Glu His Gly Gly Cys Val Thr Val Met Ala
    210                 215                 220

Gln Asp Lys Pro Thr Val Asp Ile Glu Leu Val Thr Thr Thr Val Ser
225                 230                 235                 240

Asn Met Ala Glu Val Arg Ser Tyr Cys Tyr Glu Ala Ser Ile Ser Asp
                245                 250                 255

Met Ala Ser Asp Ser Arg Cys Pro Thr Gln Gly Glu Ala Tyr Leu Asp
            260                 265                 270

Lys Gln Ser Asp Thr Gln Tyr Val Cys Lys Arg Thr Leu Val Asp Arg
        275                 280                 285

Gly Trp Gly Asn Gly Cys Gly Leu Phe Gly Lys Gly Ser Leu Val Thr
    290                 295                 300

Cys Ala Lys Phe Ala Cys Ser Lys Lys Met Thr Gly Lys Ser Ile Gln
305                 310                 315                 320

Pro Glu Asn Leu Glu Tyr Arg Ile Met Leu Ser Val His Gly Ser Gln
                325                 330                 335

His Ser Gly Met Ile Val Asn Asp Thr Gly His Glu Thr Asp Glu Asn
            340                 345                 350

Arg Ala Lys Val Glu Ile Thr Pro Asn Ser Pro Arg Ala Glu Ala Thr
        355                 360                 365

Leu Gly Gly Phe Gly Ser Leu Gly Leu Asp Cys Glu Pro Arg Thr Gly
    370                 375                 380

Leu Asp Phe Ser Asp Leu Tyr Tyr Leu Thr Met Asn Asn Lys His Trp
385                 390                 395                 400

Leu Val His Lys Glu Trp Phe His Asp Ile Pro Leu Pro Trp His Ala
                405                 410                 415

Gly Ala Asp Thr Gly Thr Pro His Trp Asn Asn Lys Glu Ala Leu Val
            420                 425                 430

Glu Phe Lys Asp Ala His Ala Lys Arg Gln Thr Val Val Val Leu Gly
        435                 440                 445

Ser Gln Glu Gly Ala Val His Thr Ala Leu Ala Gly Ala Leu Glu Ala
    450                 455                 460

Glu Met Asp Gly Ala Lys Gly Arg Leu Ser Ser Gly His Leu Lys Cys
465                 470                 475                 480

Arg Leu Lys Met Asp Lys Leu Arg Leu Lys Gly Val Ser Tyr Ser Leu
                485                 490                 495

Cys Thr Ala Ala Phe Thr Phe Thr Lys Ile Pro Ala Glu Thr Leu His
            500                 505                 510

Gly Thr Val Thr Val Glu Val Gln Tyr Ala Gly Thr Asp Gly Pro Cys
        515                 520                 525

Lys Val Pro Ala Gln Met Ala Val Asp Met Gln Thr Leu Thr Pro Val
    530                 535                 540

Gly Arg Leu Ile Thr Ala Asn Pro Val Ile Thr Glu Ser Thr Glu Asn
545                 550                 555                 560

Ser Lys Met Met Leu Glu Leu Asp Pro Pro Phe Gly Asp Ser Tyr Ile
                565                 570                 575

Val Ile Gly Val Gly Glu Lys Lys Ile Thr His His Trp His Arg Ser
            580                 585                 590

Gly Ser Thr Ile Gly Lys Ala Phe Glu Ala Thr Val Arg Gly Ala Lys
        595                 600                 605

Arg Met Ala Val Leu Gly Asp Thr Ala Trp Asp Phe Gly Ser Val Gly
    610                 615                 620
```

Gly Ala Leu Asn Ser Leu Gly Lys Gly Ile His Gln Ile Phe Gly Ala
625 630 635 640

Ala Phe Lys Ser Leu Phe Gly Gly Met Ser Trp Phe Ser Gln Ile Leu
645 650 655

Ile Gly Thr Leu Leu Met Trp Leu Gly Leu Asn Ala Lys Asn Gly Ser
660 665 670

Ile Ser Leu Met Cys Leu Ala Leu Gly Gly Val Leu Ile Phe Leu Ser
675 680 685

Thr Ala Val Ser Ala
690

<210> SEQ ID NO 6
<211> LENGTH: 693
<212> TYPE: PRT
<213> ORGANISM: Zika virus

<400> SEQUENCE: 6

Met Gly Lys Arg Ser Ala Gly Ser Ile Met Trp Leu Ala Ser Leu Ala
1 5 10 15

Val Val Ile Ala Cys Ala Gly Ala Thr Arg Arg Gly Ser Ala Tyr Tyr
20 25 30

Met Tyr Leu Asp Arg Asn Asp Ala Gly Glu Ala Ile Ser Phe Pro Thr
35 40 45

Thr Leu Gly Met Asn Lys Cys Tyr Ile Gln Ile Met Asp Leu Gly His
50 55 60

Thr Cys Asp Ala Thr Met Ser Tyr Glu Cys Pro Met Leu Asp Glu Gly
65 70 75 80

Val Glu Pro Asp Asp Val Asp Cys Trp Cys Asn Thr Thr Ser Thr Trp
85 90 95

Val Val Tyr Gly Thr Cys His His Lys Lys Gly Glu Ala Arg Arg Ser
100 105 110

Arg Arg Ala Val Thr Leu Pro Ser His Ser Thr Arg Lys Leu Gln Thr
115 120 125

Arg Ser Gln Thr Trp Leu Glu Ser Arg Glu Tyr Thr Lys His Leu Ile
130 135 140

Arg Val Glu Asn Trp Ile Phe Arg Asn Pro Gly Phe Ala Leu Ala Ala
145 150 155 160

Ala Ala Ile Ala Trp Leu Leu Gly Ser Ser Thr Ser Gln Lys Val Ile
165 170 175

Tyr Leu Val Met Ile Leu Leu Ile Ala Pro Ala Tyr Ser Ile Arg Cys
180 185 190

Ile Gly Val Ser Asn Arg Asp Phe Val Glu Gly Met Ser Gly Gly Thr
195 200 205

Trp Val Asp Val Val Leu Glu His Gly Gly Cys Val Thr Val Met Ala
210 215 220

Gln Asp Lys Pro Thr Val Asp Ile Glu Leu Val Thr Thr Thr Val Ser
225 230 235 240

Asn Met Ala Glu Val Arg Ser Tyr Cys Tyr Glu Ala Ser Ile Ser Asp
245 250 255

Met Ala Ser Asp Ser Arg Cys Pro Thr Gln Gly Glu Ala Tyr Leu Asp
260 265 270

Lys Gln Ser Asp Thr Gln Tyr Val Cys Lys Arg Thr Leu Val Asp Arg
275 280 285

Gly Trp Gly Asn Gly Cys Gly Leu Phe Gly Lys Gly Ser Leu Val Thr

```
    290                 295                 300

Cys Ala Lys Phe Ala Cys Ser Lys Lys Met Thr Gly Lys Ser Ile Gln
305                 310                 315                 320

Pro Glu Asn Leu Glu Tyr Arg Ile Met Leu Ser Val His Gly Ser Gln
                325                 330                 335

His Ser Gly Met Ile Val Asn Asp Thr Gly His Glu Thr Asp Glu Asn
            340                 345                 350

Arg Ala Lys Val Glu Ile Thr Pro Asn Ser Pro Arg Ala Glu Ala Thr
        355                 360                 365

Leu Gly Gly Phe Gly Ser Leu Gly Leu Asp Cys Glu Pro Arg Thr Gly
    370                 375                 380

Leu Asp Phe Ser Asp Leu Tyr Tyr Leu Thr Met Asn Asn Lys His Trp
385                 390                 395                 400

Leu Val His Lys Glu Trp Phe His Asp Ile Pro Leu Pro Trp His Ala
                405                 410                 415

Gly Ala Asp Thr Gly Thr Pro His Trp Asn Asn Lys Glu Ala Leu Val
            420                 425                 430

Glu Phe Lys Asp Ala His Ala Lys Arg Gln Thr Val Val Val Leu Gly
        435                 440                 445

Ser Gln Glu Gly Ala Val His Thr Ala Leu Ala Gly Ala Leu Glu Ala
    450                 455                 460

Glu Met Asp Gly Ala Lys Gly Arg Leu Ser Ser Gly His Leu Lys Cys
465                 470                 475                 480

Arg Leu Lys Met Asp Lys Leu Arg Leu Lys Gly Val Ser Tyr Ser Leu
                485                 490                 495

Cys Thr Ala Ala Phe Thr Phe Thr Lys Ile Pro Ala Glu Thr Leu His
            500                 505                 510

Gly Thr Val Thr Val Glu Val Gln Tyr Ala Gly Thr Asp Gly Pro Cys
        515                 520                 525

Lys Val Pro Ala Gln Met Ala Val Asp Met Gln Thr Leu Thr Pro Val
    530                 535                 540

Gly Arg Leu Ile Thr Ala Asn Pro Val Ile Thr Glu Ser Thr Glu Asn
545                 550                 555                 560

Ser Lys Met Met Leu Glu Leu Asp Pro Pro Phe Gly Asp Ser Tyr Ile
                565                 570                 575

Val Ile Gly Val Gly Glu Lys Lys Ile Thr His His Trp His Arg Ser
            580                 585                 590

Gly Ser Thr Ile Gly Lys Ala Phe Glu Ala Thr Val Arg Gly Ala Lys
        595                 600                 605

Arg Met Ala Val Leu Gly Asp Thr Ala Trp Asp Phe Gly Ser Val Gly
    610                 615                 620

Gly Ala Leu Asn Ser Leu Gly Lys Gly Ile His Gln Ile Phe Gly Ala
625                 630                 635                 640

Ala Phe Lys Ser Leu Phe Gly Gly Met Ser Trp Phe Ser Gln Ile Leu
                645                 650                 655

Ile Gly Thr Leu Leu Met Trp Leu Gly Leu Asn Ala Lys Asn Gly Ser
            660                 665                 670

Ile Ser Leu Met Cys Leu Ala Leu Gly Gly Val Leu Ile Phe Leu Ser
        675                 680                 685

Thr Ala Val Ser Ala
    690
```

<210> SEQ ID NO 7

-continued

<211> LENGTH: 2085
<212> TYPE: DNA
<213> ORGANISM: Zika virus

<400> SEQUENCE: 7
atgggaaaac gatcagccgg atctataatg tggcttgcaa gtctagctgt tgttattgcc 60
tgtgcgggag cgacgcgtag aggatccgcg tattatatgt atctagatcg taacgacgca 120
ggagaggcta tttcattccc tacgactttg ggtatgaata agtgctacat tcagatcatg 180
gacttaggac acacctgtga tgccacgatg tcctacgagt gccctatgct agatgaagga 240
gtagaaccag atgacgtaga ttgttggtgc aatacgactt ccacatgggt tgtttatggt 300
acctgtcacc acaagaaagg tgaagctcgt agatctagac gtgccgtgac tcttcccagt 360
cattccacaa gaaaacttca aacgcgttct caaacttggc tagaaagtcg tgaatacacg 420
aagcatttaa ttcgtgtaga gaactggatc tttcgtaacc caggtttcgc tctagcggcc 480
gccgcgatag cttggttatt gggttcatca acttcccaaa aggtcattta cttagtcatg 540
attcttctta tagccccggc gtactctata cgttgcatcg gtgtatcgaa tcgagacttt 600
gtggaaggaa tgtccggagg aacctgggtt gatgtagtcc tagagcatgg tggatgtgtc 660
acagtcatgg cccaggataa acctacggta gacatcgaat tggttacgac aacagtcagt 720
aatatggcag aggtaagatc gtattgttat gaagcatcca tttctgacat ggcgtccgat 780
tcacgatgcc ctacccaggg tgaagcatat ctagataaac agagtgatac acagtacgtg 840
tgtaagagaa ccctagttga cagaggatgg ggtaacggtt gcggattgtt tggtaaagga 900
agtctagtga cgtgcgccaa gttcgcgtgc tcaaagaaga tgacgggaaa gtcaatccaa 960
ccggagaatc ttgaataccg tatcatgtta tcagtgcacg gatctcagca ttcaggaatg 1020
atagtaaacg acactggaca tgagacggac gagaacagag ccaaggtcga aatcacgccc 1080
aattcacctc gtgcagaggc aacccttggt ggatttggat cgctaggtct tgactgcgaa 1140
ccgcgaacgg gattggactt ttcggatttg tattatctaa ctatgaataa caaacattgg 1200
ctagttcata aggaatggtt ccatgatatt ccccttccct ggcatgcagg agctgatacc 1260
ggaacacctc attggaacaa caaggaagca cttgtcgaat ttaaagatgc gcatgcgaag 1320
cgacaaaccg tagttgtgtt gggttcccaa gagggtgctg tgcacacagc cctagcaggt 1380
gcgcttgagg cggaaatgga tggagcaaaa ggtagactat cttccggaca cttaaaatgc 1440
agattaaaga tggacaaact tcgactaaaa ggagtaagtt attcattatg tacggccgca 1500
tttactttta ccaaaatacc agccgagacg ttgcacggta cggttaccgt ggaggtacag 1560
tatgcgggta cagatggtcc gtgcaaggtg cccgcccaaa tggcagttga catgcagact 1620
ttgacgcccg tgggtcgttt gatcaccgcc aaccccgtca tcacggagtc tacggaaaac 1680
tccaagatga tgttagagct agaccctcca ttcggtgact cgtacatagt cattggtgtg 1740
ggagagaaga agattacgca tcattggcac agatcgggat caacaatcgg taaggcgttt 1800
gaggcgacag tgcgaggtgc taagagaatg gcggtccttg gtgatacggc gtgggatttt 1860
ggatctgtcg gaggtgctct aaatagtctt ggaaaaggta tccaccagat atttggagca 1920
gcgtttaaat cattatttgg tggaatgagt tggttcagtc aaatacttat cggaacgctt 1980
cttatgtggt tgggattgaa tgctaagaac ggaagtattt ccttgatgtg tcttgctttg 2040
ggaggagtac ttatcttcct atcaacagcc gtctcagcat aataa 2085

<210> SEQ ID NO 8
<211> LENGTH: 353

<212> TYPE: PRT
<213> ORGANISM: Zika virus

<400> SEQUENCE: 8

```
Val Gly Cys Ser Val Asp Phe Ser Lys Lys Glu Thr Arg Cys Gly Thr
1               5                   10                  15

Gly Val Phe Val Tyr Asn Asp Val Glu Ala Trp Arg Asp Arg Tyr Lys
            20                  25                  30

Tyr His Pro Asp Ser Pro Arg Arg Leu Ala Ala Ala Val Lys Gln Ala
        35                  40                  45

Trp Glu Asp Gly Ile Cys Gly Ile Ser Ser Val Ser Arg Met Glu Asn
    50                  55                  60

Ile Met Trp Arg Ser Val Glu Gly Glu Leu Asn Ala Ile Leu Glu Glu
65                  70                  75                  80

Asn Gly Val Gln Leu Thr Val Val Val Gly Ser Val Lys Asn Pro Met
                85                  90                  95

Trp Arg Gly Pro Gln Arg Leu Pro Val Pro Val Asn Glu Leu Pro His
            100                 105                 110

Gly Trp Lys Ala Trp Gly Lys Ser Tyr Phe Val Arg Ala Ala Lys Thr
        115                 120                 125

Asn Asn Ser Phe Val Val Asp Gly Asp Thr Leu Lys Glu Cys Pro Leu
    130                 135                 140

Lys His Arg Ala Trp Asn Ser Phe Leu Val Glu Asp His Gly Phe Gly
145                 150                 155                 160

Val Phe His Thr Ser Val Trp Leu Lys Val Arg Glu Asp Tyr Ser Leu
                165                 170                 175

Glu Cys Asp Pro Ala Val Ile Gly Thr Ala Val Lys Gly Lys Glu Ala
            180                 185                 190

Val His Ser Asp Leu Gly Tyr Trp Ile Glu Ser Glu Lys Asn Asp Thr
        195                 200                 205

Trp Arg Leu Lys Arg Ala His Leu Ile Glu Met Lys Thr Cys Glu Trp
    210                 215                 220

Pro Lys Ser His Thr Leu Trp Thr Asp Gly Ile Glu Glu Ser Asp Leu
225                 230                 235                 240

Ile Ile Pro Lys Ser Leu Ala Gly Pro Leu Ser His His Asn Thr Arg
                245                 250                 255

Glu Gly Tyr Arg Thr Gln Met Lys Gly Pro Trp His Ser Glu Glu Leu
            260                 265                 270

Glu Ile Arg Phe Glu Glu Cys Pro Gly Thr Lys Val His Val Glu Glu
        275                 280                 285

Thr Cys Gly Thr Arg Gly Pro Ser Leu Arg Ser Thr Thr Ala Ser Gly
    290                 295                 300

Arg Val Ile Glu Glu Trp Cys Cys Arg Glu Cys Thr Met Pro Pro Leu
305                 310                 315                 320

Ser Phe Arg Ala Lys Asp Gly Cys Trp Tyr Gly Met Glu Ile Arg Pro
                325                 330                 335

Arg Lys Glu Pro Glu Ser Asn Leu Val Arg Ser Met Val Thr Ala Gly
            340                 345                 350

Ser
```

<210> SEQ ID NO 9
<211> LENGTH: 1110
<212> TYPE: DNA
<213> ORGANISM: Zika virus

-continued

<400> SEQUENCE: 9

```
atgaaatgcc ttctatactt agccttcttg ttcataggtg ttaactgcga cgttggatgt      60
tccgtggatt tctcaaagaa ggagactcgt tgcggtacgg gagtgtttgt gtataatgac     120
gtggaagcgt ggcgtgacag atataagtat catccagatt cgccacgtcg tcttgcggct     180
gctgtgaagc aagcgtggga ggatggtatc tgtggtattt cctccgtatc tcgaatggag     240
aatattatgt ggcgtagtgt tgagggagaa ctaaacgcaa tcctagagga gaacggagtc     300
caacttaccg tcgtcgttgg atccgtaaag aatcctatgt ggcgaggtcc ccagcgttta     360
cctgtccccg tcaatgagtt gccacatggt tggaaagcgt ggggaaagtc ctacttcgta     420
cgtgccgcga agaccaataa ttcatttgtg gtagacggag atacattgaa ggagtgccct     480
ttaaagcacc gtgcttggaa ctctttctta gtagaagatc acggtttcgg agtatttcac     540
acatcggtat ggctaaaggt acgtgaagat tactcgcttg aatgtgaccc agctgttata     600
ggtacggcgg tcaaaggtaa ggaagcagtg catagtgacc ttggatattg gattgagtca     660
gagaagaatg acacatggag actaaagaga gcacatctta tagaaatgaa aacttgcgag     720
tggcccaaat cacacacttt gtggacagac ggtattgaag aatccgatct tatcatacct     780
aaatcgcttg caggaccact atcgcatcac aacacgagag agggttatag aacccagatg     840
aagggacctt ggcatagtga ggagcttgaa atacgttttg aggagtgtcc cggtactaag     900
gtgcatgtcg aggaaacttg cggtactcgt ggaccatcgc tacgttcaac aacagcctcg     960
ggtcgagtca ttgaggaatg gtgctgtcgt gaatgtacca tgccgccttt atcctttcgt    1020
gcgaaagacg gatgttggta tggtatggaa attcgtccca gaaaagagcc ggagtcgaac    1080
ctagtaagat ccatggtcac cgcgtaataa                                     1110
```

<210> SEQ ID NO 10
<211> LENGTH: 597
<212> TYPE: DNA
<213> ORGANISM: Zika virus

<400> SEQUENCE: 10

```
atgaaatgcc ttctatactt agccttcttg ttcataggtg ttaactgccg tgaagattac      60
tcgcttgaat gtgacccagc tgttataggt acggcggtca aaggtaagga agcagtgcat     120
agtgaccttg gatattggat tgagtcagag aagaatgaca catggagact aaagagagca     180
catcttatag aaatgaaaac ttgcgagtgg cccaaatcac acactttgtg gacagacggt     240
attgaagaat ccgatcttat catacctaaa tcgcttgcag gaccactatc gcatcacaac     300
acgagagagg gttatagaac ccagatgaag ggaccttggc atagtgagga gcttgaaata     360
cgttttgagg agtgtcccgg tactaaggtg catgtcgagg aaacttgcgg tactcgtgga     420
ccatcgctac gttcaacaac agcctcgggt cgagtcattg aggaatggtg ctgtcgtgaa     480
tgtaccatgc cgcctttatc ctttcgtgcg aaagacggat gttggtatgg tatggaaatt     540
cgtcccagaa aagagccgga gtcgaaccta gtaagatcca tggtcaccgc gtaataa       597
```

<210> SEQ ID NO 11
<211> LENGTH: 693
<212> TYPE: PRT
<213> ORGANISM: Zika virus

<400> SEQUENCE: 11

```
Met Gly Lys Arg Ser Ala Gly Ser Ile Met Trp Leu Ala Ser Leu Ala
1               5                   10                  15
```

-continued

```
Val Val Ile Ala Cys Ala Gly Ala Thr Arg Arg Gly Ser Ala Tyr Tyr
            20                  25                  30

Met Tyr Leu Asp Arg Asn Asp Ala Gly Glu Ala Ile Ser Phe Pro Thr
        35                  40                  45

Thr Leu Gly Met Asn Lys Cys Tyr Ile Gln Ile Met Asp Leu Gly His
    50                  55                  60

Thr Cys Asp Ala Thr Met Ser Tyr Glu Cys Pro Met Leu Asp Glu Gly
65                  70                  75                  80

Val Glu Pro Asp Asp Val Asp Cys Trp Cys Asn Thr Thr Ser Thr Trp
                85                  90                  95

Val Val Tyr Gly Thr Cys His His Lys Lys Gly Glu Ala Arg Arg Ser
            100                 105                 110

Arg Arg Ala Val Thr Leu Pro Ser His Ser Thr Arg Lys Leu Gln Thr
        115                 120                 125

Arg Ser Gln Thr Trp Leu Glu Ser Arg Glu Tyr Thr Lys His Leu Ile
    130                 135                 140

Arg Val Glu Asn Trp Ile Phe Arg Asn Pro Gly Phe Ala Leu Ala Ala
145                 150                 155                 160

Ala Ala Ile Ala Trp Leu Leu Gly Ser Ser Thr Ser Gln Lys Val Ile
                165                 170                 175

Tyr Leu Val Met Ile Leu Leu Ile Ala Pro Ala Tyr Ser Ile Arg Cys
            180                 185                 190

Ile Gly Val Ser Asn Arg Asp Phe Val Glu Gly Met Ser Gly Gly Thr
        195                 200                 205

Trp Val Asp Val Val Leu Glu His Gly Gly Cys Val Thr Val Met Ala
    210                 215                 220

Gln Asp Lys Pro Thr Val Asp Ile Glu Leu Val Thr Thr Thr Val Ser
225                 230                 235                 240

Asn Met Ala Glu Val Arg Ser Tyr Cys Tyr Glu Ala Ser Ile Ser Asp
                245                 250                 255

Met Ala Ser Asp Ser Arg Cys Pro Thr Gln Gly Glu Ala Tyr Leu Asp
            260                 265                 270

Lys Gln Ser Asp Thr Gln Tyr Val Cys Lys Arg Thr Leu Val Asp Arg
        275                 280                 285

Gly Trp Gly Asn Gly Cys Gly Leu Phe Gly Lys Gly Ser Leu Val Thr
    290                 295                 300

Cys Ala Lys Phe Ala Cys Ser Lys Lys Met Thr Gly Lys Ser Ile Gln
305                 310                 315                 320

Pro Glu Asn Leu Glu Tyr Arg Ile Met Leu Ser Val His Gly Ser Gln
                325                 330                 335

His Ser Gly Met Ile Val Asn Asp Thr Gly His Glu Thr Asp Glu Asn
            340                 345                 350

Arg Ala Lys Val Glu Ile Thr Pro Asn Ser Pro Arg Ala Glu Ala Thr
        355                 360                 365

Leu Gly Gly Phe Gly Ser Leu Gly Leu Asp Cys Glu Pro Arg Thr Gly
    370                 375                 380

Leu Asp Phe Ser Asp Leu Tyr Tyr Leu Thr Met Asn Asn Lys His Trp
385                 390                 395                 400

Leu Val His Lys Glu Trp Phe His Asp Ile Pro Leu Pro Trp His Ala
                405                 410                 415

Gly Ala Asp Thr Gly Thr Pro His Trp Asn Asn Lys Glu Ala Leu Val
            420                 425                 430

Glu Phe Lys Asp Ala His Ala Lys Arg Gln Thr Val Val Val Leu Gly
```

```
        435                 440                 445

Ser Gln Glu Gly Ala Val His Thr Ala Leu Ala Gly Ala Leu Glu Ala
    450                 455                 460

Glu Met Asp Gly Ala Lys Gly Arg Leu Ser Ser Gly His Leu Lys Cys
465                 470                 475                 480

Arg Leu Lys Met Asp Lys Leu Arg Leu Lys Gly Val Ser Tyr Ser Leu
                485                 490                 495

Cys Thr Ala Ala Phe Thr Phe Thr Lys Ile Pro Ala Glu Thr Leu His
            500                 505                 510

Gly Thr Val Thr Val Glu Val Gln Tyr Ala Gly Thr Asp Gly Pro Cys
        515                 520                 525

Lys Val Pro Ala Gln Met Ala Val Asp Met Gln Thr Leu Thr Pro Val
    530                 535                 540

Gly Arg Leu Ile Thr Ala Asn Pro Val Ile Thr Glu Ser Thr Glu Asn
545                 550                 555                 560

Ser Lys Met Met Leu Glu Leu Asp Pro Pro Phe Gly Asp Ser Tyr Ile
                565                 570                 575

Val Ile Gly Val Gly Glu Lys Lys Ile Thr His His Trp His Arg Ser
            580                 585                 590

Gly Ser Thr Ile Gly Lys Ala Phe Glu Ala Thr Val Arg Gly Ala Lys
        595                 600                 605

Arg Met Ala Val Leu Gly Asp Thr Ala Trp Asp Phe Gly Ser Val Gly
    610                 615                 620

Gly Ala Leu Asn Ser Leu Gly Lys Gly Ile His Gln Ile Phe Gly Ala
625                 630                 635                 640

Ala Phe Lys Ser Leu Phe Gly Gly Met Ser Trp Phe Ser Gln Ile Leu
                645                 650                 655

Ile Gly Thr Leu Leu Met Trp Leu Gly Leu Asn Ala Lys Asn Gly Ser
            660                 665                 670

Ile Ser Leu Met Cys Leu Ala Leu Gly Gly Val Leu Ile Phe Leu Ser
        675                 680                 685

Thr Ala Val Ser Ala
    690


<210> SEQ ID NO 12
<211> LENGTH: 28
<212> TYPE: DNA
<213> ORGANISM: Zika virus

<400> SEQUENCE: 12

gaaagcgaga aataatcata aataagcc                                        28


<210> SEQ ID NO 13
<211> LENGTH: 28
<212> TYPE: DNA
<213> ORGANISM: Zika virus

<400> SEQUENCE: 13

gaaagcgaga aataatcata aataagcc                                        28


<210> SEQ ID NO 14
<211> LENGTH: 24
<212> TYPE: DNA
<213> ORGANISM: Zika virus

<400> SEQUENCE: 14

gtctataaac ctcgtcgcaa attt                                            24
```

<210> SEQ ID NO 15
<211> LENGTH: 24
<212> TYPE: DNA
<213> ORGANISM: Zika virus

<400> SEQUENCE: 15
cagatatttg gagcagcgtt taaa 24

<210> SEQ ID NO 16
<211> LENGTH: 40
<212> TYPE: DNA
<213> ORGANISM: Zika virus

<400> SEQUENCE: 16
gactcagtct aggaaagcga gaaataatca taaataagcc 40

<210> SEQ ID NO 17
<211> LENGTH: 40
<212> TYPE: DNA
<213> ORGANISM: Zika virus

<400> SEQUENCE: 17
tactagtcga ctactattta aacgctgctc caaatatctg 40

<210> SEQ ID NO 18
<211> LENGTH: 1989
<212> TYPE: DNA
<213> ORGANISM: Zika virus

<400> SEQUENCE: 18
gactcagtct aggaaagcga gaaataatca taaataagcc cgggatggga aaacgatcag 60
ccggatctat aatgtggctt gcaagtctag ctgttgttat tgcctgtgcg ggagcgacgc 120
gtagaggatc cgcgtattat atgtatctag atcgtaacga cgcaggagag gctatttcat 180
tccctacgac tttgggtatg aataagtgct acattcagat catggactta ggacacacct 240
gtgatgccac gatgtcctac gagtgcccta tgctagatga aggagtagaa ccagatgacg 300
tagattgttg gtgcaatacg acttccacat gggttgttta tggtacctgt caccacaaga 360
aaggtgaagc tcgtagatct agacgtgccg tgactcttcc cagtcattcc acaagaaaac 420
ttcaaacgcg ttctcaaact tggctagaaa gtcgtgaata cacgaagcat ttaattcgtg 480
tagagaactg gatctttcgt aacccaggtt tcgctctagc ggccgccgcg atagcttggt 540
tattgggttc atcaacttcc caaaaggtca tttacttagt catgattctt cttatagccc 600
cggcgtactc tatacgttgc atcggtgtat cgaatcgaga ctttgtggaa ggaatgtccg 660
gaggaacctg ggttgatgta gtcctagagc atggtggatg tgtcacagtc atggcccagg 720
ataaacctac ggtagacatc gaattggtta cgacaacagt cagtaatatg gcagaggtaa 780
gatcgtattg ttatgaagca tccatttctg acatggcgtc cgattcacga tgccctaccc 840
agggtgaagc atatctagat aaacagagtg atacacagta cgtgtgtaag agaaccctag 900
ttgacagagg atggggtaac ggttgcggat tgtttggtaa aggaagtcta gtgacgtgcg 960
ccaagttcgc gtgctcaaag aagatgacgg gaaagtcaat ccaaccggag aatcttgaat 1020
accgtatcat gttatcagtg cacggatctc agcattcagg aatgatagta aacgacactg 1080
gacatgagac ggacgagaac agagccaagg tcgaaatcac gcccaattca cctcgtgcag 1140
aggcaaccct tggtggattt ggatcgctag gtcttgactg cgaaccgcga acgggattgg 1200

```
acttttcgga tttgtattat ctaactatga ataacaaaca ttggctagtt cataaggaat   1260

ggttccatga tattcccctt ccctggcatg caggagctga taccggaaca cctcattgga   1320

acaacaagga agcacttgtc gaatttaaag atgcgcatgc gaagcgacaa accgtagttg   1380

tgttgggttc ccaagagggt gctgtgcaca cagccctagc aggtgcgctt gaggcggaaa   1440

tggatggagc aaaaggtaga ctatcttccg gacacttaaa atgcagatta aagatggaca   1500

aacttcgact aaaaggagta agttattcat tatgtacggc cgcatttact tttaccaaaa   1560

taccagccga gacgttgcac ggtacggtta ccgtggaggt acagtatgcg ggtacagatg   1620

gtccgtgcaa ggtgcccgcc caaatggcag ttgacatgca gactttgacg cccgtgggtc   1680

gtttgatcac cgccaacccc gtcatcacgg agtctacgga aaactccaag atgatgttag   1740

agctagaccc tccattcggt gactcgtaca tagtcattgg tgtgggagag aagaagatta   1800

cgcatcattg gcacagatcg ggatcaacaa tcggtaaggc gtttgaggcg acagtgcgag   1860

gtgctaagag aatggcggtc cttggtgata cggcgtggga ttttggatct gtcggaggtg   1920

ctctaaatag tcttggaaaa ggtatccacc agatatttgg agcagcgttt aaatagtagt   1980

cgactagta                                                           1989
```

```
<210> SEQ ID NO 19
<211> LENGTH: 643
<212> TYPE: PRT
<213> ORGANISM: Zika virus

<400> SEQUENCE: 19

Met Gly Lys Arg Ser Ala Gly Ser Ile Met Trp Leu Ala Ser Leu Ala
1               5                   10                  15

Val Val Ile Ala Cys Ala Gly Ala Thr Arg Arg Gly Ser Ala Tyr Tyr
            20                  25                  30

Met Tyr Leu Asp Arg Asn Asp Ala Gly Glu Ala Ile Ser Phe Pro Thr
        35                  40                  45

Thr Leu Gly Met Asn Lys Cys Tyr Ile Gln Ile Met Asp Leu Gly His
    50                  55                  60

Thr Cys Asp Ala Thr Met Ser Tyr Glu Cys Pro Met Leu Asp Glu Gly
65                  70                  75                  80

Val Glu Pro Asp Asp Val Asp Cys Trp Cys Asn Thr Thr Ser Thr Trp
                85                  90                  95

Val Val Tyr Gly Thr Cys His His Lys Lys Gly Glu Ala Arg Arg Ser
            100                 105                 110

Arg Arg Ala Val Thr Leu Pro Ser His Ser Thr Arg Lys Leu Gln Thr
        115                 120                 125

Arg Ser Gln Thr Trp Leu Glu Ser Arg Glu Tyr Thr Lys His Leu Ile
    130                 135                 140

Arg Val Glu Asn Trp Ile Phe Arg Asn Pro Gly Phe Ala Leu Ala Ala
145                 150                 155                 160

Ala Ala Ile Ala Trp Leu Leu Gly Ser Ser Thr Ser Gln Lys Val Ile
                165                 170                 175

Tyr Leu Val Met Ile Leu Leu Ile Ala Pro Ala Tyr Ser Ile Arg Cys
            180                 185                 190

Ile Gly Val Ser Asn Arg Asp Phe Val Glu Gly Met Ser Gly Gly Thr
        195                 200                 205

Trp Val Asp Val Val Leu Glu His Gly Gly Cys Val Thr Val Met Ala
    210                 215                 220

Gln Asp Lys Pro Thr Val Asp Ile Glu Leu Val Thr Thr Thr Val Ser
```

-continued

```
225                 230                 235                 240

Asn Met Ala Glu Val Arg Ser Tyr Cys Tyr Glu Ala Ser Ile Ser Asp
                245                 250                 255

Met Ala Ser Asp Ser Arg Cys Pro Thr Gln Gly Glu Ala Tyr Leu Asp
            260                 265                 270

Lys Gln Ser Asp Thr Gln Tyr Val Cys Lys Arg Thr Leu Val Asp Arg
        275                 280                 285

Gly Trp Gly Asn Gly Cys Gly Leu Phe Gly Lys Gly Ser Leu Val Thr
    290                 295                 300

Cys Ala Lys Phe Ala Cys Ser Lys Lys Met Thr Gly Lys Ser Ile Gln
305                 310                 315                 320

Pro Glu Asn Leu Glu Tyr Arg Ile Met Leu Ser Val His Gly Ser Gln
                325                 330                 335

His Ser Gly Met Ile Val Asn Asp Thr Gly His Glu Thr Asp Glu Asn
            340                 345                 350

Arg Ala Lys Val Glu Ile Thr Pro Asn Ser Pro Arg Ala Glu Ala Thr
        355                 360                 365

Leu Gly Gly Phe Gly Ser Leu Gly Leu Asp Cys Glu Pro Arg Thr Gly
    370                 375                 380

Leu Asp Phe Ser Asp Leu Tyr Tyr Leu Thr Met Asn Asn Lys His Trp
385                 390                 395                 400

Leu Val His Lys Glu Trp Phe His Asp Ile Pro Leu Pro Trp His Ala
                405                 410                 415

Gly Ala Asp Thr Gly Thr Pro His Trp Asn Asn Lys Glu Ala Leu Val
            420                 425                 430

Glu Phe Lys Asp Ala His Ala Lys Arg Gln Thr Val Val Val Leu Gly
        435                 440                 445

Ser Gln Glu Gly Ala Val His Thr Ala Leu Ala Gly Ala Leu Glu Ala
    450                 455                 460

Glu Met Asp Gly Ala Lys Gly Arg Leu Ser Ser Gly His Leu Lys Cys
465                 470                 475                 480

Arg Leu Lys Met Asp Lys Leu Arg Leu Lys Gly Val Ser Tyr Ser Leu
                485                 490                 495

Cys Thr Ala Ala Phe Thr Phe Thr Lys Ile Pro Ala Glu Thr Leu His
            500                 505                 510

Gly Thr Val Thr Val Glu Val Gln Tyr Ala Gly Thr Asp Gly Pro Cys
        515                 520                 525

Lys Val Pro Ala Gln Met Ala Val Asp Met Gln Thr Leu Thr Pro Val
    530                 535                 540

Gly Arg Leu Ile Thr Ala Asn Pro Val Ile Thr Glu Ser Thr Glu Asn
545                 550                 555                 560

Ser Lys Met Met Leu Glu Leu Asp Pro Pro Phe Gly Asp Ser Tyr Ile
                565                 570                 575

Val Ile Gly Val Gly Glu Lys Lys Ile Thr His His Trp His Arg Ser
            580                 585                 590

Gly Ser Thr Ile Gly Lys Ala Phe Glu Ala Thr Val Arg Gly Ala Lys
        595                 600                 605

Arg Met Ala Val Leu Gly Asp Thr Ala Trp Asp Phe Gly Ser Val Gly
    610                 615                 620

Gly Ala Leu Asn Ser Leu Gly Lys Gly Ile His Gln Ile Phe Gly Ala
625                 630                 635                 640

Ala Phe Lys
```

<210> SEQ ID NO 20
<211> LENGTH: 669
<212> TYPE: PRT
<213> ORGANISM: Zika virus

<400> SEQUENCE: 20

```
Thr Arg Arg Gly Ser Ala Tyr Tyr Met Tyr Leu Asp Arg Asn Asp Ala
1               5                   10                  15

Gly Glu Ala Ile Ser Phe Pro Thr Thr Leu Gly Met Asn Lys Cys Tyr
            20                  25                  30

Ile Gln Ile Met Asp Leu Gly His Thr Cys Asp Ala Thr Met Ser Tyr
        35                  40                  45

Glu Cys Pro Met Leu Asp Glu Gly Val Glu Pro Asp Asp Val Asp Cys
    50                  55                  60

Trp Cys Asn Thr Thr Ser Thr Trp Val Val Tyr Gly Thr Cys His His
65                  70                  75                  80

Lys Lys Gly Glu Ala Arg Arg Ser Arg Arg Ala Val Thr Leu Pro Ser
                85                  90                  95

His Ser Thr Arg Lys Leu Gln Thr Arg Ser Gln Thr Trp Leu Glu Ser
            100                 105                 110

Arg Glu Tyr Thr Lys His Leu Ile Arg Val Glu Asn Trp Ile Phe Arg
        115                 120                 125

Asn Pro Gly Phe Ala Leu Ala Ala Ala Ala Ile Ala Trp Leu Leu Gly
    130                 135                 140

Ser Ser Thr Ser Gln Lys Val Ile Tyr Leu Val Met Ile Leu Leu Ile
145                 150                 155                 160

Ala Pro Ala Tyr Ser Ile Arg Cys Ile Gly Val Ser Asn Arg Asp Phe
                165                 170                 175

Val Glu Gly Met Ser Gly Gly Thr Trp Val Asp Val Val Leu Glu His
            180                 185                 190

Gly Gly Cys Val Thr Val Met Ala Gln Asp Lys Pro Thr Val Asp Ile
        195                 200                 205

Glu Leu Val Thr Thr Thr Val Ser Asn Met Ala Glu Val Arg Ser Tyr
    210                 215                 220

Cys Tyr Glu Ala Ser Ile Ser Asp Met Ala Ser Asp Ser Arg Cys Pro
225                 230                 235                 240

Thr Gln Gly Glu Ala Tyr Leu Asp Lys Gln Ser Asp Thr Gln Tyr Val
                245                 250                 255

Cys Lys Arg Thr Leu Val Asp Arg Gly Trp Gly Asn Gly Cys Gly Leu
            260                 265                 270

Phe Gly Lys Gly Ser Leu Val Thr Cys Ala Lys Phe Ala Cys Ser Lys
        275                 280                 285

Lys Met Thr Gly Lys Ser Ile Gln Pro Glu Asn Leu Glu Tyr Arg Ile
    290                 295                 300

Met Leu Ser Val His Gly Ser Gln His Ser Gly Met Ile Val Asn Asp
305                 310                 315                 320

Thr Gly His Glu Thr Asp Glu Asn Arg Ala Lys Val Glu Ile Thr Pro
                325                 330                 335

Asn Ser Pro Arg Ala Glu Ala Thr Leu Gly Gly Phe Gly Ser Leu Gly
            340                 345                 350

Leu Asp Cys Glu Pro Arg Thr Gly Leu Asp Phe Ser Asp Leu Tyr Tyr
        355                 360                 365

Leu Thr Met Asn Asn Lys His Trp Leu Val His Lys Glu Trp Phe His
    370                 375                 380
```

```
Asp Ile Pro Leu Pro Trp His Ala Gly Ala Asp Thr Gly Thr Pro His
385                 390                 395                 400

Trp Asn Asn Lys Glu Ala Leu Val Glu Phe Lys Asp Ala His Ala Lys
                405                 410                 415

Arg Gln Thr Val Val Val Leu Gly Ser Gln Glu Gly Ala Val His Thr
            420                 425                 430

Ala Leu Ala Gly Ala Leu Glu Ala Glu Met Asp Gly Ala Lys Gly Arg
        435                 440                 445

Leu Ser Ser Gly His Leu Lys Cys Arg Leu Lys Met Asp Lys Leu Arg
    450                 455                 460

Leu Lys Gly Val Ser Tyr Ser Leu Cys Thr Ala Ala Phe Thr Phe Thr
465                 470                 475                 480

Lys Ile Pro Ala Glu Thr Leu His Gly Thr Val Thr Val Glu Val Gln
                485                 490                 495

Tyr Ala Gly Thr Asp Gly Pro Cys Lys Val Pro Ala Gln Met Ala Val
            500                 505                 510

Asp Met Gln Thr Leu Thr Pro Val Gly Arg Leu Ile Thr Ala Asn Pro
        515                 520                 525

Val Ile Thr Glu Ser Thr Glu Asn Ser Lys Met Met Leu Glu Leu Asp
    530                 535                 540

Pro Pro Phe Gly Asp Ser Tyr Ile Val Ile Gly Val Gly Glu Lys Lys
545                 550                 555                 560

Ile Thr His His Trp His Arg Ser Gly Ser Thr Ile Gly Lys Ala Phe
                565                 570                 575

Glu Ala Thr Val Arg Gly Ala Lys Arg Met Ala Val Leu Gly Asp Thr
            580                 585                 590

Ala Trp Asp Phe Gly Ser Val Gly Gly Ala Leu Asn Ser Leu Gly Lys
        595                 600                 605

Gly Ile His Gln Ile Phe Gly Ala Ala Phe Lys Ser Leu Phe Gly Gly
    610                 615                 620

Met Ser Trp Phe Ser Gln Ile Leu Ile Gly Thr Leu Leu Met Trp Leu
625                 630                 635                 640

Gly Leu Asn Ala Lys Asn Gly Ser Ile Ser Leu Met Cys Leu Ala Leu
                645                 650                 655

Gly Gly Val Leu Ile Phe Leu Ser Thr Ala Val Ser Ala
            660                 665


<210> SEQ ID NO 21
<211> LENGTH: 619
<212> TYPE: PRT
<213> ORGANISM: Zika virus

<400> SEQUENCE: 21

Thr Arg Arg Gly Ser Ala Tyr Tyr Met Tyr Leu Asp Arg Asn Asp Ala
1               5                   10                  15

Gly Glu Ala Ile Ser Phe Pro Thr Thr Leu Gly Met Asn Lys Cys Tyr
            20                  25                  30

Ile Gln Ile Met Asp Leu Gly His Thr Cys Asp Ala Thr Met Ser Tyr
        35                  40                  45

Glu Cys Pro Met Leu Asp Glu Gly Val Glu Pro Asp Asp Val Asp Cys
    50                  55                  60

Trp Cys Asn Thr Thr Ser Thr Trp Val Val Tyr Gly Thr Cys His His
65                  70                  75                  80

Lys Lys Gly Glu Ala Arg Arg Ser Arg Arg Ala Val Thr Leu Pro Ser
```

-continued

```
                85                  90                  95

His Ser Thr Arg Lys Leu Gln Thr Arg Ser Gln Thr Trp Leu Glu Ser
            100                 105                 110

Arg Glu Tyr Thr Lys His Leu Ile Arg Val Glu Asn Trp Ile Phe Arg
        115                 120                 125

Asn Pro Gly Phe Ala Leu Ala Ala Ala Ala Ile Ala Trp Leu Leu Gly
    130                 135                 140

Ser Ser Thr Ser Gln Lys Val Ile Tyr Leu Val Met Ile Leu Leu Ile
145                 150                 155                 160

Ala Pro Ala Tyr Ser Ile Arg Cys Ile Gly Val Ser Asn Arg Asp Phe
                165                 170                 175

Val Glu Gly Met Ser Gly Gly Thr Trp Val Asp Val Val Leu Glu His
            180                 185                 190

Gly Gly Cys Val Thr Val Met Ala Gln Asp Lys Pro Thr Val Asp Ile
        195                 200                 205

Glu Leu Val Thr Thr Thr Val Ser Asn Met Ala Glu Val Arg Ser Tyr
    210                 215                 220

Cys Tyr Glu Ala Ser Ile Ser Asp Met Ala Ser Asp Ser Arg Cys Pro
225                 230                 235                 240

Thr Gln Gly Glu Ala Tyr Leu Asp Lys Gln Ser Asp Thr Gln Tyr Val
                245                 250                 255

Cys Lys Arg Thr Leu Val Asp Arg Gly Trp Gly Asn Gly Cys Gly Leu
            260                 265                 270

Phe Gly Lys Gly Ser Leu Val Thr Cys Ala Lys Phe Ala Cys Ser Lys
        275                 280                 285

Lys Met Thr Gly Lys Ser Ile Gln Pro Glu Asn Leu Glu Tyr Arg Ile
    290                 295                 300

Met Leu Ser Val His Gly Ser Gln His Ser Gly Met Ile Val Asn Asp
305                 310                 315                 320

Thr Gly His Glu Thr Asp Glu Asn Arg Ala Lys Val Glu Ile Thr Pro
                325                 330                 335

Asn Ser Pro Arg Ala Glu Ala Thr Leu Gly Gly Phe Gly Ser Leu Gly
            340                 345                 350

Leu Asp Cys Glu Pro Arg Thr Gly Leu Asp Phe Ser Asp Leu Tyr Tyr
        355                 360                 365

Leu Thr Met Asn Asn Lys His Trp Leu Val His Lys Glu Trp Phe His
    370                 375                 380

Asp Ile Pro Leu Pro Trp His Ala Gly Ala Asp Thr Gly Thr Pro His
385                 390                 395                 400

Trp Asn Asn Lys Glu Ala Leu Val Glu Phe Lys Asp Ala His Ala Lys
                405                 410                 415

Arg Gln Thr Val Val Val Leu Gly Ser Gln Glu Gly Ala Val His Thr
            420                 425                 430

Ala Leu Ala Gly Ala Leu Glu Ala Glu Met Asp Gly Ala Lys Gly Arg
        435                 440                 445

Leu Ser Ser Gly His Leu Lys Cys Arg Leu Lys Met Asp Lys Leu Arg
    450                 455                 460

Leu Lys Gly Val Ser Tyr Ser Leu Cys Thr Ala Ala Phe Thr Phe Thr
465                 470                 475                 480

Lys Ile Pro Ala Glu Thr Leu His Gly Thr Val Thr Val Glu Val Gln
                485                 490                 495

Tyr Ala Gly Thr Asp Gly Pro Cys Lys Val Pro Ala Gln Met Ala Val
            500                 505                 510
```

-continued

Asp Met Gln Thr Leu Thr Pro Val Gly Arg Leu Ile Thr Ala Asn Pro
515 520 525

Val Ile Thr Glu Ser Thr Glu Asn Ser Lys Met Met Leu Glu Leu Asp
530 535 540

Pro Pro Phe Gly Asp Ser Tyr Ile Val Ile Gly Val Gly Glu Lys Lys
545 550 555 560

Ile Thr His His Trp His Arg Ser Gly Ser Thr Ile Gly Lys Ala Phe
565 570 575

Glu Ala Thr Val Arg Gly Ala Lys Arg Met Ala Val Leu Gly Asp Thr
580 585 590

Ala Trp Asp Phe Gly Ser Val Gly Gly Ala Leu Asn Ser Leu Gly Lys
595 600 605

Gly Ile His Gln Ile Phe Gly Ala Ala Phe Lys
610 615

<210> SEQ ID NO 22
<211> LENGTH: 24
<212> TYPE: PRT
<213> ORGANISM: Zika virus

<400> SEQUENCE: 22

Met Gly Lys Arg Ser Ala Gly Ser Ile Met Trp Leu Ala Ser Leu Ala
1 5 10 15

Val Val Ile Ala Cys Ala Gly Ala
20

<210> SEQ ID NO 23
<211> LENGTH: 643
<212> TYPE: PRT
<213> ORGANISM: Zika virus

<400> SEQUENCE: 23

Met Gly Lys Arg Ser Ala Gly Ser Ile Met Trp Leu Ala Ser Leu Ala
1 5 10 15

Val Val Ile Ala Cys Ala Gly Ala Thr Arg Arg Gly Ser Ala Tyr Tyr
20 25 30

Met Tyr Leu Asp Arg Asn Asp Ala Gly Glu Ala Ile Ser Phe Pro Thr
35 40 45

Thr Leu Gly Met Asn Lys Cys Tyr Ile Gln Ile Met Asp Leu Gly His
50 55 60

Thr Cys Asp Ala Thr Met Ser Tyr Glu Cys Pro Met Leu Asp Glu Gly
65 70 75 80

Val Glu Pro Asp Asp Val Asp Cys Trp Cys Asn Thr Thr Ser Thr Trp
85 90 95

Val Val Tyr Gly Thr Cys His His Lys Lys Gly Glu Ala Arg Arg Ser
100 105 110

Arg Arg Ala Val Thr Leu Pro Ser His Ser Thr Arg Lys Leu Gln Thr
115 120 125

Arg Ser Gln Thr Trp Leu Glu Ser Arg Glu Tyr Thr Lys His Leu Ile
130 135 140

Arg Val Glu Asn Trp Ile Phe Arg Asn Pro Gly Phe Ala Leu Ala Ala
145 150 155 160

Ala Ala Ile Ala Trp Leu Leu Gly Ser Ser Thr Ser Gln Lys Val Ile
165 170 175

Tyr Leu Val Met Ile Leu Leu Ile Ala Pro Ala Tyr Ser Ile Arg Cys
180 185 190

-continued

```
Ile Gly Val Ser Asn Arg Asp Phe Val Glu Gly Met Ser Gly Gly Thr
        195                 200                 205

Trp Val Asp Val Val Leu Glu His Gly Gly Cys Val Thr Val Met Ala
    210                 215                 220

Gln Asp Lys Pro Thr Val Asp Ile Glu Leu Val Thr Thr Thr Val Ser
225                 230                 235                 240

Asn Met Ala Glu Val Arg Ser Tyr Cys Tyr Glu Ala Ser Ile Ser Asp
                245                 250                 255

Met Ala Ser Asp Ser Arg Cys Pro Thr Gln Gly Glu Ala Tyr Leu Asp
            260                 265                 270

Lys Gln Ser Asp Thr Gln Tyr Val Cys Lys Arg Thr Leu Val Asp Arg
        275                 280                 285

Gly Trp Gly Asn Gly Cys Gly Leu Phe Gly Lys Gly Ser Leu Val Thr
    290                 295                 300

Cys Ala Lys Phe Ala Cys Ser Lys Lys Met Thr Gly Lys Ser Ile Gln
305                 310                 315                 320

Pro Glu Asn Leu Glu Tyr Arg Ile Met Leu Ser Val His Gly Ser Gln
                325                 330                 335

His Ser Gly Met Ile Val Asn Asp Thr Gly His Glu Thr Asp Glu Asn
            340                 345                 350

Arg Ala Lys Val Glu Ile Thr Pro Asn Ser Pro Arg Ala Glu Ala Thr
        355                 360                 365

Leu Gly Gly Phe Gly Ser Leu Gly Leu Asp Cys Glu Pro Arg Thr Gly
    370                 375                 380

Leu Asp Phe Ser Asp Leu Tyr Tyr Leu Thr Met Asn Asn Lys His Trp
385                 390                 395                 400

Leu Val His Lys Glu Trp Phe His Asp Ile Pro Leu Pro Trp His Ala
                405                 410                 415

Gly Ala Asp Thr Gly Thr Pro His Trp Asn Asn Lys Glu Ala Leu Val
            420                 425                 430

Glu Phe Lys Asp Ala His Ala Lys Arg Gln Thr Val Val Val Leu Gly
        435                 440                 445

Ser Gln Glu Gly Ala Val His Thr Ala Leu Ala Gly Ala Leu Glu Ala
    450                 455                 460

Glu Met Asp Gly Ala Lys Gly Arg Leu Ser Ser Gly His Leu Lys Cys
465                 470                 475                 480

Arg Leu Lys Met Asp Lys Leu Arg Leu Lys Gly Val Ser Tyr Ser Leu
                485                 490                 495

Cys Thr Ala Ala Phe Thr Phe Thr Lys Ile Pro Ala Glu Thr Leu His
            500                 505                 510

Gly Thr Val Thr Val Glu Val Gln Tyr Ala Gly Thr Asp Gly Pro Cys
        515                 520                 525

Lys Val Pro Ala Gln Met Ala Val Asp Met Gln Thr Leu Thr Pro Val
    530                 535                 540

Gly Arg Leu Ile Thr Ala Asn Pro Val Ile Thr Glu Ser Thr Glu Asn
545                 550                 555                 560

Ser Lys Met Met Leu Glu Leu Asp Pro Pro Phe Gly Asp Ser Tyr Ile
                565                 570                 575

Val Ile Gly Val Gly Glu Lys Lys Ile Thr His His Trp His Arg Ser
            580                 585                 590

Gly Ser Thr Ile Gly Lys Ala Phe Glu Ala Thr Val Arg Gly Ala Lys
        595                 600                 605
```

-continued

```
Arg Met Ala Val Leu Gly Asp Thr Ala Trp Asp Phe Gly Ser Val Gly
    610                 615                 620

Gly Ala Leu Asn Ser Leu Gly Lys Gly Ile His Gln Ile Phe Gly Ala
625                 630                 635                 640

Ala Phe Lys


<210> SEQ ID NO 24
<211> LENGTH: 1929
<212> TYPE: DNA
<213> ORGANISM: Zika virus

<400> SEQUENCE: 24

atgggaaaac gatcagccgg atctataatg tggcttgcaa gtctagctgt tgttattgcc     60

tgtgcgggag cgacgcgtag aggatccgcg tattatatgt atctagatcg taacgacgca    120

ggagaggcta tttcattccc tacgactttg ggtatgaata agtgctacat tcagatcatg    180

gacttaggac acacctgtga tgccacgatg tcctacgagt gccctatgct agatgaagga    240

gtagaaccag atgacgtaga ttgttggtgc aatacgactt ccacatgggt tgtttatggt    300

acctgtcacc acaagaaagg tgaagctcgt agatctagac gtgccgtgac tcttcccagt    360

cattccacaa gaaaacttca aacgcgttct caaacttggc tagaaagtcg tgaatacacg    420

aagcatttaa ttcgtgtaga gaactggatc tttcgtaacc caggtttcgc tctagcggcc    480

gccgcgatag cttggttatt gggttcatca acttcccaaa aggtcattta cttagtcatg    540

attcttctta tagccccggc gtactctata cgttgcatcg gtgtatcgaa tcgagacttt    600

gtggaaggaa tgtccggagg aacctgggtt gatgtagtcc tagagcatgg tggatgtgtc    660

acagtcatgg cccaggataa acctacggtc gacatcgaat tggttacgac aacagtcagt    720

aatatggcag aggtaagatc gtattgttat gaagcatcca tttctgacat ggcgtccgat    780

tcacgatgcc ctacccaggg tgaagcatat ctagataaac agagtgatac acagtacgtg    840

tgtaagagaa ccctagttga cagaggatgg ggtaacggtt gcggattgtt tggtaaagga    900

agtctagtga cgtgcgccaa gttcgcgtgc tcaaagaaga tgacgggaaa gtcaatccaa    960

ccggagaatc ttgaataccg tatcatgtta tcagtgcacg gatctcagca ttcaggaatg   1020

atagtaaacg acactggaca tgagacggac gagaacagag ccaaggtcga aatcacgccc   1080

aattcacctc gtgcagaggc aacccttggt ggatttggat cgctaggtct tgactgcgaa   1140

ccgcgaacgg gattggactt ttcggatttg tattatctaa ctatgaataa caaacattgg   1200

ctagttcata aggaatggtt ccatgatatt cccccttccct ggcatgcagg agctgatacc   1260

ggaacacctc attggaacaa caaggaagca cttgtcgaat ttaaagatgc gcatgcgaag   1320

cgacaaaccg tagttgtgtt gggttcccaa gagggtgctg tgcacacagc cctagcaggt   1380

gcgcttgagg cggaaatgga tggagcaaaa ggtagactat cttccggaca cttaaaatgc   1440

agattaaaaa tggacaaact tcgactaaaa ggagtaagtt attcattatg tacggccgca   1500

tttactttta ccaaaatacc agccgagacg ttgcacggta cggttaccgt ggaggtacag   1560

tatgcgggta cagatggtcc gtgcaaggtg cccgcccaaa tggcagttga catgcagact   1620

ttgacgcccg tgggtcgttt gatcaccgcc aaccccgtca tcacggagtc tacggaaaac   1680

tccaagatga tgttagagct agaccctcca ttcggtgact cgtacatagt cattggtgtg   1740

ggagagaaga agattacgca tcattggcac agatcgggat caacaatcgg taaggcgttt   1800

gaggcgacag tgcgaggtgc taagagaatg gcggtccttg gtgatacggc gtgggatttt   1860

ggatctgtcg gaggtgctct aaatagtctt ggaaaaggta tccaccagat atttggagca   1920
```

-continued gcgtttaaa 1929

<210> SEQ ID NO 25
<211> LENGTH: 1947
<212> TYPE: DNA
<213> ORGANISM: Zika virus

<400> SEQUENCE: 25
cccgggatgg gaaaacgatc agccggatct ataatgtggc ttgcaagtct agctgttgtt 60
attgcctgtg cgggagcgac gcgtagagga tccgcgtatt atatgtatct agatcgtaac 120
gacgcaggag aggctatttc attccctacg actttgggta tgaataagtg ctacattcag 180
atcatggact taggacacac ctgtgatgcc acgatgtcct acgagtgccc tatgctagat 240
gaaggagtag aaccagatga cgtagattgt tggtgcaata cgacttccac atgggttgtt 300
tatggtacct gtcaccacaa gaaaggtgaa gctcgtagat ctagacgtgc cgtgactctt 360
cccagtcatt ccacaagaaa acttcaaacg cgttctcaaa cttggctaga aagtcgtgaa 420
tacacgaagc atttaattcg tgtagagaac tggatctttc gtaacccagg tttcgctcta 480
gcggccgccg cgatagcttg gttattgggt tcatcaactt cccaaaaggt catttactta 540
gtcatgattc ttcttatagc cccggcgtac tctatacgtt gcatcggtgt atcgaatcga 600
gactttgtgg aaggaatgtc cggaggaacc tgggttgatg tagtcctaga gcatggtgga 660
tgtgtcacag tcatggccca ggataaacct acggtagaca tcgaattggt tacgacaaca 720
gtcagtaata tggcagaggt aagatcgtat tgttatgaag catccatttc tgacatggcg 780
tccgattcac gatgccctac ccagggtgaa gcatatctag ataaacagag tgatacacag 840
tacgtgtgta agagaaccct agttgacaga ggatggggta acggttgcgg attgtttggt 900
aaaggaagtc tagtgacgtg cgccaagttc gcgtgctcaa agaagatgac gggaaagtca 960
atccaaccgg agaatcttga ataccgtatc atgttatcag tgcacggatc tcagcattca 1020
ggaatgatag taaacgacac tggacatgag acggacgaga acagagccaa ggtcgaaatc 1080
acgcccaatt cacctcgtgc agaggcaacc cttggtggat ttggatcgct aggtcttgac 1140
tgcgaaccgc gaacgggatt ggacttttcg gatttgtatt atctaactat gaataacaaa 1200
cattggctag ttcataagga atggttccat gatattcccc ttccctggca tgcaggagct 1260
gataccggaa cacctcattg gaacaacaag gaagcacttg tcgaatttaa agatgcgcat 1320
gcgaagcgac aaaccgtagt tgtgttgggt tcccaagagg gtgctgtgca cacagcccta 1380
gcaggtgcgc ttgaggcgga aatggatgga gcaaaaggta gactatcttc cggacactta 1440
aaatgcagat taaagatgga caaacttcga ctaaaaggag taagttattc attatgtacg 1500
gccgcattta cttttaccaa aataccagcc gagacgttgc acggtacggt taccgtggag 1560
gtacagtatg cgggtacaga tggtccgtgc aaggtgcccg cccaaatggc agttgacatg 1620
cagactttga cgcccgtggg tcgtttgatc accgccaacc ccgtcatcac ggagtctacg 1680
gaaaactcca agatgatgtt agagctagac cctccattcg gtgactcgta catagtcatt 1740
ggtgtgggag agaagaagat tacgcatcat tggcacagat cgggatcaac aatcggtaag 1800
gcgtttgagg cgacagtgcg aggtgctaag agaatggcgg tccttggtga tacggcgtgg 1860
gattttggat ctgtcggagg tgctctaaat agtcttggaa aaggtatcca ccagatattt 1920
ggagcagcgt ttaaataata agtcgac 1947